US011401315B2

(12) United States Patent
Macielag et al.

(10) Patent No.: US 11,401,315 B2
(45) Date of Patent: *Aug. 2, 2022

(54) IMMUNOGLOBULINS AND USES THEREOF

(71) Applicant: Janssen Pharmaceutica NV, Beerse (BE)

(72) Inventors: Mark Macielag, Lower Gwynedd, PA (US); Raymond J. Patch, Yardley, PA (US); Rui Zhang, Belle Mead, NJ (US); Martin A. Case, San Diego, CA (US); Shamina M. Rangwala, Furlong, PA (US); James N. Leonard, Ambler, PA (US); Raul C. Camacho, Philadelphia, PA (US); Michael J. Hunter, Santee, CA (US); Katharine E. D'Aquino, Perkasie, PA (US); Wilson Edwards, Cardiff-by the-Sea, CA (US); Ronald V. Swanson, Del Mar, CA (US); Wenying Jian, Princeton, NJ (US); Yue-Mei Zhang, Wellesley, MA (US); Mark J. Wall, Lansdale, PA (US); Ellen Chi, San Diego, CA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

This patent is subject to a terminal disclaimer.

(21) Appl. No.: 16/947,875

(22) Filed: Aug. 21, 2020

(65) Prior Publication Data
US 2020/0385439 A1 Dec. 10, 2020

Related U.S. Application Data

(60) Division of application No. 16/542,751, filed on Aug. 16, 2019, now Pat. No. 10,787,495, which is a
(Continued)

(51) Int. Cl.
| C07K 16/00 | (2006.01) |
| A61K 38/00 | (2006.01) |
| A61K 39/00 | (2006.01) |
| A61K 45/06 | (2006.01) |
| C07K 14/575 | (2006.01) |
| A61K 47/68 | (2017.01) |
| C07K 16/24 | (2006.01) |
| A61K 9/00 | (2006.01) |
| A61K 38/17 | (2006.01) |
| A61K 38/26 | (2006.01) |
| C07K 1/06 | (2006.01) |
| C07K 1/107 | (2006.01) |

(Continued)

(52) U.S. Cl.
CPC .......... C07K 14/575 (2013.01); A61K 9/0019 (2013.01); A61K 38/17 (2013.01); A61K 38/1709 (2013.01); A61K 38/22 (2013.01); A61K 38/26 (2013.01); A61K 45/06 (2013.01); A61K 47/60 (2017.08); A61K 47/64 (2017.08); A61K 47/68 (2017.08); A61K 47/6811 (2017.08); A61K 47/6845 (2017.08); A61K 47/6883 (2017.08); A61K 49/0032 (2013.01); A61K 49/0052 (2013.01); A61K 49/0056 (2013.01); A61P 3/00 (2018.01); A61P 3/04 (2018.01); A61P 3/06 (2018.01); A61P 3/08 (2018.01); A61P 3/10 (2018.01); C07K 1/061 (2013.01); C07K 1/1072 (2013.01); C07K 1/12 (2013.01); C07K 1/18 (2013.01); C07K 5/0205 (2013.01); C07K 14/57545 (2013.01); C07K 16/00 (2013.01); C07K 16/24 (2013.01); A61K 38/00 (2013.01); A61K 2039/505 (2013.01); C07K 2317/14 (2013.01); C07K 2317/21 (2013.01); C07K 2317/24 (2013.01); C07K 2317/33 (2013.01); C07K 2317/52 (2013.01); C07K 2317/55 (2013.01); C07K 2317/56 (2013.01); C07K 2317/565 (2013.01); C07K 2317/567 (2013.01); C07K 2317/71 (2013.01); C07K 2317/92 (2013.01); C07K 2317/94 (2013.01); C07K 2319/30 (2013.01)

(58) Field of Classification Search
None
See application file for complete search history.

(56) References Cited

U.S. PATENT DOCUMENTS

| 4,248,890 A | 2/1981 | Maffrand |
| 5,627,044 A | 5/1997 | Brown |

(Continued)

FOREIGN PATENT DOCUMENTS

| WO | 2005077094 A2 | 8/2005 |
| WO | 2005080424 A2 | 9/2005 |

(Continued)

OTHER PUBLICATIONS

Moll "dyslipidemia causes and treatment" accessed from verywellhealth.com on Feb. 20, 2020, pp. 1-6 (Year: 2020).*

(Continued)

Primary Examiner — Gary B Nickol
Assistant Examiner — Jegatheesan Seharaseyon
(74) Attorney, Agent, or Firm — Ice Miller LLP

(57) ABSTRACT

The present invention relates to a monoclonal antibody platform designed to be coupled to therapeutic peptides to increase the half-life of the therapeutic peptide in a subject. The invention also relates to pharmaceutical compositions and methods for use thereof.

24 Claims, 8 Drawing Sheets
Specification includes a Sequence Listing.

Related U.S. Application Data continuation of application No. 15/794,250, filed on Oct. 26, 2017, now Pat. No. 10,428,134.

(60) Provisional application No. 62/413,613, filed on Oct. 27, 2016, provisional application No. 62/413,586, filed on Oct. 27, 2016.

(51) Int. Cl.

| | | |
|---|---|---|
| *A61K 47/64* | (2017.01) | |
| *A61P 3/10* | (2006.01) | |
| *A61K 49/00* | (2006.01) | |
| *C07K 1/12* | (2006.01) | |
| *C07K 1/18* | (2006.01) | |
| *C07K 5/02* | (2006.01) | |
| *A61K 47/60* | (2017.01) | |
| *A61P 3/08* | (2006.01) | |
| *A61P 3/00* | (2006.01) | |
| *A61P 3/04* | (2006.01) | |
| *A61P 3/06* | (2006.01) | |
| *A61K 38/22* | (2006.01) | |

(56) References Cited

U.S. PATENT DOCUMENTS

| | | | |
|---|---|---|---|
| 7,166,575 | B2 | 1/2007 | Quay |
| 8,759,295 | B2 | 6/2014 | Ghosh |
| 10,428,134 | B2 * | 10/2019 | Macielag ............ A61P 3/10 |
| 10,640,544 | B2 * | 5/2020 | Macielag ............ A61P 3/08 |
| 10,787,495 | B2 * | 9/2020 | Macielag ............ A61K 47/60 |
| 10,858,413 | B2 * | 12/2020 | Macielag ............ C07K 1/1072 |
| 10,961,293 | B2 * | 3/2021 | Macielag ............ C07K 16/24 |
| 10,968,264 | B2 * | 4/2021 | Macielag ............ A61K 38/22 |
| 10,968,265 | B2 * | 4/2021 | Macielag ............ A61K 45/06 |
| 2006/0094653 | A1 | 5/2006 | Levy |
| 2007/0244041 | A1 | 10/2007 | Larsen |
| 2010/0074886 | A1 | 3/2010 | Das |
| 2010/0130424 | A1 | 5/2010 | Swanson |
| 2010/0292172 | A1 | 11/2010 | Ghosh |
| 2013/0040877 | A1 | 2/2013 | Kofoed |
| 2014/0154262 | A1 | 6/2014 | Hanotin |
| 2014/0212440 | A1 | 7/2014 | Jung |
| 2014/0220634 | A1 | 8/2014 | Kehoe |
| 2015/0258209 | A1 | 9/2015 | Benz |
| 2016/0108098 | A1 | 4/2016 | Dock |
| 2017/0121420 | A1 | 5/2017 | Heidrich |

FOREIGN PATENT DOCUMENTS

| | | |
|---|---|---|
| WO | 2011006497 A1 | 1/2011 |
| WO | 2012047583 A2 | 4/2012 |
| WO | 2014073842 A1 | 5/2014 |
| WO | 2014102299 A2 | 7/2014 |
| WO | 2014110368 A1 | 7/2014 |
| WO | 2015157595 A1 | 10/2015 |
| WO | 2016018931 A1 | 2/2016 |

OTHER PUBLICATIONS

Mayo "Metabolic Syndrome" accessed from mayoclinic.org on Feb. 24, 2020, pp. 1-5 (Year: 2020).*

Nichols "Diabetes: the difference between types 1 and 2" accessed from medicalnewstoday.com on Feb. 24, 2020, pp. 1-19 (Year: 2019).*

Maria "The expansion of the therapeutic applications of peptides: drivers and challenges" oligos and peptides, chimica oggo 33(2), pp. 5-15(Year: 2016).*

WHF "Risk Factors" accessed from world-heart-federation.org on Feb. 24, 2020 , pp. 1-18 (Year: 2017).*

Gilman "Clinical effects of ABeta immunization (AN1792) in patients with AD in an interrupted trial" neurology 64, pp. 1553-1562 (Year: 2005).*

William R. Strohl, "Fusion Proteins for Half-Life Extension of Biologics as a Strategy to Make Biobetters", Biodrugs, NZ, vol. 29, No. 4, pp. 215-239, 2015.

Alexey Teplyakov et al, "Structural diversity in a human antibody germline library", MABS, US, vol. 8, No. 6, pp. 1045-1063, 2016.

Lecklin et al., "Agonists for neuropeptide Y receptors Y1 and Y5 stimulate different phases of feeding in guinea pigs," Br. J. Pharmacol. 139(8):1433-40 (2003).

Altschul et al. "Basic Local Alignment Search Tool" J. Mol. Biol., vol. 215, pp. 403-410, 1990.

Altschul et al., "Gapped BLAST and PSI-BLAST: A New Generation of Protein Database Search Programs," Nucleic Acids Research, vol. 25, No. 17, pp. 3389-3402 (1997).

Andrushchenko et al., "Optimization of the hydrochloric acid concentration used for trifluoroacetate removal from Synthetic peptides" Journal of Peptide Science, vol. 13, pp. 37-43, 2007.

Batterham et al., "Inhibition of Food Intake in Obese Subjects by Peptide YY 3-36", The New England Journal of Medicine, vol. 349, No. 10, pp. 941-948, Sep. 2003.

Batterham et al., "Gut hormone PYY3-36 physiologically inhibits food intake.", Nature, Aug. 8, 2002, pp. 650-654, vol. 418.

Challis et al., "Acute effects on PYY3-36 on food intake and hypothalamic neuropeptide expression in the mouse," Biochem Biophys Res Commun 311, vol. No. 4, pp. 915-919, Oct. 2003.

Germain et al., "Analogs of pancreatic polypeptide and peptide YY with a locked PP-fold structure are biologically active," Peptides vol. 39, pp. 6-10, 2013.

Kaiser et al., "Color Test for Detection of Free Terminal Amino Groups in the Solid-Phase Synthesis of Peptides,", Anal. Biochem., 1970, pp. 595-598, vol. 34.

Le Roux et al., "Gut Hormone Profiles Following Bariatric Surgery Favor an Anorectic State, Facilitate Weight Loss, and Improve Metabolic Parameters.", Annals of Surgery, Jan. 2006, pp. 108-114, vol. 243(1).

Palasek et al., "Limiting racemization and aspartimide formation in microwave-enhanced Fmoc solid phase peptide synthesis," Journal of Peptide Science, vol. 13, No. 3, pp. 143-148, 2007.

Pittner et al., "Effects of PYY[3-36] in rodent models of diabetes and obesity.", International Journal of Obesity, 2004, pp. 963-971, vol. 28.

Torang et al., "In vivo and in vitro degradation of peptide YY3-36 to inactive peptide YY3-34 in humans," Am. J. Physiol. Regul. Integr. Comp. Physiol., vol. 310, pp. R866-74, 2016.

Vrang et al., "PYY (3-36) reduces food intake and body weight and improves insulin sensitivity in rodent models of diet-induced obesity", Am J Physiol Regul Integr Comp Physiol, 291, pp. R367-R375, 2006.

Yu et al., "Enhanced Coupling Efficiency in Solid-Phase Peptide Synthesis by Microwave Irradiation.", Journal of Organic Chemistry, Aug. 28, 1992, pp. 4781-4784, vol. 57(18).

Int'l Search Report and Written Opinion dated Feb. 12, 2018 in Int'l Application No. PCT/US2017/058462. 8 pages.

Dennler et al., "Antibody conjugates: from heterogeneous populations to defined reagents," Antibodies vol. 4, pp. 197-224, 2015.

Schjoldager et al., "Oxyntomodulin: a potential hormone from the distal gut. Pharmacokinetics and effects on gastric acid and insulin secretion in man," European Journal of Clinical Investigation, vol. 18, pp. 499-503, 1988.

Young et al., "Preclinical pharmacology of pramlintide in the rat: comparisons with human and rat amylin," Drug Development Research. vol. 37, No. 4, pp. 231-248 1996.

Janes et al., "The selection of pramlintide for clinical evaluation," Diabetes 45(Suppl 2), 235A, 1996.

Wang et al., "New insights into the mechanism of low high-density lipoprotein cholesterol in obesity," Lipids in Health and Disease, vol. 10, No. 176, 10 pages (2011).

Franssen et al., "Obesity and Dyslipidemia," Med. Clin. N. Am., vol. 95, pp. 893-902 (2011).

Klop et al., "Dyslipidemia in Obesity: Mechanisms and Potential Targets," Nutrients, vol. 5, pp. 1218-1240 (2013).

(56) References Cited

OTHER PUBLICATIONS

Oshakbayev et al., "Weight loss therapy for clinical management of patients with some atherosclerotic diseases: a randomized clinical trial," Nutrition Journal, vol. 14, No. 120, 9 pages (2015).
Holland et al., "Impact of intentional weight loss on diabetic kidney disease," Diabetes Obes. Metab., vol. 21, pp. 2338-2341 .(2019).
Reisen et al., "Effect of weight loss without salt restriction on the reduction of blood pressure in overweight hypertensive patients," The New England Journal of Medicine, vol. 298, No. 1, pp. 1-6(1978).
Sheka et al., "Nonalcoholic Steatohepatitis—A Review," JAMA, vol. 323, No. 12, pp. 1175-1183 (2020).
Int'l Search Report and Written Opinion dated Feb. 21, 2018 in Int'l Application No. PCT/US2017/058451 (13 pages).
Int'l Search Report and Written Opinion dated Mar. 13, 2018 in Int'l Application No. PCT/US2017/058455 (11 pages).

\* cited by examiner

Fig. 1
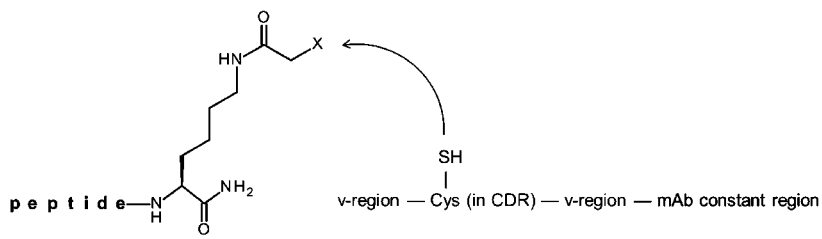
Fig. 2
PH9H5 VH (SEQ ID NO:4)
EVQLLESGGGLVQPGGSLRLSCAASGFTFSSYAMSWVRQAPGKGLEWVSAISGSGGSTYYADSV
KGRFTISRDNSKNTLYLQMNSLRAEDTAVYYCAKYDGIYGELDFWGQGTLVTVSS
PH9L3 VL (SEQ ID NO:3)
EIVLTQSPATLSLSPGERATLSCRASQSVSSYLAWYQQKPGQAPRLLIYDASNRATGIPARFSG
SGSGTDFTLTISSLEPEDFAVYYCQQRSNWPLTFGQGTKVEIK
Fig. 3
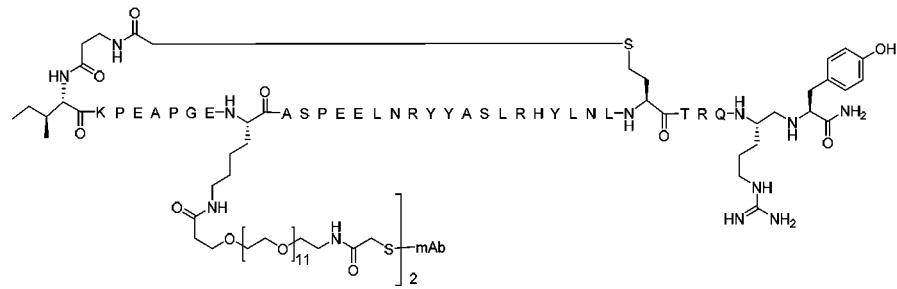

Food Intake in DIO mice post Compound1

TWO-way RM ANOVA, Tukey's
*p< 0.05 Vehicle vs. all groups
p< 0.05 Vehicle vs Compound1
1.0, 3.0, and 7.5nmol/kg

BW change in DIO mice post Compound1

TWO-way RM ANOVA, Tukey's
*p< 0.05 Vehicle vs. all groups
p<0.05 Vehicle vs. Compound1 1.0, 3.0,
7.5 nmol/kg and Dulaglutide
&p<0.05 Vehicle vs. all Compound1 groups Food Intake in DIO mice post Compound1

BW change in DIO mice post Compound1

**OXM-mAb conjugates Ex Vivo Human Plasma Stability
human GLP-1R cAMP assay**

**OXM-mAb conjugates Ex Vivo Cyno Plasma Stability
human GLP-1R cAMP assay**

*p<0.05, versus respective baseline
^p<0.05, versus 7.5 nmol/kg
Two-Way ANOVA RM, Tukey's

IMMUNOGLOBULINS AND USES THEREOF

CROSS-REFERENCE TO RELATED APPLICATIONS

This application is a divisional of U.S. patent application Ser. No. 16/542,751, filed Aug. 16, 2019, which is a continuation of U.S. patent application Ser. No. 15/794,250, now U.S. Pat. No. 10,428,134, filed Oct. 26, 2017, which claims priority to U.S. Provisional Patent Application No. 62/413,613, filed on Oct. 27, 2016, and U.S. Provisional Patent Application No. 62/413,586 filed on Oct. 27, 2016. Each disclosure is incorporated herein by reference in its entirety.

FIELD OF THE INVENTION

The present invention is directed generally to a novel antibody or fragments thereof, and uses thereof as carriers to be coupled to a therapeutic peptide to increase the half-life of the therapeutic peptide in vivo. The invention also relates to pharmaceutical compositions and methods for use thereof.

REFERENCE TO SEQUENCE LISTING SUBMITTED ELECTRONICALLY

This application contains a sequence listing, which is submitted electronically via EFS-Web as an ASCII formatted sequence listing with a file name "004852_67US4_Sequence_Listing" and a creation date of Aug. 10, 2020, and having a size of 20 kb. The sequence listing submitted via EFS-Web is part of the specification and is herein incorporated by reference in its entirety. In the event of any inconsistency with regard to the structures for SEQ ID NOs: 1-27 between the information described herein and the Sequence Listing submitted electronically via EFS-Web with a file name "PRD3459 Sequence Listing," the information herein will prevail.

BACKGROUND OF THE INVENTION

Peptide-based therapeutics are often explored and developed as they can provide the specificity and selectivity, as evidenced by the many approved peptide-based treatments, but the ways in which they can be used are limited by their relatively short in vivo half-lives. There have been numerous half-life extension strategies evaluated and utilized with peptide-based therapeutics. Antibodies or antibody fragments have been used as half-life extension moieties for pharmacologically active moieties to prevent or mitigate rapid in vivo elimination of the pharmacologically active moieties.

There is a need for an improved immunoglobulin that can be used as a pharmacologically inactive half-life extension moiety for pharmacologically active moieties, preferably the peptide-based therapeutics.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

BRIEF SUMMARY OF THE INVENTION

In one general aspect, the present invention relates to an isolated monoclonal antibody or antigen-binding fragment thereof comprising a heavy chain complementarity determining region 1 (HCDR1), a HCDR2, a HCDR3, and a light chain complementarity determining region 1 (LCDR1), a LCDR2, and a LCDR3, having the polypeptide sequences of SEQ ID NO: 16, 17, 18, 19, 20, and 21, respectively.

In a preferred embodiment, an isolated monoclonal antibody or antigen-binding fragment thereof of the invention comprises a heavy chain variable domain (VH) having the polypeptide sequence of SEQ ID NO:12, and a light chain variable domain (VL) having the polypeptide sequence of SEQ ID NO:14. More preferably, an isolated monoclonal antibody of the invention comprises a heavy chain (HC) having the polypeptide sequence of SEQ ID NO:13, and a light chain (LC) having the polypeptide sequence of SEQ ID NO:15.

The invention also relates to an isolated nucleic acid encoding a monoclonal antibody or antigen-binding fragment thereof of the invention; a vector, preferably an expression vector, comprising the nucleic acid; and a host cell comprising the vector. Also provided is a method of producing an isolated monoclonal antibody or antigen binding fragment thereof of the invention, the method comprising culturing a host cell of the invention under conditions to produce the monoclonal antibody or antigen binding fragment thereof, and recovering the antibody or antigen-binding fragment thereof from the cell or culture.

Embodiments of the invention include a monoclonal antibody or antigen-binding fragment thereof of the invention conjugated to at least one pharmacologically active moiety, preferably a therapeutic peptide, directly or via a linker. The monoclonal antibody or antigen-binding fragment thereof of the invention can be conjugated to any therapeutic peptide. Examples of the therapeutic peptide include, but are not limited to, oxyntomodulin, glucagon-like peptide 1 (GLP1), peptide tyrosine tyrosine (PYY), exendin (exenatide), amylin (pramlintide), alpha-melanocyte stimulating hormone (MSH), cocaine- and amphetamine-regulated transcript (CART), neuropeptide Y receptor Y1 (NPY1) antagonists, neuropeptide Y receptor Y5 (NPY5) antagonists, neurotensin S, neuropeptide B, neuropeptide W, ghrelin, bombesin-like receptor 3 (BRS3), galanin, cholecystokinin (CCK), orexin, melanin-concentrating hormone (MCH), oxytocin, and stresscopin.

Also provided is a method of producing a monoclonal antibody or antigen-binding fragment thereof of the invention conjugated to a therapeutic peptide, comprising reacting an electrophile, preferably bromoacetamide or maleimide, introduced onto a sidechain of the therapeutic peptide, with a sulfhydryl group, preferably the sulfhydryl group of the cysteine residue of SEQ ID NO:18, of the monoclonal antibody or antigen-binding fragment thereof, thereby creating a covalent linkage between the therapeutic peptide and the monoclonal antibody or antigen-binding fragment thereof.

The invention also relates to a pharmaceutical composition comprising a monoclonal antibody or antigen-binding fragment thereof of the invention conjugated to at least one pharmacologically active moiety, preferably a therapeutic peptide, directly or via a linker, and a pharmaceutically acceptable carrier.

Another general aspect of the invention relates to a method of increasing the half-life of a therapeutic peptide in a subject, the method comprising conjugating the therapeutic peptide with a monoclonal antibody or antigen-binding fragment thereof comprising a heavy chain complementarity determining region 1 (HCDR1), a HCDR2, a HCDR3, and a light chain complementarity determining region 1

(LCDR1), a LCDR2, and a LCDR3, having the polypeptide sequences of SEQ ID NO: 16, 17, 18, 19, 20, and 21, respectively, wherein the therapeutic peptide is conjugated to the monoclonal antibody or antigen-binding fragment thereof at a sulfhydryl group, preferably the sulfhydryl group of the Cys residue of SEQ ID NO:18.

Further aspects, features and advantages of the present invention will be better appreciated upon a reading of the following detailed description of the invention and claims.

BRIEF DESCRIPTION OF THE DRAWINGS

The foregoing summary, as well as the following detailed description of preferred embodiments of the present application, will be better understood when read in conjunction with the appended drawings. It should be understood, however, that the application is not limited to the precise embodiments shown in the drawings.

FIG. 1: Shows a general peptide-mAb conjugation strategy according to an embodiment of the invention. X represents an electrophile introduced onto a sidechain of a therapeutic peptide, such as bromoacetamide or maleimide, that reacts site specifically with the sulfhydryl group of the Cys residue engineered into a CDR of the half-life extending mAb, creating a covalent linkage between the therapeutic peptide and the mAb.

FIG. 2: Summary of CDR residues selected for substitution in PH9H5_VH (SEQ ID NO:4) and in PH9L3_VL (SEQ ID NO:3). Residues substituted with Cys are bolded and underlined.

FIG. 3: Shows the structure of compound 1 (SEQ ID NO:2).

DETAILED DESCRIPTION OF THE INVENTION

Figure 4:
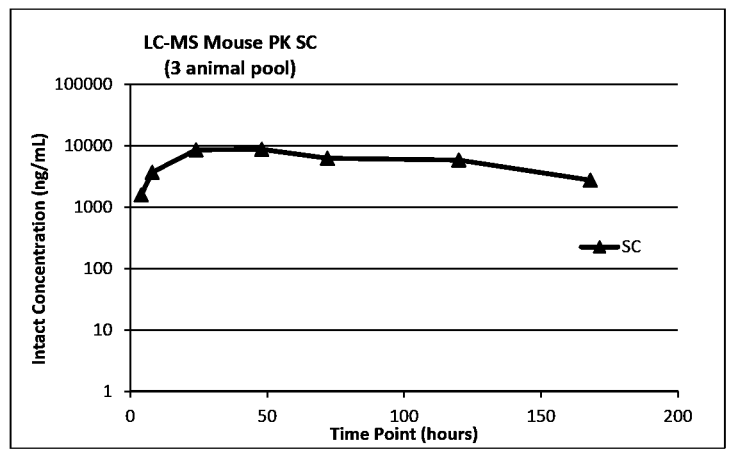
FIG. 4: Pharmacokinetics of the compound 1 in DIO mice.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification.

It must be noted that as used herein and in the appended claims, the singular forms "a," "an," and "the" include plural reference unless the context clearly dictates otherwise.

Unless otherwise stated, any numerical values, such as a concentration or a concentration range described herein, are to be understood as being modified in all instances by the term "about." Thus, a numerical value typically includes ±10% of the recited value. For example, a concentration of 1 mg/mL includes 0.9 mg/mL to 1.1 mg/mL. Likewise, a concentration range of 1% to 10% (w/v) includes 0.9% (w/v) to 11% (w/v). As used herein, the use of a numerical range expressly includes all possible subranges, all individual numerical values within that range, including integers within such ranges and fractions of the values unless the context clearly indicates otherwise.

Unless otherwise indicated, the term "at least" preceding a series of elements is to be understood to refer to every element in the series. Those skilled in the art will recognize or be able to ascertain using no more than routine experimentation, many equivalents to the specific embodiments of the invention described herein. Such equivalents are intended to be encompassed by the invention.

As used herein, the terms "comprises," "comprising," "includes," "including," "has," "having," "contains" or "containing," or any other variation thereof, will be understood to imply the inclusion of a stated integer or group of integers but not the exclusion of any other integer or group of integers and are intended to be non-exclusive or open-ended. For example, a composition, a mixture, a process, a method, an article, or an apparatus that comprises a list of elements is not necessarily limited to only those elements but can include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

It should also be understood that the terms "about," "approximately," "generally," "substantially" and like terms, used herein when referring to a dimension or characteristic of a component of the preferred invention, indicate that the described dimension/characteristic is not a strict boundary or parameter and does not exclude minor variations therefrom that are functionally the same or similar, as would be understood by one having ordinary skill in the art. At a minimum, such references that include a numerical parameter would include variations that, using mathematical and industrial principles accepted in the art (e.g., rounding, measurement or other systematic errors, manufacturing tolerances, etc.), would not vary the least significant digit.

The terms "identical" or percent "identity," in the context of two or more nucleic acids or polypeptide sequences (e.g., cyclic $PYY_{3-36}$ polypeptide sequences, oxyntomodulin polypeptide sequences, antibody light chain or heavy chain sequences), refer to two or more sequences or subsequences that are the same or have a specified percentage of amino acid residues or nucleotides that are the same, when compared and aligned for maximum correspondence, as measured using one of the sequence comparison algorithms or by visual inspection using methods known in the art in view of the present disclosure.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Current Protocols in Molecular Biology, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) J. Mol. Biol. 215: 403-410 and Altschul et al. (1997) Nucleic Acids Res. 25: 3389-3402, respectively. Software for performing BLAST analyses is publicly available through the National Center for Biotechnology Information.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

As used herein, "subject" means any animal, preferably a mammal, most preferably a human. The term "mammal" as used herein, encompasses any mammal. Examples of mammals include, but are not limited to, cows, horses, sheep, pigs, cats, dogs, mice, rats, rabbits, guinea pigs, monkeys, humans, etc., more preferably a human.

The term "administering" with respect to the methods of the invention, means a method for therapeutically or prophylactically preventing, treating or ameliorating a syndrome, disorder or disease as described herein by using a conjugate of the invention or a form, composition or medicament thereof. Such methods include administering an effective amount of said conjugate, conjugate form, composition or medicament at different times during the course of a therapy or concurrently in a combination form. The methods of the invention are to be understood as embracing all known therapeutic treatment regimens.

The term "effective amount" means that amount of active conjugate or pharmaceutical agent that elicits the biological or medicinal response in a tissue system, animal or human, that is being sought by a researcher, veterinarian, medical doctor, or other clinician, which includes preventing, treating or ameliorating a syndrome, disorder, or disease being treated, or the symptoms of a syndrome, disorder or disease being treated.

As used herein, the term "composition" is intended to encompass a product comprising the specified ingredients in the specified amounts, as well as any product which results, directly or indirectly, from combinations of the specified ingredients in the specified amounts.

As used herein the term "coupled" refers to the joining or connection of two or more objects together. When referring to chemical or biological compounds, coupled can refer to a covalent connection between the two or more chemical or biological compounds. By way of a non-limiting example, an antibody of the invention can be coupled with a peptide of interest to form an antibody coupled peptide. An antibody coupled peptide can be formed through specific chemical reactions designed to conjugate the antibody to the peptide. In certain embodiments, an antibody of the invention can be covalently coupled with a peptide of the invention through a linker. The linker can, for example, be first covalently connected to the antibody or the peptide, then covalently connected to the peptide or the antibody.

As used herein, the term "linker" refers to a chemical module comprising a covalent or atomic chain that covalently attaches a peptide to an antibody. The linker can, for example, include, but is not limited to, a peptide linker, a hydrocarbon linker, a polyethylene glycol (PEG) linker, a polypropylene glycol (PPG) linker, a polysaccharide linker, a polyester linker, a hybrid linker consisting of PEG and an embedded heterocycle, and a hydrocarbon chain. The PEG linkers can, for example, comprise 2-24 PEG units.

As used herein, the term "conjugate" refers to an antibody or a fragment thereof covalently coupled to a pharmaceutically active moiety. The term "conjugated to" refers to an antibody or a fragment thereof of invention covalently linked to or covalently connected to a pharmaceutically active moiety, preferably a therapeutic peptide, directly or indirectly via a linker. By way of a non-limiting example, the antibody can be a monoclonal antibody of the invention and the pharmaceutically active moiety can be a therapeutic peptide, such as a cyclic PYY, an oxyntomodulin peptide, or any other therapeutic peptide of interest. The pharmaceutically active moiety can also be a non-peptide organic moiety (i.e., "small molecule"). In the present disclosure, with respect to an antibody or antigen binding fragment thereof according to an embodiment of the invention, the phrase "a conjugate comprising an antibody or antigen binding fragment thereof and a pharmaceutically active moiety (or therapeutic peptide) conjugated thereto" is used interchangeably with the phrase "an antibody or antigen binding fragment thereof conjugated to a pharmaceutically active moiety (or a therapeutic peptide)."

The peptide sequences described herein are written according to the usual convention whereby the N-terminal region of the peptide is on the left and the C-terminal region is on the right. Although isomeric forms of the amino acids are known, it is the L-form of the amino acid that is represented unless otherwise expressly indicated.

Antibodies

In one general aspect, the invention relates to a novel antibody, which has been engineered to be non-targeting and to contain a cysteine residue capable of being used to chemically conjugate (i.e., couple) a pharmaceutically active moiety, such as a therapeutic peptide (e.g., a cyclic PYY peptide, an oxyntomodulin or variant peptide, etc.), in a site-specific manner, such that the antibody coupled peptide has an extended/increased half-life compared to the peptide alone. As used herein, the term "non-targeting" in the context of an antibody refers to an antibody that does not specifically bind to any target in vivo. As used herein, an antibody that "specifically binds to a target" refers to an antibody that binds to a target antigen, with a KD of $1\times10^{-7}$ M or less, preferably $1\times10^{-8}$ M or less, more preferably $5\times10^{-9}$ M or less, $1\times10^{-9}$ M or less, $5\times10^{-10}$ M or less, or $1\times10^{-10}$ M or less. The term "KD" refers to the dissociation constant, which is obtained from the ratio of Kd to Ka (i.e., Kd/Ka) and is expressed as a molar concentration (M). KD values for antibodies can be determined using methods in the art in view of the present disclosure. For example, the KD of an antibody can be determined by using surface plasmon resonance, such as by using a biosensor system, e.g., a BIACORE® system, or by using bio-layer interferometry technology, such as a Octet RED96 system. The smaller the value of the KD of an antibody, the higher affinity that the antibody binds to a target antigen.

Monoclonal antibodies, complete or a fragment thereof, can be used as a half-life extending moiety. Monoclonal antibodies are well-studied proteins that have been utilized and characterized for uses in vivo, and as such, the mechanisms that enable their protracted half-life in vivo and the mechanisms for their elimination in vivo are well understood. Additionally, the spatial separation and presentation of the two "arms" of the monoclonal antibody can be advantageous for effective bivalent presentation of a therapeutic moiety (i.e., a therapeutic peptide). Therapeutics in which toxins or other small molecule drugs are chemically linked to a monoclonal antibody have been developed but typically utilize a monoclonal antibody that binds to a specific antigen and targets the antibody-drug conjugate to a tissue/cell of interest, which preferentially expressed the antigen, and typically the drug/small molecule is attached to the antibody in a manner that does not impact antigen binding of the antibody.

For therapeutic peptide-mAb conjugates, antigen specific binding by the half-life extending monoclonal antibody is not desired. Because of this, a heavy chain (HC) and light chain (LC) variable (V) domain pair not expected to specifically bind any target are used for preparing the coupling-enabled, non-targeting monoclonal antibody of the invention. To obtain a coupling-enabled, non-targeting monoclonal antibody, a cysteine residue is engineered into one of the complementarity determining regions (CDRs) of a selected non-targeting antibody. The pharmaceutically active moiety (e.g., therapeutic peptide/compound) can contain the appropriate chemical moiety to allow for the conjugation of the pharmaceutically active moiety to the engineered cysteine residue of the non-targeting monoclonal antibody. A peptide-monoclonal antibody general conjugation strategy according to an embodiment of the invention is shown in FIG. 1.

The term "antibodies" as used herein is meant in a broad sense and includes non-human (e.g., murine, rat), human, human-adapted, humanized and chimeric monoclonal antibodies, antibody fragments, bispecific or multispecific antibodies, dimeric, tetrameric or multimeric antibodies, and single chain antibodies.

Antibody light chains of any vertebrate species can be assigned to one of two clearly distinct types, namely kappa (κ) and lambda (λ), based on the amino acid sequences of their constant domains. Accordingly, the antibodies of the invention can contain a kappa or lambda light chain constant domain. According to particular embodiments, the antibodies of the invention include heavy and/or light chain constant regions, e.g., from mouse or human antibodies. In addition to the heavy and light constant domains, antibodies contain an antigen-binding region that is made up of a light chain variable region and a heavy chain variable region, each of which contains three domains (i.e., complementarity determining regions 1-3; (CDR1, CDR2, and CDR3)). The light chain variable region domains are alternatively referred to as LCDR1, LCDR2, and LCDR3, and the heavy chain variable region domains are alternatively referred to as HCDR1, HCDR2, and HCDR3.

Immunoglobulins can be assigned to five major classes, namely IgA, IgD, IgE, IgG and IgM, depending on the heavy chain constant domain amino acid sequence. IgG is the most stable of the five types of immunoglobulins, having a serum half-life in humans of about 23 days. IgA and IgG are further sub-classified as the isotypes $IgA_1$, $IgA_2$, $IgG_1$, $IgG_2$, $IgG_3$ and $IgG_4$. Each of the four IgG subclasses has different biological functions known as effector functions. These effector functions are generally mediated through interaction with the Fc receptor (FcγR) or by binding C1q and fixing complement. Binding to FcγR can lead to antibody dependent cell mediated cytolysis, whereas binding to complement factors can lead to complement mediated cell lysis. An antibody of the invention utilized for its ability to extend half-life of a therapeutic peptide has no or minimal effector function, but retains its ability to bind FcRn, the binding of which can be a primary means by which antibodies have an extended in vivo half-life.

In one embodiment, the invention relates to an isolated antibody or antigen binding fragment thereof comprising a light chain variable region having completely human Ig germline V gene sequences, and a heavy chain variable region having completely human Ig germline V gene sequences except HCDR3 having the amino acid sequence of SEQ ID NO:18, wherein the antibody or antigen binding fragment thereof does not specifically bind to any human antigen in vivo. In certain embodiments, the invention relates to an isolated antibody or antigen binding fragment thereof comprising a light chain variable region having completely human Ig germline V gene sequences, and a heavy chain variable region having completely human Ig germline V gene sequences except HCDR3 having the amino acid sequence of SEQ ID NO:18, wherein the antibody or antigen binding fragment thereof does not specifically bind to any human antigen in vivo, wherein the isolated antibody or antigen binding fragment thereof is coupled to a pharmaceutically active moiety (e.g., a cyclic PYY peptide, an oxyntomodulin peptide, and/or a therapeutic peptide of the invention).

As used herein, the term "antigen-binding fragment" refers to an antibody fragment such as, for example, a diabody, a Fab, a Fab', a F(ab')2, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), a single domain antibody (sdab) an scFv dimer (bivalent diabody), a multi-specific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment binds. According to particular embodiments, the antigen-binding fragment comprises a light chain variable region, a light chain constant region, and an Fd segment (i.e., portion of the heavy chain which is included in the Fab fragment). According to other particular embodiments, the antigen-binding fragment comprises Fab and F(ab').

As used herein, the term "single-chain antibody" refers to a conventional single-chain antibody in the field, which comprises a heavy chain variable region and a light chain variable region connected by a short peptide of about 15 to about 20 amino acids. As used herein, the term "single domain antibody" refers to a conventional single domain antibody in the field, which comprises a heavy chain variable region and a heavy chain constant region or which comprises only a heavy chain variable region.

The phrase "isolated antibody or antibody fragment" refers to an antibody or antibody fragment that is substantially free of other antibodies having different antigenic specificities (e.g., an isolated antibody specifically binding a target antigen is substantially free of antibodies that specifically do not bind the target antigen). Moreover, an isolated antibody or antibody fragment can be substantially free of other cellular material and/or chemicals.

An antibody variable region consists of a "framework" region interrupted by three "antigen binding sites". The antigen binding sites are defined using various terms: (i) Complementarity Determining Regions (CDRs), three in the VH (HCDR1, HCDR2, HCDR3), and three in the VL (LCDR1, LCDR2, LCDR3), are based on sequence variability (Wu and Kabat J Exp Med 132:211-50, 1970; Kabat et al Sequences of Proteins of Immunological Interest, 5th Ed. Public Health Service, National Institutes of Health, Bethesda, Md., 1991). (ii) "Hypervariable regions," "HVR," or "HV," three in the VH (H1, H2, H3) and three in the VL (L1, L2, L3), refer to the regions of an antibody variable domains which are hypervariable in structure as defined by Chothia and Lesk (Chothia and Lesk Mol Biol 196:901-17, 1987). Other terms include "IMGT-CDRs" (Lefranc et al., Dev Comparat Immunol 27:55-77, 2003) and "Specificity Determining Residue Usage" (SDRU) (Almagro Mol Recognit 17:132-43, 2004). The International ImMunoGeneTics (IMGT) database (http://www_mgt_org) provides a standardized numbering and definition of antigen-binding sites. The correspondence between CDRs, HVs and IMGT delineations is described in Lefranc et al., Dev Comparat Immunol 27:55-77, 2003.

"Framework" or "framework sequences" are the remaining sequences of a variable region other than those defined to be antigen binding sites. Because the antigen binding sites can be defined by various terms as described above, the exact amino acid sequence of a framework depends on how the antigen-binding site was defined.

In one embodiment of the invention, an isolated antibody or antigen binding fragment thereof comprises a light chain variable region having the LCDR1, LCDR2 and LCDR3 of the amino acid sequence of SEQ ID NO: 19, SEQ ID NO: 20 and SEQ ID NO: 21, respectively, and a heavy chain variable region having the HCDR1, HCDR2 and HCDR3 of the amino acid sequences of SEQ ID NO: 16, SEQ ID NO: 17 and SEQ ID NO: 18, respectively.

In another embodiment, the isolated antibody further comprises a Fc region derived from human IgG4 Fc region. Human IgG4 Fc region has reduced ability to bind FcγR and complement factors compared to other IgG sub-types. Preferably, the Fc region contains human IgG4 Fc region having substitutions that eliminate effector function. Thus, the isolated antibody further comprises a Fc region having a modified human IgG4 Fc region containing one or more of the following substitutions: substitution of proline for glutamate at residue 233, alanine or valine for phenylalanine at residue 234 and alanine or glutamate for leucine at residue 235 (EU numbering, Kabat, E. A. et al. (1991) Sequences of Proteins of Immunological Interest, 5th Ed. U.S. Dept. of Health and Human Services, Bethesda, Md., NIH Publication no. 91-3242). Removing the N-linked glycosylation site in the IgG4 Fc region by substituting Ala for Asn at residue 297 (EU numbering) is another way to ensure that residual effector activity is eliminated.

Preferably, an antibody of the invention exists as dimers joined together by disulfide bonds and various non-covalent interactions. Thus, the Fc portion useful for the antibody of the invention can be human IgG4 Fc region containing a substitution, such as serine to proline at position at 228 (EU numbering), that stabilizes heavy chain dimer formation and prevents the formation of half-IgG4 Fc chains.

In another embodiment, the C-terminal Lys residue in the heavy chain is removed, as commonly seen in recombinantly produced monoclonal antibodies.

"Human antibody" refers to an antibody having heavy and light chain variable regions in which both the framework and the antigen binding sites are derived from sequences of human origin. If the antibody contains a constant region, the constant region also is derived from sequences of human origin.

Human antibody comprises heavy or light chain variable regions that are "derived from" sequences of human origin if the variable regions of the antibody are obtained from a system that uses human germline immunoglobulin or rearranged immunoglobulin genes. Such systems include human immunoglobulin gene libraries displayed on phage, and transgenic non-human animals such as mice carrying human immunoglobulin loci as described herein. "Human antibody" may contain amino acid differences when compared to the human germline or rearranged immunoglobulin sequences due to for example naturally occurring somatic mutations or intentional introduction of substitutions in the framework or antigen binding sites. Typically, "human antibody" is at least about 80%, 81%, 82%, 83%, 84%, 85%, 86%, 87%, 88%, 89%, 90%, 91%, 92%, 93%, 94%, 95%, 96%, 97%, 98%, 99% or 100% identical in amino acid sequence to an amino acid sequence encoded by a human germline or rearranged immunoglobulin gene. In some cases, "human antibody" may contain consensus framework sequences derived from human framework sequence analyses, for example as described in Knappik et al., J Mol Biol 296:57-86, 2000), or synthetic HCDR3 incorporated into human immunoglobulin gene libraries displayed on phage, for example as described in Shi et al., J Mol Biol 397:385-96, 2010 and Intl. Pat. Publ. No. WO2009/085462). Antibodies in which antigen binding sites are derived from a non-human species are not included in the definition of "human antibody".

Isolated antibodies according to embodiment of the invention can be synthetic. The antibodies, while derived from human immunoglobulin sequences, can be generated using systems such as phage display incorporating synthetic CDRs and/or synthetic frameworks, or can be subjected to in vitro mutagenesis to improve antibody properties, resulting in antibodies that do not naturally exist within the human antibody germline repertoire in vivo.

The term "recombinant antibody" as used herein, includes all antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, antibodies isolated from a recombinant, combinatorial antibody library, and antibodies prepared, expressed, created or isolated by any other means that involve splicing of human immunoglobulin gene sequences to other DNA sequences, or antibodies that are generated in vitro using Fab arm exchange.

The term "monoclonal antibody" as used herein refers to a preparation of antibody molecules of a single molecular composition. A monoclonal antibody composition displays a single binding specificity and affinity for a particular epitope, or in a case of a bispecific monoclonal antibody, a dual binding specificity to two distinct epitopes. The monoclonal antibodies of the invention can be made by the hybridoma method, phage display technology, single lymphocyte gene cloning technology, or by recombinant DNA methods. For example, the monoclonal antibodies can be produced by a hybridoma which includes a B cell obtained from a transgenic nonhuman animal, such as a transgenic mouse or rat, having a genome comprising a human heavy chain transgene and a light chain transgene.

In certain embodiments, the term "mAb" refers to a monoclonal antibody. In one embodiment, the mAb has a heavy chain variable region (VH) sequence comprising SEQ ID NO:12 and a light chain variable region (VL) sequence comprising SEQ ID NO:14. In certain embodiments the mAb is a fully human monoclonal antibody having a heavy chain (HC) sequence comprising SEQ ID NO:13 and a light chain (LC) sequence comprising SEQ ID NO:15. In certain embodiments, the lysine residue at position 446 of SEQ ID NO:13 is optionally missing.

As used herein, the term "chimeric antibody" refers to an antibody wherein the amino acid sequence of the immunoglobulin molecule is derived from two or more species. The variable region of both the light and heavy chains often corresponds to the variable region of an antibody derived from one species of mammal (e.g., mouse, rat, rabbit, etc.) having the desired specificity, affinity, and capability, while the constant regions correspond to the sequences of an antibody derived from another species of mammal (e.g., human) to avoid eliciting an immune response in that species.

As used herein, the term "multispecific antibody" refers to an antibody that comprises a plurality of immunoglobulin variable domain sequences, wherein a first immunoglobulin variable domain sequence of the plurality has binding specificity for a first epitope or comprises germline sequences lacking any known binding specificity and a second immunoglobulin variable domain sequence of the plurality has binding specificity for a second epitope or comprises germline sequences lacking any known binding specificity, and wherein the first and/or second immunoglobulin variable domain optionally include a conjugated pharmaceutically active moiety (e.g., a therapeutic peptide). In an embodiment, the first and second epitopes are on the same antigen, e.g., the same protein (or subunit of a multimeric protein). In an embodiment, the first and second epitopes overlap or substantially overlap. In an embodiment, the first and second epitopes do not overlap or do not substantially overlap. In an embodiment, the first and second epitopes are on different antigens, e.g., the different proteins (or different subunits of a multimeric protein). In an embodiment, the first and second immunoglobulin variable domains include the same conjugated pharmaceutically active moiety. In an embodiment, the first and second immunoglobulin variable domains include different pharmaceutically active moieties. In an embodiment, only the first immunoglobulin variable domain includes a conjugated pharmaceutically active moiety. In an embodiment, only the second immunoglobulin variable domain includes a conjugated pharmaceutically active moiety. In an embodiment, a multispecific antibody comprises a third, fourth, or fifth immunoglobulin variable domain. In an embodiment, a multispecific antibody is a bispecific antibody molecule, a trispecific antibody, or a tetraspecific antibody molecule.

As used herein, the term "bispecific antibody" refers to a multispecific antibody that binds no more than two epitopes or two antigens and/or comprises two conjugated pharmaceutically active moieties (e.g., the same or different pharmaceutically active moiety). A bispecific antibody is characterized by a first immunoglobulin variable domain sequence which has binding specificity for a first epitope or comprises germline sequences lacking any known binding specificity and a second immunoglobulin variable domain sequence that has binding specificity for a second epitope or comprises germline sequences lacking any known binding specificity, and wherein the first and/or second immunoglobulin variable domain optionally include a conjugated pharmaceutically active moiety. In an embodiment, the first and second epitopes are on the same antigen, e.g., the same protein (or subunit of a multimeric protein). In an embodiment, the first and second epitopes overlap or substantially overlap. In an embodiment the first and second epitopes are on different antigens, e.g., the different proteins (or different subunits of a multimeric protein). In an embodiment, the first and second immunoglobulin variable domains include the same conjugated pharmaceutically active moiety. In an embodiment, the first and second immunoglobulin variable domains include different pharmaceutically active moieties. In an embodiment, only the first immunoglobulin variable domains includes a conjugated pharmaceutically active moiety. In an embodiment, only the second immunoglobulin variable domain includes a conjugated pharmaceutically active moiety. In an embodiment a bispecific antibody comprises a first heavy chain variable domain sequence and light chain variable domain sequence which have binding specificity for a first epitope or comprise germline sequences lacking any known binding specificity and a second heavy chain variable domain sequence and light chain variable domain sequence which have binding specificity for a second epitope or comprise germline sequences lacking any known binding specificity, and wherein the first and/or second heavy chain variable domains optionally include a conjugated pharmaceutically active moiety. In an embodiment, the first and second heavy chain variable domains include the same conjugated pharmaceutically active moiety. In an embodiment, the first and second heavy chain variable domains include different conjugated pharmaceutically active moieties. In an embodiment, only the first heavy chain variable domain includes a conjugated pharmaceutically active moiety. In an embodiment, only the second heavy chain variable domain includes a conjugated pharmaceutically active moiety.

"Full length antibody" as used herein refers to an antibody having two full length antibody heavy chains and two full length antibody light chains. A full length antibody heavy chain (HC) consists of a heavy chain variable region (VH) and constant domains (CH1, CH2, and CH3). A full length antibody light chain (LC) consists of a light chain variable region (VL) and constant domain (CL). The full length antibody can be lacking the C-terminal lysine (K) in either one or both heavy chains.

The term "Fab-arm" or "half molecule" refers to one heavy chain-light chain pair.

Full length bispecific antibodies can be generated for example using Fab arm exchange (or half molecule exchange) between two monospecific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent monospecific antibodies are reduced. The resulting free cysteines of one of the parent monospecific antibodies form an inter heavy-chain disulfide bond with cysteine residues of a second parent monospecific antibody molecule and simultaneously CH3 domains of the parent antibodies release and reform by dissociation-association. The CH3 domains of the Fab arms may be engineered to favor heterodimerization over homodimerization. The resulting product is a bispecific antibody having two Fab arms or half molecules which each can bind a distinct epitope.

"Homodimerization" as used herein, with respect to the antibodies, refers to an interaction of two heavy chains having identical CH3 amino acid sequences. "Homodimer" as used herein, with respect to the antibodies, refers to an antibody having two heavy chains with identical CH3 amino acid sequences.

"Heterodimerization" as used herein, with respect to the antibodies, refers to an interaction of two heavy chains having non-identical CH3 amino acid sequences. "Heterodimer" as used herein, with respect to the antibodies, refers to an antibody having two heavy chains with non-identical CH3 amino acid sequences.

The "knob-in-hole" strategy (see, e.g., PCT Intl. Publ. No. WO 2006/028936) can be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by following substitutions (expressed as modified position in the first CH3 domain of the first heavy chain/modified position in the second CH3 domain of the second heavy chain): L351Y_F405A_Y407V/T394W, T366I_K392M_T394W/F405A_Y407V, T366L_K392M_T394W/F405A_Y407V, L351Y_Y407A/T366A_K409F, L351Y_Y407A/T366V_K409F, Y407A/T366A_K409F, or T350V_L351Y_F405A_Y407V/T350V_T366L_K392L_T394W as described in U.S. Pat. Publ. No. US2012/0149876 or U.S. Pat. Publ. No. US2013/0195849.

In addition to methods described above, bispecific antibodies can be generated in vitro in a cell-free environment by introducing asymmetrical mutations in the CH3 regions of two monospecific homodimeric antibodies and forming the bispecific heterodimeric antibody from two parent monospecific homodimeric antibodies in reducing conditions to allow disulfide bond isomerization according to methods described in Intl. Pat. Publ. No. WO2011/131746. In the methods, the first monospecific bivalent antibody and the second monospecific bivalent antibody are engineered to have certain substitutions at the CH3 domain that promoter heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing. Exemplary reducing agents that may be used are 2-mercaptoethylamine (2-MEA), dithiothreitol (DTT), dithioerythritol (DTE), glutathione, tris(2-carboxyethyl)phosphine (TCEP), L-cysteine and beta-mercaptoethanol, preferably a reducing agent selected from the group consisting of: 2-mercaptoethylamine, dithiothreitol and tris(2-carboxyethyl)phosphine. For example, incubation for at least 90 min at a temperature of at least 20° C. in the presence of at least 25 mM 2-MEA or in the presence of at least 0.5 mM dithiothreitol at a pH of from 5-8, for example at pH of 7.0 or at pH of 7.4 may be used.

The numbering of amino acid residues in the antibody constant region throughout the specification is performed according to the EU index as described in Kabat et al., Sequences of Proteins of Immunological Interest, 5th Ed. Public Health Service, National Institutes of Health, Bethesda, Md. (1991), unless otherwise explicitly stated.

Conjugates

In another general aspect, the invention relates to a conjugate comprising an antibody of the invention covalently conjugated to a pharmaceutically active moiety, such as a synthetic therapeutic peptide (e.g., a cyclic PYY peptide or an oxyntomodulin variant peptide), in a site-specific manner, such that the antibody coupled peptide has an extended/increased half-life compared to the peptide alone. The conjugates are useful for preventing, treating, or ameliorating diseases or disorders disclosed herein. The invention also relates to pharmaceutical compositions, methods of preparation and methods for use thereof.

In certain embodiments, the antibody of the invention is modified to comprise at least one cysteine residue substitution that is capable of being conjugated to the pharmaceutically active moiety to extend/increase the half-life of the pharmaceutically active moiety. In certain embodiments, the at least one cysteine residue substitution is comprised in a complementarity determining region of the antibody. In certain embodiments, the at least one cysteine residue substitution is in a heavy chain complementarity determining region (HCDR). In certain embodiments, the at least one cysteine residue substitution is in an HCDR3, wherein the HCDR3 comprises an amino acid sequence of SEQ ID NO:18. In certain embodiments, the antibody comprising an HCDR3 comprising an amino acid sequence of SEQ ID NO:18 has at least one additional cysteine substitution that is capable of being conjugated to the pharmaceutically active moiety.

In certain embodiments the pharmaceutically active moiety can comprise a linker. The linker can be modified chemically to allow for the conjugation of the antibody to the pharmaceutically active moiety. The linker can, for example, include, but is not limited to, a peptide linker, a hydrocarbon linker, a polyethylene glycol (PEG) linker, a polypropylene glycol (PPG) linker, a polysaccharide linker, a polyester linker, a hybrid linker consisting of PEG and an embedded heterocycle, and a hydrocarbon chain. The PEG linkers can, for example, comprise 2-24 PEG units.

In certain embodiments, a monoclonal antibody of the invention is conjugated to one, two, three, four, five, or six pharmaceutically active moieties (e.g., therapeutic peptide(s)) of interest. In preferred embodiments, the non-targeting monoclonal antibody is conjugated to two pharmaceutically active moieties of interest. In certain embodiments where the monoclonal antibody is conjugated to at least two pharmaceutically active moieties of interest, the pharmaceutically active moieties of interest can be the same pharmaceutically active moiety or can be different pharmaceutically active moieties.

Methods of conjugating antibodies of the invention with the pharmaceutically active moieties of the invention are known in the art. Briefly, the antibodies of the invention can be reduced with a reducing agent (e.g., TCEP (tris(2-carboxyethyl) phosphine), purified (e.g., by protein A adsorption or gel filtration), and conjugated with the pharmaceutically active moiety (e.g., by providing a lyophilized peptide to the reduced antibody under conditions that allow for conjugation). After the conjugation reaction, the conjugate can be purified by ion exchange chromatography or hydrophobic interaction chromatography (HIC) with a final purification step of protein A adsorption. In certain embodiments, the antibodies of the invention can be purified prior to being reduced utilizing HIC methods. For more detailed description of the conjugation methods, see, e.g., Examples 3 and 7, and Dennler et al., Antibodies 4:197-224 (2015).

"Homodimerization" as used herein, with respect to the conjugates, refers to an interaction of two identical pharmaceutically active moieties with the antibody. "Homodimer" as used herein, with respect to the conjugate, refers to an antibody coupled to two identical pharmaceutically active moieties.

"Heterodimerization" as used herein, with respect to the conjugates, refers to an interaction of two different pharmaceutically active moieties with the antibody. "Heterodimer" as used herein, with respect to the conjugate, refers to an antibody coupled to two different pharmaceutically active moieties.

Cyclic PYY Peptides $PYY_{3-36}$ is an endogenous hormone secreted by L cells in the distal gut that acts as an agonist of the Y2 receptor to inhibit food intake. Given its role in controlling appetite and food intake as well as its anti-secretory and pro-absorptive effects in the gastrointestinal tract in mammals, $PYY_{3-36}$ can be effective in treating obesity and associated conditions as well as in a number of gastrointestinal disorders. However, the therapeutic utility of $PYY_{3-36}$ itself as a treatment agent is limited by its rapid metabolism and short circulating half-life. Thus, an antibody of the invention can be used as a carrier for a $PYY_{3-36}$, preferably a modified $PYY_{3-36}$, which extends the half-life of the $PYY_{3-36}$ peptide and reduces the metabolism of the peptide in vivo.

In certain embodiments of the invention, the modified $PYY_{3-36}$ peptides are cyclic PYY peptides. The terms "cyclic PYY peptide," "cyclic $PYY_{3-36}$ analog," and "cyclic $PYY_{3-36}$ peptide analog" can be used interchangeably. Examples of cyclic PYY peptides that can be used in the conjugates are described in U.S. Provisional Patent Application No. 62/413,613, filed on Oct. 27, 2016, and U.S. patent application Ser. No. 15/794,231 entitled "Cyclic peptide tyrosine tyrosine compounds as modulators of neuropeptide receptors," filed on the same day as this application, the contents of both applications are hereby incorporated by reference in their entireties.

Examples of conjugates comprising an antibody of the invention and a cyclic PYY peptide are described in U.S. Provisional Patent Application No. 62/413,586, filed on Oct. 27, 2016, and U.S. patent application Ser. No. 15/794,171 entitled "Antibody coupled cyclic peptide tyrosine tyrosine compounds as modulators of neuropeptide Y receptors" filed on the same day as this application, the contents of both applications are hereby incorporated by reference in their entireties. For example, in the cyclic PYY peptides, the N-terminal amino acid residue of the cycle links by way of its α-amino functionality to the linking group, which in turn connects to the side chain residue of the amino acid at position 31 of the NTSC-PYY peptide. Lysine residues can be incorporated at various positions of the $hPYY_{3-36}$ sequence to provide a convenient functional handle for further derivatization. The lysine residues can be modified to be coupled to the monoclonal antibody either directly or indirectly. In an indirect coupling to the monoclonal antibody, the lysine residue can be modified to comprise a linker which will allow for the cyclic PYY peptide to be coupled to the monoclonal antibody. One skilled in the art will recognize that related orthologues could also be effectively employed as such and are contemplated herein.

Oxyntomodulin Peptides

Oxyntomodulin (OXM) is a 37 amino acid peptide secreted from enteroendocrine L cells in the gut. Through its agonist activity at GLP-1 receptor (GLP1R) and glucagon receptor (GCGR), OXM enhances β-cell function, reduces food intake and enhances energy expenditure. Through these complementary mechanisms, OXM-mediated weight loss may be superior, relative to currently marketed GLP1R agonists. OXM can also reduce plasma cholesterol and triglycerides. The half-life of OXM in humans is very short, on the order of minutes (Schjoldager et al., Eur. J. Clin. Invest. 18(5):499-503 (1988)). Thus, an embodiment of the invention relates to a conjugate comprising an antibody of the invention covalently linked to oxyntomodulin to provide dual agonist properties of oxyntomodulin and a protracted half-life sufficient to achieve once-weekly dosing.

Extending the peptide half-life is accomplished by stabilizing the OXM peptide against susceptibility to proteolysis and by reducing plasma clearance. For example, proteolysis by DPP4 was mitigated by substituting the serine at position 2 with aminoisobutyric acid (Aib). The helical topology of the peptide was stabilized by introducing a bifurcated salt bridge from Q20R to S16E and Q24E, and a potential oxidation liability was mitigated by substituting methionine 27 with leucine. The circulating lifetime of the peptide was increased by covalent attachment of a monoclonal antibody (mAb). Such antibody-drug conjugates can exhibit prolonged plasma half-lives by virtue of their size, which can reduce glomerular filtration, and by recycling via the neonatal Fc receptor. A short oligoethylene glycol spacer was interposed between the mAb and the peptide to ensure unhindered access of the peptide to GCGR and GLP1R.

According to embodiments of the invention, an oxyntomodulin conjugate of the present invention contains four characteristics. (A) Dual agonism: the oxyntomodulin conjugates have dual agonism at GLP-1 and glucagon receptors. (B) Receptor balance: the oxyntomodulin conjugates do not have excessive potency bias to either GLP1R or GCGR, as excessive bias to GLP1R could result in a conjugate in which GLP-1 mediated gastrointestinal adverse events occur at escalating exposures prior to GCGR target engagement, and excessive bias to GCGR could mitigate glycemic efficacy. (C) Biodistribution: the oxyntomodulin conjugates have a modest bias toward GLP-1 receptor potency (relative to oxyntomodulin alone), with the objective of achieving target engagement of peripheral GCGR and central, energy intake-modulating, GLP1R at similar exposures. (D) Once-weekly dosing: the oxyntomodulin conjugates are competitive by being capable of being administered to a subject in need thereof once weekly.

Other Therapeutic Peptides

Also provided herein are conjugates comprising other peptides that are capable of being conjugated to the monoclonal antibody platform described herein. The peptides can, for example, be selected from the group consisting of glucagon-like peptide 1 (GLP1), exendin (exenatide), amylin (pramlintide), alpha-melanocyte stimulating hormone (MSH), cocaine- and amphetamine-regulated transcript (CART), neuropeptide Y receptor Y1 (NPY1) antagonists, neuropeptide Y receptor Y5 (NPY5) antagonists, neurotensin S, neuropeptide B, neuropeptide W, ghrelin, bombesin-like receptor 3 (BRS3), galanin, cholecystokinin (CCK), orexin, melanin-concentrating hormone (MCH), oxytocin, and stresscopin.

Glucagon-like peptide-1 (GLP-1) is a 30 amino acid long peptide hormone derived from the tissue-specific post-translational processing of the proglucagon gene. GLP-1 is produced and secreted by intestinal enteroendocrine L-cells and certain neurons upon food consumption. The initial product GLP-1 (1-37) is susceptible to amidation and proteolytic cleavage, which gives rise to two truncated and equipotent biologically active forms, GLP-1 (7-36) amide and GLP-1 (7-37). Endogenous GLP-1 is rapidly degraded through multiple routes, primarily by dipeptidyl peptidase-4 (DPP-4 or DPP-IV), but also neutral endopeptidase 24.11 (NEP 24.11) and through renal clearance, which results in a half-life of approximately 2 minutes. GLP-1 based treatments have been associated with weight loss and lower hypoglycemia risks, which are important in the treatment of type II diabetes.

Exendin (exenatide) is a GLP-1 agonist belonging to a group of incretin mimetics, which have been approved for the treatment of type II diabetes mellitus (T2DM). Exenatide is a synthetic version of exendin-4, a 39-amino acid peptide hormone, which is an insulin secretagogue with glucoregulatory effects. Exendin-4 share extensive homology and function with mammalian GLP-1, but has a therapeutic advantage as it is resistant to degradation by DPP-4 (DPP-IV), which allows for a longer pharmacological half-life. The biological characteristics of exendin-4 led to the consideration for use as a treatment in T2DM.

Amylin (islet amyloid polypeptide (IAPP)) is a 37 amino acid peptide hormone, which is cosecreted with insulin from the pancreatic β-cells. Amylin plays a role in glycemic regulation by slowing gastric emptying and promoting satiety. Amylin (IAPP) is processed from an 89 amino acid peptide. Proiset amyloid polypeptide (proIAPP), is produced in the pancreatic β-cells from the 89 amino acid peptide as a 67 amino acid peptide after a 22 amino acid signal peptide is cleaved. It is believed that impaired processing of proIAPP can lead to the conditions that result in type II diabetes, as the lack of production of amylin (IAPP) can lead to a lack of glycemic control. Pramlintide is an amylinomimetic agent and is at least as potent as human amylin. It is a 37-amino-acid polypeptide and differs in amino acid sequence from human amylin by replacement of amino acids with proline at positions 25 (alanine), 28 (serine), and 29 (serine). The prolines are naturally occurring variations found in rat amylin. As a result of these substitutions, pramlintide is soluble, nonadhesive, and nonaggregating, thereby overcoming a number of the physicochemical liabilities of native human amylin (Janes et al., Diabetes 45(Suppl 2):235A (1996); Young et al., Drug Dev. Res. 37:231-48 (1996b)).

α-Melanocyte-stimulating hormone (α-MSH) is an endogenous peptide hormone and neuropeptide of the melanocortin family. α-MSH is the most important of the melanocyte-stimulating hormones (MSHs) in stimulating melanogenesis, which is a process in mammals responsible for pigmentation of the hair and skin. α-MSH also plays a role in feeding behavior, energy homeostasis, sexual activity, and protection against ischemia and reperfusion injury.

Cocaine- and amphetamine-regulated transcript (CART) is a neuropeptide protein encoded by the CARTPT gene in humans. CART peptides, in particular CART (55-102), seems to have an important function in the regulation of energy homeostasis, as the CART peptides interact with several hypothalamic appetite circuits. CART expression is regulated by peripheral peptide hormones involved in appetite regulation, which includes leptin, cholecystokinin, and ghrelin. CART and cholecystokinin have synergistic effects on appetite regulation. It is believed that CART peptides play a role in anxiety-like behavior, induced by ethanol withdrawal; modulate the locomotor, conditioned place preference and cocaine self-administration effect of psychostimulants; inhibit food intake; and are involved in fear and startile behavior. CART hypoactivity in the hypothalamus is associated with hyperphagia and weight gain, and CART is thought to play a role in the opioid mesolimbic dopamine circuit that modulates natural reward processes.

Neuropeptide Y (NPY) has numerous roles in the body that include, e.g., the control of feeding behaviour, cortical neural activity, heart activity and emotional regulation. NPY has also been implicated in several human diseases including obesity, alcoholism and depression. Furthermore, blockade of the central actions of NPY using anti-NPY antibodies, antisense oligodeoxynucleotides against NPY and NPY receptor antagonists results in a decrease in food intake in energy-deprived animals. In particular, Neuropeptide Y receptor Y5 (NPY5) and Neuropeptide Y receptor Y1 (NPY1) have been shown to stimulate different phases of feeding (*Br J Pharmacol.* 2003 August; 139(8):1433-40). Thus, NPY5 and NPY1 antagonists could be effective in the treatment obesity and other related metabolic diseases.

Neurotensin is a 13 amino acid neuropeptide that is implicated in the regulation of luteinizing hormone and prolactin release and has significant interaction with the dopaminergic system. Neurotensin is distributed throughout the central nervous system with the highest levels being in the hypothalamus, amygdala, and nucleus accumbens. Neurotensin can induce a variety of effects, including analgesia, hypothermia, increased locomoter activity, and is involved in the regulation of dopamine pathways.

Neuropeptide B (NPB) is a short, biologically active peptide, whose precursor is encoded by the NBP gene. NPB can act via two G protein-coupled receptors, called neuropeptide B/W receptors 1 and 2 (NPBWR1 and NPBWR2). It is believed that neuropeptide B is associated with the regulation of feeding, neuroendocrine system, memory, learning, and the afferent pain pathway.

Neuropeptide W (NPW) exists in two forms, consisting of 23 (NPW23) or 30 (NPW30) amino acids. These neuropeptides bind to and can act via the two G-protein couple receptors, NPBWR1 (a.k.a GPR7) and NPBWR2 (a.k.a. GPR8). NPW has been shown to suppress food intake and body weight and to increase both heat production and body temperature, suggesting that NPW functions as an endogenous catabolic signaling molecule.

Ghrelin (a.k.a. ienomorelin (INN)) is a peptide hormone, produced by ghrelinergic cells in the gastrointestinal tract, which functions as a neuropeptide in the central nervous system. Ghrelin plays a role in regulating appetite, regulating the distribution and rate of use of energy, regulating the reward perception in dopamine neurons. Ghrelin is encoded by the GHRL gene and is thought to be produced from the cleavage of the preproghrelin, which is cleaved to produce proghrelin, which is leaved to produce the 28 amino acid ghrelin. Unlike other endogenous peptides, ghrelin is able to cross the blood-brain barrier, which gives exogenously administered ghrelin a unique clinical potential.

Bombesin-like receptor 3 (BRS3) is a G protein-couple receptor that only interacts with known naturally occurring bombesin-related peptides with low affinity, and, as it has no high-affinity ligand, BRS3 is classified as an orphan receptor.

Galanin is a neuropeptide encoding by the GAL gene. Galanin is widely expressed in the brain, spinal cord, and gut of humans as well as other animals. The function of galanin has yet to be fully classified; however, galanin is predominantly involved in the modulation and inhibition of action potentials in neurons. Galanin has been implicated in many biologically diverse functions including, but not limited to, nociception, waking and sleep regulation, cognition, feeding, regulation of mood, and regulation of blood pressure. Galanin is often co-localized with classical neurotransmitters such as acetylcholine, serotonin, and norepinephrine, and also with neuromodulators such as neuropeptide Y, substance P, and vasoactive intestinal peptide.

Cholecystokinin (CCK) is a peptide hormone of the gastrointestinal system responsible for stimulating the digestion of fat and protein. CCK is synthesized and secreted by the enteroendocrine cells in the small intestine and its presence causes the release of digestive enzymes and bile from the pancreas and gallbladder. CCK plays a role in digestion, satiety, and anxiety.

Orexin (a.k.a. hypocretin) is a neuropeptide that regulates arousal, wakefulness, and appetite. There are two types of orexin: orexin A and B (hypocretin-1 and -2), which are 33 and 28 amino acids in length, respectively. The orexin system was primarily believed to be involved with the stimulation of food intake, and in addition to the roles described above, orexins regulate energy expenditure ad modulate visceral function.

Melanin-concentrating hormone (MCH) is a cyclic 19-amino acid orexigenic hypothalamic peptide, which is believed to be involved in the regulation of feeding behavior, mood, sleep-wake cycle, and energy balance. MCH expressing neurons are located within the lateral hypothalamus and zona increta, and despite this restricted distribution, MCH neurons project widely throughout the brain.

Oxytocin is a peptide hormone and neuropeptide normally produced by the paraventricular nucleus of the hypothalamus and released by the posterior pituitary. Oxytocin is believed to play a role in social bonding, sexual reproduction, and during and after childbirth. The oxytocin receptor is a G protein-coupled receptor that requires magnesium and cholesterol and belongs to the rhodopsin-type (class I) group of G protein-coupled receptors.

Human stresscopin (h-SCP) is a 40-amino-acid peptide, that is a member of the corticotrophin releasing hormone (CRH) peptide family. The biological actions of the CRH peptide family are elicited by two 7 transmembrane G-protein coupled receptors, CRH receptor type 1 (CRHR1) and CRH receptor type 2 (CRHR2). Although these receptors contain high sequence homology, the different members of the CRH peptide family express significant differences in their relative binding affinity, degree of receptor activation and selectivity for these two receptors. Unlike many of the CRH family members, h-SCP expresses greater selectivity for the CRHR2 and acts as a mediator that aids in the process of attenuating the initiation and maintenance of physiological stress. In addition to its apparent role in physiological stress, h-SCP has been reported to elicit a number of other physiological actions. It exerts effects on the endocrine, central nervous, cardiovascular, pulmonary, gastrointestinal, renal, skeletal muscle, and inflammatory systems. CRHR2 activity has also been implicated in skeletal muscle wasting disease, such as sarcopenia, motor activity and food intake, participates in a cardioprotective role and expresses bronchorelaxant and anti-inflammatory activity. Furthermore, stresscopin mimics have been identified that are useful for treating medical indications mediated by corticotrophin releasing hormone receptor 2 activity see, e.g., U.S. Patent App. No.: 20100130424.

Half-Life Extending Moieties

In addition to the antibody of the present invention or an antigen binding fragment thereof, the conjugates of the invention can incorporate one or more other moieties for extending the half-life of the pharmaceutical active moiety, for example via covalent interaction. Exemplary other half-life extending moieties include, but not limited to, albumin, albumin variants, albumin-binding proteins and/or domains, transferrin and fragments and analogues thereof. Additional half-life extending moieties that can be incorporated into the conjugates of the invention include, for example, polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties can be direct fusions with the protein scaffold coding sequences and can be generated by standard cloning and expression techniques. Alternatively, well known chemical coupling methods can be used to attach the moieties to recombinantly and chemically produced conjugates of the invention.

A pegyl moiety can, for example, be added to the peptide molecules of the invention by incorporating a cysteine residue to the C-terminus of the molecule and attaching a pegyl group to the cysteine using well known methods.

Peptide molecules of the invention incorporating additional moieties can be compared for functionality by several well-known assays. For example, the biological or pharmacokinetic activities of a therapeutic peptide of interest, alone or in a conjugate according to the invention, can be assayed using known in vitro or in vivo assays and compared.

Pharmaceutical Compositions

In another general aspect, the invention relates to a pharmaceutical composition, comprising the conjugates of the invention and a pharmaceutically acceptable carrier. The term "pharmaceutical composition" as used herein means a product comprising a conjugate of the invention together with a pharmaceutically acceptable carrier. Conjugates of the invention and compositions comprising them are also useful in the manufacture of a medicament for therapeutic applications mentioned herein.

As used herein, the term "carrier" refers to any excipient, diluent, filler, salt, buffer, stabilizer, solubilizer, oil, lipid, lipid containing vesicle, microsphere, liposomal encapsulation, or other material well known in the art for use in pharmaceutical formulations. It will be understood that the characteristics of the carrier, excipient or diluent will depend on the route of administration for a particular application. As used herein, the term "pharmaceutically acceptable carrier" refers to a non-toxic material that does not interfere with the effectiveness of a composition according to the invention or the biological activity of a composition according to the invention. According to particular embodiments, in view of the present disclosure, any pharmaceutically acceptable carrier suitable for use in an antibody pharmaceutical composition can be used in the invention.

Pharmaceutically acceptable acidic/anionic salts for use in the invention include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

Pharmaceutically acceptable basic/cationic salts include, and are not limited to aluminum, 2-amino-2-hydroxymethyl-propane-1,3-diol (also known as tris(hydroxymethyl)aminomethane, tromethane or "TRIS"), ammonia, benzathine, t-butylamine, calcium, chloroprocaine, choline, cyclohexylamine, diethanolamine, ethylenediamine, lithium, L-lysine, magnesium, meglumine, N-methyl-D-glucamine, piperidine, potassium, procaine, quinine, sodium, triethanolamine, or zinc.

In some embodiments of the invention, pharmaceutical formulations are provided comprising the conjugates of the invention in an amount from about 0.001 mg/ml to about 100 mg/ml, from about 0.01 mg/ml to about 50 mg/ml, or from about 0.1 mg/ml to about 25 mg/ml. The pharmaceutical formulation may have a pH from about 3.0 to about 10, for example from about 3 to about 7, or from about 5 to about 9. The formulation may further comprise at least one ingredient selected from the group consisting of a buffer system, preservative(s), tonicity agent(s), chelating agent(s), stabilizer(s) and surfactant(s).

The formulation of pharmaceutically active ingredients with pharmaceutically acceptable carriers is known in the art, e.g., Remington: The Science and Practice of Pharmacy (e.g. 21st edition (2005), and any later editions). Non-limiting examples of additional ingredients include: buffers, diluents, solvents, tonicity regulating agents, preservatives, stabilizers, and chelating agents. One or more pharmaceutically acceptable carrier may be used in formulating the pharmaceutical compositions of the invention.

In one embodiment of the invention, the pharmaceutical composition is a liquid formulation. A preferred example of a liquid formulation is an aqueous formulation, i.e., a formulation comprising water. The liquid formulation may comprise a solution, a suspension, an emulsion, a microemulsion, a gel, and the like. An aqueous formulation typically comprises at least 50% w/w water, or at least 60%, 70%, 75%, 80%, 85%, 90%, or at least 95% w/w of water.

In one embodiment, the pharmaceutical composition may be formulated as an injectable which can be injected, for example, via a syringe or an infusion pump. The injection may be delivered subcutaneously, intramuscularly, intraperitoneally, or intravenously, for example.

In another embodiment, the pharmaceutical composition is a solid formulation, e.g., a freeze-dried or spray-dried composition, which may be used as is, or whereto the physician or the patient adds solvents, and/or diluents prior to use. Solid dosage forms may include tablets, such as compressed tablets, and/or coated tablets, and capsules (e.g., hard or soft gelatin capsules). The pharmaceutical composition may also be in the form of sachets, dragees, powders, granules, lozenges, or powders for reconstitution, for example.

The dosage forms may be immediate release, in which case they may comprise a water-soluble or dispersible carrier, or they may be delayed release, sustained release, or modified release, in which case they may comprise water-insoluble polymers that regulate the rate of dissolution of the dosage form in the gastrointestinal tract.

In other embodiments, the pharmaceutical composition may be delivered intranasally, intrabuccally, or sublingually.

The pH in an aqueous formulation can be between pH 3 and pH 10. In one embodiment of the invention, the pH of the formulation is from about 7.0 to about 9.5. In another embodiment of the invention, the pH of the formulation is from about 3.0 to about 7.0.

In another embodiment of the invention, the pharmaceutical composition comprises a buffer. Non-limiting examples of buffers include: arginine, aspartic acid, bicine, citrate, disodium hydrogen phosphate, fumaric acid, glycine, glycylglycine, histidine, lysine, maleic acid, malic acid, sodium acetate, sodium carbonate, sodium dihydrogen phosphate, sodium phosphate, succinate, tartaric acid, tricine, and tris(hydroxymethyl)-aminomethane, and mixtures thereof. The buffer may be present individually or in the aggregate, in a concentration from about 0.01 mg/ml to about 50 mg/ml, for example from about 0.1 mg/ml to about 20 mg/ml. Pharmaceutical compositions comprising each one of these specific buffers constitute alternative embodiments of the invention.

In another embodiment of the invention, the pharmaceutical composition comprises a preservative. Non-limiting examples of preservatives include: benzethonium chloride, benzoic acid, benzyl alcohol, bronopol, butyl 4-hydroxybenzoate, chlorobutanol, chlorocresol, chlorohexidine, chlorphenesin, o-cresol, m-cresol, p-cresol, ethyl 4-hydroxybenzoate, imidurea, methyl 4-hydroxybenzoate, phenol, 2-phenoxyethanol, 2-phenylethanol, propyl 4-hydroxybenzoate, sodium dehydroacetate, thiomerosal, and mixtures thereof. The preservative may be present individually or in the aggregate, in a concentration from about 0.01 mg/ml to about 50 mg/ml, for example from about 0.1 mg/ml to about 20 mg/ml. Pharmaceutical compositions comprising each one of these specific preservatives constitute alternative embodiments of the invention.

In another embodiment of the invention, the pharmaceutical composition comprises an isotonic agent. Non-limiting examples of the embodiment include a salt (such as sodium chloride), an amino acid (such as glycine, histidine, arginine, lysine, isoleucine, aspartic acid, tryptophan, and threonine), an alditol (such as glycerol, 1,2-propanediol propyleneglycol), 1,3-propanediol, and 1,3-butanediol), polyethyleneglycol (e.g. PEG400), and mixtures thereof. Another example of an isotonic agent includes a sugar. Non-limiting examples of sugars may be mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alpha and beta-HPCD, soluble starch, hydroxyethyl starch, and sodium carboxymethylcellulose. Another example of an isotonic agent is a sugar alcohol, wherein the term "sugar alcohol" is defined as a C(4-8) hydrocarbon having at least one —OH group. Non-limiting examples of sugar alcohols include mannitol, sorbitol, inositol, galactitol, dulcitol, xylitol, and arabitol. Pharmaceutical compositions comprising each isotonic agent listed in this paragraph constitute alternative embodiments of the invention. The isotonic agent may be present individually or in the aggregate, in a concentration from about 0.01 mg/ml to about 50 mg/ml, for example from about 0.1 mg/ml to about 20 mg/ml. Pharmaceutical compositions comprising each one of these specific isotonic agents constitute alternative embodiments of the invention.

In another embodiment of the invention, the pharmaceutical composition comprises a chelating agent. Non-limiting examples of chelating agents include citric acid, aspartic acid, salts of ethylenediaminetetraacetic acid (EDTA), and mixtures thereof. The chelating agent may be present individually or in the aggregate, in a concentration from about 0.01 mg/ml to about 50 mg/ml, for example from about 0.1 mg/ml to about 20 mg/ml. Pharmaceutical compositions comprising each one of these specific chelating agents constitute alternative embodiments of the invention.

In another embodiment of the invention, the pharmaceutical composition comprises a stabilizer. Non-limiting examples of stabilizers include one or more aggregation inhibitors, one or more oxidation inhibitors, one or more surfactants, and/or one or more protease inhibitors.

In another embodiment of the invention, the pharmaceutical composition comprises a stabilizer, wherein said stabilizer is carboxy-/hydroxycellulose and derivates thereof (such as HPC, HPC-SL, HPC-L and HPMC), cyclodextrins, 2-methylthioethanol, polyethylene glycol (such as PEG 3350), polyvinyl alcohol (PVA), polyvinyl pyrrolidone, salts (such as sodium chloride), sulphur-containing substances such as monothioglycerol), or thioglycolic acid. The stabilizer may be present individually or in the aggregate, in a concentration from about 0.01 mg/ml to about 50 mg/ml, for example from about 0.1 mg/ml to about 20 mg/ml. Pharmaceutical compositions comprising each one of these specific stabilizers constitute alternative embodiments of the invention.

In further embodiments of the invention, the pharmaceutical composition comprises one or more surfactants, preferably a surfactant, at least one surfactant, or two different surfactants. The term "surfactant" refers to any molecules or ions that are comprised of a water-soluble (hydrophilic) part, and a fat-soluble (lipophilic) part. The surfactant may, for example, be selected from the group consisting of anionic surfactants, cationic surfactants, nonionic surfactants, and/or zwitterionic surfactants. The surfactant may be present individually or in the aggregate, in a concentration from about 0.1 mg/ml to about 20 mg/ml. Pharmaceutical compositions comprising each one of these specific surfactants constitute alternative embodiments of the invention.

In a further embodiment of the invention, the pharmaceutical composition comprises one or more protease inhibitors, such as, e.g., EDTA (ethylenediamine tetraacetic acid), and/or benzamidine hydrochloric acid (HCl). The protease inhibitor may be present individually or in the aggregate, in a concentration from about 0.1 mg/ml to about 20 mg/ml. Pharmaceutical compositions comprising each one of these specific protease inhibitors constitute alternative embodiments of the invention.

The pharmaceutical composition of the invention may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present. The amino acid base may be present individually or in the combination with other amino acid bases, in a concentration from about 0.01 mg/ml to about 50 mg/ml, for example from about 0.1 mg/ml to about 20 mg/ml. Pharmaceutical compositions comprising each one of these specific amino acid bases constitute alternative embodiments of the invention.

It is also apparent to one skilled in the art that the therapeutically effective dose for conjugates of the present invention or a pharmaceutical composition thereof will vary according to the desired effect. Therefore, optimal dosages to be administered may be readily determined by one skilled in the art and will vary with the particular conjugate used, the mode of administration, the strength of the preparation, and the advancement of the disease condition. In addition, factors associated with the particular subject being treated, including subject age, weight, diet and time of administration, will result in the need to adjust the dose to an appropriate therapeutic level.

For all indications, the conjugates of the invention are preferably administered peripherally at a dose of about 1 μg to about 5 mg per day in single or divided doses (e.g., a single dose can be divided into 2, 3, 4, 5, 6, 7, 8, 9, or 10 subdoses), or at about 0.01 μg/kg to about 500 μg/kg per dose, more preferably about 0.05 μg/kg to about 250 μg/kg, most preferably below about 50 μg/kg. Dosages in these ranges will vary with the potency of each agonist, of course, and are readily determined by one of skill in the art. The above dosages are thus exemplary of the average case. There can, of course, be individual instances where higher or lower dosage ranges are merited, and such are within the scope of this invention.

In certain embodiments, the conjugates of the invention are administered at a dose of about 1 μg to about 5 mg, or at a dose of about 0.01 μg/kg to about 500 μg/kg, more preferably at a dose of about 0.05 μg/kg to about 250 μg/kg, most preferably at a dose below about 50 μg/kg with a dose of a second therapeutic agent (e.g., liraglutide) at a dose of about 1 μg to about 5 mg, or at a dose of about 0.01 μg/kg to about 500 μg/kg, more preferably at a dose of about 0.05 μg/kg to about 250 μg/kg, most preferably at a dose below about 50 μg/kg.

The pharmaceutically-acceptable salts of the conjugates of the invention include the conventional non-toxic salts or the quaternary ammonium salts which are formed from inorganic or organic acids or bases. Examples of such acid addition salts include acetate, adipate, benzoate, benzenesulfonate, citrate, camphorate, dodecylsulfate, hydrochloride, hydrobromide, lactate, maleate, methanesulfonate, nitrate, oxalate, pivalate, propionate, succinate, sulfate and tartrate. Base salts include ammonium salts, alkali metal salts such as sodium and potassium salts, alkaline earth metal salts such as calcium and magnesium salts, salts with organic bases such as dicyclohexylamino salts and salts with amino acids such as arginine. Also, the basic nitrogen-containing groups may be quaternized with, for example, alkyl halides.

The pharmaceutical compositions of the invention may be administered by any means that accomplish their intended purpose. Examples include administration by parenteral, subcutaneous, intravenous, intramuscular, intraperitoneal, transdermal, buccal or ocular routes. Administration may be by the oral route. Suitable formulations for parenteral administration include aqueous solutions of the active conjugates in water-soluble form, for example, water-soluble salts, acidic solutions, alkaline solutions, dextrose-water solutions, isotonic carbohydrate solutions and cyclodextrin inclusion complexes.

The present invention also encompasses a method of making a pharmaceutical composition comprising mixing a pharmaceutically acceptable carrier with any of the conjugates of the present invention. Additionally, the present invention includes pharmaceutical compositions made by mixing one or more pharmaceutically acceptable carriers with any of the conjugates of the present invention.

Furthermore, the conjugates of the present invention may have one or more polymorph or amorphous crystalline forms and as such are intended to be included in the scope of the invention. In addition, the conjugates may form solvates, for example with water (i.e., hydrates) or common organic solvents. As used herein, the term "solvate" means a physical association of the conjugates of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like.

It is intended that the present invention include within its scope polymorphs and solvates of the conjugates of the present invention. Thus, in the methods of treatment of the present invention, the term "administering" shall encompass the means for treating, ameliorating or preventing a syndrome, disorder or disease described herein with the conjugates of the present invention or a polymorph or solvate thereof, which would obviously be included within the scope of the invention albeit not specifically disclosed.

In another embodiment, the invention relates to the conjugates of the invention for use as a medicament.

The present invention includes within its scope prodrugs of the conjugates of this invention. In general, such prodrugs will be functional derivatives of the conjugates which are readily convertible in vivo into the required conjugate. Thus, in the methods of treatment of the present invention, the term "administering" shall encompass the treatment of the various disorders described with the conjugate specifically disclosed or with a conjugate which may not be specifically disclosed, but which converts to the specified conjugate in vivo after administration to the patient. Conventional procedures for the selection and preparation of suitable prodrug derivatives are described, for example, in "Design of Prodrugs", Ed. H. Bundgaard, Elsevier, 1985.

Furthermore, it is intended that within the scope of the present invention, any element, in particular when mentioned in relation to the conjugates of the invention, shall comprise all isotopes and isotopic mixtures of said element, either naturally occurring or synthetically produced, either with natural abundance or in an isotopically enriched form. For example, a reference to hydrogen includes within its scope $^1H$, $^2H$ (D), and $^3H$ (T). Similarly, references to carbon and oxygen include within their scope respectively 12C, $^{13}C$ and $^{14}C$ and $^{16}O$ and $^{18}O$. The isotopes may be radioactive or non-radioactive. Radiolabelled conjugates of the invention may comprise a radioactive isotope selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Some conjugates of the present invention may exist as atropisomers. Atropisomers are stereoisomers resulting from hindered rotation about single bonds where the steric strain barrier to rotation is high enough to allow for the isolation of the conformers. It is to be understood that all such conformers and mixtures thereof are encompassed within the scope of the present invention.

Where the conjugates according to this invention have at least one stereo center, they may accordingly exist as enantiomers or diastereomers. It is to be understood that all such isomers and mixtures thereof are encompassed within the scope of the present invention.

Where the processes for the preparation of the conjugates according to the invention give rise to mixture of stereoisomers, these isomers may be separated by conventional techniques such as preparative chromatography. The conjugates may be prepared in racemic form, or individual enantiomers may be prepared either by enantiospecific synthesis or by resolution. The conjugates may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The conjugates may also be resolved by formation of diastereomeric esters or amides, followed by chromatographic separation and removal of the chiral auxiliary. Alternatively, the conjugates may be resolved using a chiral column via high performance liquid chromatography (HPLC) or SFC. In some instances rotamers of conjugates may exist which are observable by 1H NMR leading to complex multiplets and peak integration in the 1H NMR spectrum.

During any of the processes for preparation of the conjugates of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, each of which is herein incorporated by reference in its entirety for all purposes. The protecting groups may be removed at a convenient subsequent stage using methods known from the art.

Methods of Use

The present invention also provides a method for preventing, treating, delaying the onset of, or ameliorating a disorder, disease, or condition or any one or more symptoms of said disorder, disease, or condition in a subject in need thereof, the method comprising administering to the subject in need thereof an effective amount of a conjugate or pharmaceutical composition of the invention.

According to particular embodiments, the disease disorder, or condition can be any disease, disorder, or condition that could be treated with a peptide or compound capable of being coupled to the monoclonal antibody platform of the present invention. In certain embodiments, the disease, disorder or condition is selected from the group consisting of obesity, type I or II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and/or eczema.

According to particular embodiments, a therapeutically effective amount refers to the amount of therapy which is sufficient to achieve one, two, three, four, or more of the following effects: (i) reduce or ameliorate the severity of the disease, disorder or condition to be treated or a symptom associated therewith; (ii) reduce the duration of the disease, disorder or condition to be treated, or a symptom associated therewith; (iii) prevent the progression of the disease, disorder or condition to be treated, or a symptom associated therewith; (iv) cause regression of the disease, disorder or condition to be treated, or a symptom associated therewith; (v) prevent the development or onset of the disease, disorder or condition to be treated, or a symptom associated therewith; (vi) prevent the recurrence of the disease, disorder or condition to be treated, or a symptom associated therewith; (vii) reduce hospitalization of a subject having the disease, disorder or condition to be treated, or a symptom associated therewith; (viii) reduce hospitalization length of a subject having the disease, disorder or condition to be treated, or a symptom associated therewith; (ix) increase the survival of a subject with the disease, disorder or condition to be treated, or a symptom associated therewith; (xi) inhibit or reduce the disease, disorder or condition to be treated, or a symptom associated therewith in a subject; and/or (xii) enhance or improve the prophylactic or therapeutic effect(s) of another therapy.

The therapeutically effective amount or dosage can vary according to various factors, such as the disease, disorder or condition to be treated, the means of administration, the target site, the physiological state of the subject (including, e.g., age, body weight, health), whether the subject is a human or an animal, other medications administered, and whether the treatment is prophylactic or therapeutic. Treatment dosages are optimally titrated to optimize safety and efficacy.

As used herein, the terms "treat," "treating," and "treatment" are all intended to refer to an amelioration or reversal of at least one measurable physical parameter related the disease, disorder, or condition, which is not necessarily discernible in the subject, but can be discernible in the subject. The terms "treat," "treating," and "treatment," can also refer to causing regression, preventing the progression, or at least slowing down the progression of the disease, disorder, or condition. In a particular embodiment, "treat," "treating," and "treatment" refer to an alleviation, prevention of the development or onset, or reduction in the duration of one or more symptoms associated with the disease, disorder, or condition. In a particular embodiment, "treat," "treating," and "treatment" refer to prevention of the recurrence of the disease, disorder, or condition. In a particular embodiment, "treat," "treating," and "treatment" refer to an increase in the survival of a subject having the disease, disorder, or condition. In a particular embodiment, "treat," "treating," and "treatment" refer to elimination of the disease, disorder, or condition in the subject.

In one embodiment, the invention provides a method for preventing, treating, delaying the onset of, or ameliorating obesity, or any one or more symptoms of obesity in a subject in need thereof, the method comprising administering to the subject in need thereof an effective amount of a conjugate or pharmaceutical composition of the invention. In some embodiments, the body weight of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to the body weight of a subject prior to administration of any of the conjugates, pharmaceutical compositions, forms, or medicaments of the invention described herein, or compared to control subjects not receiving any of the conjugates, compositions, forms, medicaments, or combinations of the invention described herein.

In some embodiments, the reduction in body weight is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of preventing, treating, delaying the onset of, or ameliorating a syndrome, disorder or disease, or any one or more symptoms of said syndrome, disorder, or disease in a subject in need thereof, wherein said syndrome, disorder or disease is selected from the group consisting of obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic steatohepatitis (NASH), renal disease, and eczema, comprising administering to the subject in need thereof an effective amount of a conjugate or pharmaceutical composition of the invention.

As used herein, metabolic syndrome refers to a subject having any one or more of the following: high blood sugar (e.g., high fasting blood sugar), high blood pressure, abnormal cholesterol levels (e.g., low HDL levels), abnormal triglyceride levels (e.g., high triglycerides), a large waistline (i.e., waist circumference), increased fat in the abdominal area, insulin resistance, glucose intolerance, elevated C-reactive protein levels (i.e., a proinflammatory state), and increased plasma plasminogen activator inhibitor-1 and fibrinogen levels (i.e., a prothrombotic state).

The present invention provides a method of reducing food intake in a subject in need thereof, the method comprising administering to the subject in need thereof an effective amount of a conjugate or pharmaceutical composition of the invention. In some embodiments, food intake of a subject is reduced, for example, by between about 0.01% to about 0.1%, between about 0.1% to about 0.5%, between about 0.5% to about 1%, between about 1% to about 5%, between about 2% to about 3%, between about 5% to about 10%, between about 10% to about 15%, between about 15% to about 20%, between about 20% to about 25%, between about 25% to about 30%, between about 30% to about 35%, between about 35% to about 40%, between about 40% to about 45%, or between about 45% to about 50%, relative to food intake of a subject prior to administration of any of the conjugates, compositions, forms, medicaments, or combinations of the invention described herein, or compared to control subjects not receiving any of the conjugates, compositions, forms, medicaments, or combinations of the invention described herein.

In some embodiments, the reduction in food intake is maintained for about 1 week, for about 2 weeks, for about 3 weeks, for about 1 month, for about 2 months, for about 3 months, for about 4 months, for about 5 months, for about 6 months, for about 7 months, for about 8 months, for about 9 months, for about 10 months, for about 11 months, for about 1 year, for about 1.5 years, for about 2 years, for about 2.5 years, for about 3 years, for about 3.5 years, for about 4 years, for about 4.5 years, for about 5 years, for about 6 years, for about 7 years, for about 8 years, for about 9 years, for about 10 years, for about 15 years, or for about 20 years, for example.

The present invention provides a method of reducing glycated hemoglobin (A1C) in a subject in need thereof, the method comprising administering to the subject in need thereof an effective amount of a conjugate or pharmaceutical composition of the invention. In some embodiments, A1C of a subject is reduced, for example, by between about 0.001% and about 0.01%, between about 0.01% and about 0.1%, between about 0.1% and about 0.2%, between about 0.2% and about 0.3%, between about 0.3% and about 0.4%, between about 0.4% and about 0.5%, between about 0.5% and about 1%, between about 1% and about 1.5%, between about 1.5% and about 2%, between about 2% and about 2.5%, between about 2.5% and about 3%, between about 3% and about 4%, between about 4% and about 5%, between about 5% and about 6%, between about 6% and about 7%, between about 7% and about 8%, between about 8% and about 9%, or between about 9% and about 10% relative to the A1C of a subject prior to administration of any of the conjugates, compositions, forms, medicaments, or combinations of the invention described herein, or compared to control subjects not receiving any of the conjugates, compositions, forms, medicaments, or combinations of the invention described herein.

In other embodiments, methods are provided for reducing fasting blood glucose levels in a subject in need thereof, the methods comprising administering to the subject in need thereof an effective amount of a conjugate or pharmaceutical composition of the invention. Fasting blood glucose levels may be reduced to less than about 140 to about 150 mg/dL, less than about 140 to about 130 mg/dL, less than about 130 to about 120 mg/dL, less than about 120 to about 110 mg/dL, less than about 110 to about 100 mg/dL, less than about 100 to about 90 mg/dL, or less than about 90 to about 80 mg/dL, relative to the fasting blood glucose levels of a subject prior to administration of any of the conjugates, compositions, forms, medicaments, or combinations of the invention described herein, or compared to control subjects not receiving any of the conjugates, compositions, forms, medicaments, or combinations of the invention described herein.

The present invention provides a method of modulating Y2 receptor activity in a subject in need thereof, the method comprising administering to the subject in need thereof an effective amount of a conjugate or pharmaceutical composition of the invention. As used herein, "modulating" refers to increasing or decreasing receptor activity.

In some embodiments, an effective amount of a conjugate of the invention or a form, composition or medicament thereof is administered to a subject in need thereof once daily, twice daily, three times daily, four times daily, five times daily, six times daily, seven times daily, or eight times daily. In other embodiments, an effective amount of a conjugate of the invention or a form, composition or medicament thereof is administered to a subject in need thereof once every other day, once per week, twice per week, three times per week, four times per week, five times per week, six times per week, two times per month, three times per month, or four times per month.

Another embodiment of the invention comprises a method of preventing, treating, delaying the onset of, or ameliorating a disease, disorder or syndrome, or one or more symptoms of any of said diseases, disorders, or syndromes in a subject in need thereof, the method comprising administering to the subject in need thereof an effective amount of a conjugate or pharmaceutical composition of the invention in a combination therapy. In certain embodiments, the combination therapy is a second therapeutic agent. In certain embodiments, the combination therapy is a surgical therapy.

As used herein, the term "in combination," in the context of the administration of two or more therapies to a subject, refers to the use of more than one therapy.

As used herein, combination therapy refers to administering to a subject in need thereof one or more additional therapeutic agents, or one or more surgical therapies, concurrently with an effective amount of a conjugate of the invention or a form, composition or medicament thereof. In some embodiments, the one or more additional therapeutic agents or surgical therapies can be administered on the same day as an effective amount of a conjugate of the invention, and in other embodiments, the one or more additional therapeutic agents or surgical therapies may be administered in the same week or the same month as an effective amount of a conjugate of the invention.

In certain embodiments, wherein the disease or disorder is selected from the group consisting of obesity, type II diabetes, metabolic syndrome, insulin resistance and dyslipidemia, the second therapeutic agent can be an antidiabetic agent. In certain embodiments, the antidiabetic agent can be a glucagon-like peptide-1 (GLP-1) receptor modulator.

The present invention also contemplates preventing, treating, delaying the onset of, or ameliorating any of the diseases, disorders, syndromes, or symptoms described herein in a subject in need thereof with a combination therapy that comprises administering to the subject in need thereof an effective amount of a conjugate or pharmaceutical composition of the invention, in combination with any one or more of the following therapeutic agents: a dipeptidyl peptidase-4 (DPP-4) inhibitor (e.g., sitagliptin, saxagliptin, linagliptin, alogliptin, etc.); a GLP-1 receptor agonist (e.g., short-acting GLP-1 receptor agonists such as exenatide and lixisenatide; intermediate-acting GLP-1 receptor agonists such as liraglutide; long-acting GLP-1 receptor agonists such as exenatide extended-release, albiglutide, dulaglutide); a sodium-glucose co-transporter-2 (SGLT-2) inhibitors (e.g., canaglifozin, dapaglifozin, empaglifozin, etc.); bile acid sequestrants (e.g., colesevelam, etc.); dopamine receptor agonists (e.g., bromocriptine quick-release); biguanides (e.g., metformin, etc.); insulin; oxyntomodulin; sulfonylureas (e.g., chlorpropamide, glimepiride, glipizide, glyburide, glibenclamide, glibornuride, glisoxepide, glyclopyramide, tolazamide, tolbutamide, acetohexamide, carbutamide, etc.); and thiazolidinediones (e.g; pioglitazone, rosiglitazone, lobeglitazone, ciglitazone, darglitazone, englitazone, netoglitazone, rivoglitazone, troglitazone, etc.). In some embodiments, the dose of the additional therapeutic agent(s) is reduced when given in combination with a conjugate of the invention. In some embodiments, when used in combination with a conjugate of the invention, the additional therapeutic agent(s) may be used in lower doses than when each is used singly.

In certain embodiments, wherein the disease or disorder is selected from the group consisting of obesity, type I or type II diabetes, metabolic syndrome (i.e., Syndrome X), insulin resistance, impaired glucose tolerance (e.g., glucose intolerance), hyperglycemia, hyperinsulinemia, hypertriglyceridemia, hypoglycemia due to congenital hyperinsulinism (CHI), dyslipidemia, atherosclerosis, diabetic nephropathy, and other cardiovascular risk factors such as hypertension and cardiovascular risk factors related to unmanaged cholesterol and/or lipid levels, osteoporosis, inflammation, non-alcoholic fatty liver disease (NAFLD), non-alcoholic steatohepatitis (NASH), renal disease, and eczema, the second therapeutic agent can be liraglutide.

The present invention contemplates preventing, treating, delaying the onset of, or ameliorating any of the diseases, disorders, syndromes, or symptoms described herein in a subject in need thereof, with a combination therapy that comprises administering to the subject in need thereof an effective amount of a conjugate or pharmaceutical composition of the invention in combination with a surgical therapy. In certain embodiments, the surgical therapy can be bariatric surgery (e.g., gastric bypass surgery, such as Roux-en-Y gastric bypass surgery; sleeve gastrectomy; adjustable gastric band surgery; biliopancreatic diversion with duodenal switch; intragastric balloon; gastric plication; and combinations thereof).

In embodiments in which the one or more additional therapeutic agents is administered on the same day as an effective amount of a conjugate of the invention, the conjugate of the invention may be administered prior to, after, or simultaneously with the additional therapeutic agent. The use of the term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

Embodiments

The invention provides also the following non-limiting embodiments.

Embodiment 1 is an isolated antibody or antigen binding fragment thereof comprising a light chain variable region having completely human Ig germline V gene sequences, and a heavy chain variable region having completely human Ig germline V gene sequences except HCDR3 having the amino acid sequence of SEQ ID NO:18, wherein the antibody or antigen binding fragment thereof does not specifically bind to any human antigen in vivo.

Embodiment 2 is the isolated monoclonal antibody or antigen-binding fragment thereof of embodiment 1, wherein the isolated monoclonal antibody or antigen-binding fragment thereof comprises a heavy chain complementarity determining region 1 (HCDR1), HCDR2, HCDR3, and a light chain complementarity determining region 1 (LCDR1), LCDR2, and LCDR3, having the polypeptide sequences of SEQ ID NO: 16, 17, 18, 19, 20, and 21, respectively Embodiment 3 is the isolated monoclonal antibody or antigen-binding fragment thereof of embodiment 2, wherein the isolated monoclonal antibody comprises a heavy chain variable domain (VH) having the polypeptide sequence of SEQ ID NO:12, and a light chain variable domain (VL) having the polypeptide sequence of SEQ ID NO:14.

Embodiment 4 is the isolated monoclonal antibody of any one of embodiments 1-3, further comprising a Fc portion.

Embodiment 5 is the isolated monoclonal antibody of embodiment 4, wherein the Fc portion further comprises a Fc region derived from human IgG4 Fc region.

Embodiment 6 is the isolated monoclonal antibody of embodiment 5, wherein the human IgG4 Fc region has substitutions that eliminate effector function.

Embodiment 7 is the isolated monoclonal antibody of embodiment 6, wherein the monoclonal antibody further comprises a modified human IgG4 Fc region containing at least one substitution selected from the group consisting of a proline for glutamate at residue 233, an alanine or valine for phenylalanine at residue 234, an alanine or glutamate for leucine at residue 235, an alanine for asparagine at residue 297.

Embodiment 8 is the isolated monoclonal antibody of embodiment 6 or 7, wherein the human IgG4 Fc region comprises a substitution of a serine to proline at position 228.

Embodiment 9 is the isolated monoclonal antibody of any one of embodiments 4-8, comprising a heavy chain (HC) having the polypeptide sequence of SEQ ID NO:13, and a light chain (LC) having the polypeptide sequence of SEQ ID NO:15.

Embodiment 10 is an isolated nucleic acid encoding the monoclonal antibody or antigen binding fragment thereof of any one of embodiments 1-9.

Embodiment 11 is a vector comprising the isolated nucleic acid of embodiment 10.

Embodiment 12 is a host cell comprising the vector of embodiment 11.

Embodiment 13 is a method of producing an isolated monoclonal antibody or antigen binding fragment thereof, the method comprising culturing the host cell of embodiment 12 under conditions to produce the monoclonal antibody or antigen binding fragment thereof, and recovering the antibody or antigen-binding fragment thereof from the cell or culture.

Embodiment 14 is the isolated monoclonal antibody or antigen-binding fragment thereof of any one of embodiments 1-9, further comprising at least one pharmacologically active moiety conjugated thereto.

Embodiment 15 is the isolated monoclonal antibody or antigen-binding fragment thereof of embodiment 14, wherein the pharmacologically active moiety is a therapeutic peptide.

Embodiment 16 is the isolated monoclonal antibody or antigen-binding fragment thereof of embodiment 15, wherein the therapeutic peptide is conjugated at the cysteine residue of SEQ ID NO:18.

Embodiment 17 is the isolated monoclonal antibody or antigen-binding fragment thereof of embodiment 15 or 16, wherein the therapeutic peptide is conjugated to the antibody or antigen-binding fragment thereof via a linker.

Embodiment 18 is the isolated monoclonal antibody or antigen-binding fragment thereof of embodiment 17, wherein the linker comprises a peptide linker, a hydrocarbon linker, a polyethylene glycol (PEG) linker, a polypropylene glycol (PPG) linker, a polysaccharide linker, a polyester linker, or a hybrid linker consisting of PEG and an embedded heterocycle.

Embodiment 19 is the isolated monoclonal antibody or antigen-binding fragment thereof of any one of embodiments 15-18, wherein the therapeutic peptide is selected from the group consisting of oxyntomodulin, glucagon-like peptide 1 (GLP1), peptide tyrosine tyrosine (PYY), exendin (exenatide), amylin (pramlintide), alpha-melanocyte stimulating hormone (MSH), cocaine- and amphetamine-regulated transcript (CART), neuropeptide Y receptor Y1 (NPY1) antagonists, neuropeptide Y receptor Y5 (NPY5) antagonists, neurotensin S, neuropeptide B, neuropeptide W, ghrelin, bombesin-like receptor 3 (BRS3), galanin, cholecystokinin (CCK), orexin, melanin-concentrating hormone (MCH), oxytocin, and stresscopin.

Embodiment 20 is the isolated monoclonal antibody or antigen binding fragment thereof of embodiment 19, wherein the therapeutic peptide is oxyntomodulin comprising the polypeptide sequence of SEQ ID NO:24.

Figure 11:
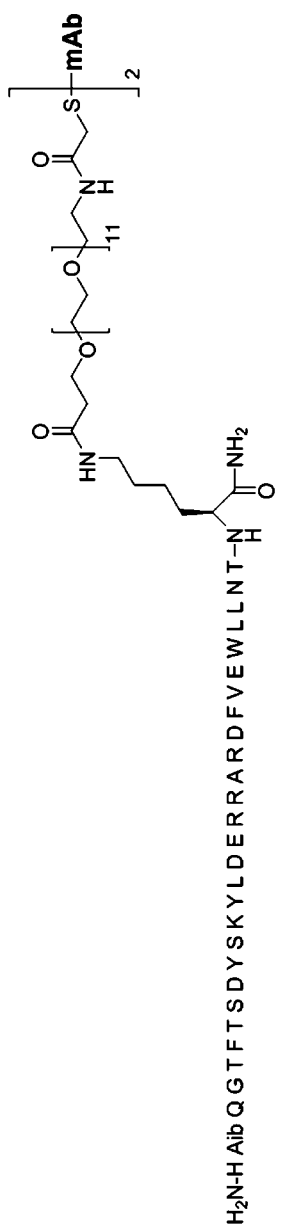
FIG. 11: Shows the structure of compound 2 (SEQ ID NO:27).

Embodiment 21 is a conjugate comprising a monoclonal antibody or antigen binding fragment thereof coupled to an oxyntomodulin therapeutic peptide, wherein the conjugate has the structure of SEQ ID NO:27 as shown in FIG. 11, wherein mAb represents a monoclonal antibody or antigen binding fragment thereof according to any one of embodiments 1-9, and]$_2$ represents that 1 or 2 of the oxyntomodulin therapeutic peptide are covalently conjugated to the mAb.

Embodiment 22 is a method of producing the isolated monoclonal antibody or antigen-binding fragment thereof of any one of embodiments 15-21, comprising reacting an electrophile, preferably bromoacetamide or maleimide, introduced onto a sidechain of the therapeutic peptide, with the sulfhydryl group of the cysteine residue of SEQ ID NO:18 of the monoclonal antibody or antigen-binding fragment thereof, thereby creating a covalent linkage between the therapeutic peptide and the monoclonal antibody or antigen-binding fragment thereof.

Embodiment 23 is a pharmaceutical composition comprising the isolated monoclonal antibody or antigen-binding fragment thereof of any one of embodiments 14-21 and a pharmaceutically acceptable carrier.

Embodiment 24 is a method of producing a pharmaceutical composition comprising the monoclonal antibody or antigen-binding fragment thereof of any one of embodiments 14-21, the method comprising combining the monoclonal antibody or antigen-binding fragment thereof with a pharmaceutically acceptable carrier to obtain the pharmaceutical composition.

Embodiment 25 is a kit comprising the monoclonal antibody or antigen-binding fragment thereof of any one of embodiments 1-9 and 14-21.

Embodiment 26 is a method of increasing the half-life of a therapeutic peptide in a subject, the method comprising conjugating the therapeutic peptide with a monoclonal antibody or antigen-binding fragment thereof comprising a heavy chain complementarity determining region 1 (HCDR1), HCDR2, HCDR3, and a light chain complementarity determining region 1 (LCDR1), LCDR2, and LCDR3, having the polypeptide sequences of SEQ ID NO: 16, 17, 18, 19, 20, and 21, respectively, wherein the therapeutic peptide is conjugated to the monoclonal antibody or antigen-binding fragment thereof at the Cys residue of SEQ ID NO:18.

Embodiment 27 is the method of embodiment 26, wherein the therapeutic peptide is selected from the group consisting of oxyntomodulin, glucagon-like peptide 1 (GLP1), peptide tyrosine tyrosine (PYY), exendin (exenatide), amylin (pramlintide), alpha-melanocyte stimulating hormone (MSH), cocaine- and amphetamine-regulated transcript (CART), neuropeptide Y receptor Y1 (NPY1) antagonists, neuropeptide Y receptor Y5 (NPY5) antagonists, neurotensin S, neuropeptide B, neuropeptide W, ghrelin, bombesin-like receptor 3 (BRS3), galanin, cholecystokinin (CCK), orexin, melanin-concentrating hormone (MCH), oxytocin, and stresscopin.

Embodiment 28 is the method of embodiment 27, wherein the therapeutic peptide is oxyntomodulin.

Embodiment 29 is the method of claim 28, wherein the oxyntomodulin has a polypeptide sequence of SEQ ID NO:24.

Embodiment 30 is the method of any one of embodiments 25-29, wherein the monoclonal antibody comprises a heavy chain variable domain (VH) having the polypeptide sequence of SEQ ID NO:12.

Embodiment 31 is the method of any one of claims 25-30, wherein the monoclonal antibody comprises a heavy chain (HC) having the polypeptide sequence of SEQ ID NO:13.

Embodiment 32 is the method of any one of embodiments 25-31, wherein the monoclonal antibody comprises a light chain variable domain (VL) having the polypeptide sequence of SEQ ID NO:14.

Embodiment 33 is the method of any one of embodiments 25-32, wherein the monoclonal antibody comprises a light chain (LC) having the polypeptide sequence of SEQ ID NO:15.

Embodiment 34 is an isolated monoclonal antibody or antigen-binding fragment thereof comprising a heavy chain complementarity determining region 3 comprising SEQ ID NO:18, wherein the isolated monoclonal antibody or antigen-binding fragment thereof is capable of being coupled to a therapeutic peptide.

EXAMPLES

Example 1: Identification and Production of mAb MSCB97

Selection of PH9L3 VL and PH9H5 VII as Starting V Regions for Engineering

The antibody light chain variable region (VL) designated PH9L3 (SEQ ID NO:3) (Teplyakov et al., "Structural diversity in a human antibody germline library," mAbs August-September 8(6):1045-63 (2016)) and the antibody heavy chain variable region (VH) designated PH9H5 (SEQ ID NO:4) (Teplyakov et al., "Structural diversity in a human antibody germline library," mAbs August-September 8(6): 1045-63 (2016)) were selected as the starting variable regions from which to engineer a mAb enabled for peptide conjugation. PH9L3 is comprised completely of human Ig germline V gene sequences and as such does not contain any sequence mutations from the in vivo affinity maturation process that would result in high affinity, antigen-specific binding. The CDR3 of PH9H5 is the only segment not comprised of human germline V gene sequences in that VH. CDR3 (SEQ ID NO:5) of PH9H5 is identical to the CDR3 of an anti-human CCL2 antibody, CNTO 888, a neutralizing CCL2 antibody, see, e.g., US 20100074886 A1, the relevant disclosure on CNTO 888 is incorporated by reference in its entirety. A Fab containing the PH9H5/PH9L3 VH/VL pair was generated.

The PH9L3, PH9H5 and the human Ig germline V-region and J-region sequences to which these are most similar were aligned to determine sequence identity or similarity to the germline sequences. PH9H5 was aligned to a concatenation (SEQ ID NO:6) of human Ig germline genes IGHV3-23*01 (PubMed ID: M99660) (SEQ ID NO:7) and human IGHJ1*01 (PubMed ID: J00256) (SEQ ID NO:8), with the only difference between the PH9H5 amino acid sequence and the concatenated human IGHV3-23*01-IGHJ1*01 sequence being at VH CDR3, which was SEQ ID NO:5 for PH9H5.

PH9L3 was aligned to a concatenation (SEQ ID NO:9) of human Ig germline genes IGKV3-11*01 (PubMed ID: X01668) (SEQ ID NO:10) and IGKJ1*01 (PubMed ID: J00242) (SEQ ID NO:11), with the only difference being one deviation in the V gene/J gene junction.

Design and Generation of Cys Substituted Variants of PH9H5 and PH9L3

Variants of the PH9H5 VH that contain a single Cys substitution at select CDR residues across all three CDRs of the V region were designed, generated and cloned as complete heavy chains with a human IgG1 constant region into a mammalian host expression vector. The PH9H5/PH9L3 Fab structure was utilized to aid in selection of CDR residues for substitution that appear more accessible for conjugation and in some of the variants, additional glycine (Gly) residues were inserted on either side of the introduced Cys residue to potentially increase accessibility of the Cys for conjugation. Similar variants of the PH9L3 VL were designed and generated except these were cloned as complete light chains with a human kappa constant region into the expression vector. A total of 24 expression constructs of PH9H5 single Cys variants and 22 expression constructs of PH9L3 single Cys variants were generated. The residues selected for substitution within PH9H5_VH (SEQ ID NO:4) and within PH9L3_VL (SEQ ID NO:3) are summarized in FIG. 2.

The expression constructs generated were used to express the Cys variants by transiently co-transfecting each PH9H5 based HC Cys variant construct with the wild type PH9L3 LC construct or co-transfecting each PH9L3 based LC Cys variant construct with the wild type PH9H5 HC construct. Initial test transfections used HEK-derived Expi293 as expression host and were at 20 ml scale. The majority of both HC and LC Cys variants expressed well based on variant protein quantitation from culture supernatant.

Five initial HC Cys variants, MSCB33-MSCB37, were expressed in Expi293 at 750 ml scale and variant proteins purified. The purification yield and quality properties of the purified variants were fairly similar and sufficient for using the purified proteins in initial peptide conjugation reactions.

Evaluation of Peptide Conjugation to PH9H5-Based HC Cys Variants

Analytical mass determination of MSCB33 protein and other variant proteins indicated the presence of cysteine adducts at the Cys engineered for conjugation, with two per mAb, as well as removal of the HC C-terminal Lys residue, which is commonly seen in recombinantly produced mAbs. To prepare the variant mAbs for conjugation, adducts were removed by a reduction process developed to maintain the native disulfide bonds within the mAb (see Example 3). Initial test conjugations with a human oxyntomodulin (OXM) peptide analogue (GCG Aib2, Gly16,24, Arg20, Leu27, Lys30 (PEG$_{12}$)-NH$_2$) were done using maleimide chemistry on all five HC Cys variant mAbs. Conjugation efficiency differed between mAb variants, which was qualitatively estimated by the conjugation reaction products and the relative percentage of each. Greatest efficiency, as measured by greatest percentage of homodimer product, was observed with MSCB33, as compared to the other I102C variants containing flanking Gly residues, and little or no conjugation was observed with the Y103C variants MSCB35 or MSCB37.

Several other HC and LC Cys variants, with engineered cysteine substitutions in various CDRs (a T28C, S30C, and S54C substitution in PH9H5_VH (SEQ ID NO:129), and an S30C and S92C substitution in PHpL3_VL (SEQ ID NO:128)) were expressed at large scale in Expi293. Removal of the Cys adducts from these purified proteins by reduction was challenging and these variants were not pursued further. Due to the challenges observed with most of the Cys variants and the initial good conjugation efficiency observed with the I102C PH9H5 variant mAb, MSCB33, process development and further engineering efforts focused on this particular variant.

Fc Engineering of MSCB33

MSCB33 was re-engineered to contain the silent, human IgG4_PAA Fc to reduce Fc function in vivo. Human IgG4_PAA has mutations S228P/F234A/L235A on the human IgG4 allotype nG4m(a) (based on IGHG4*01 allele as defined in IMGT). An expression construct with the VH of MSCB33 fused to the IgG4_PAA Fc was generated and used together with the same LC expression construct used for MSCB33 expression to produce the IgG4_PAA variant of MSCB33, which is designated MSCB97. The amino acid sequences of MSCB97 VH, HC, VL, and LC are provided by SEQ ID NO:12, 13, 14, and 15, respectively.

Test expression of MSCB97 was done transiently at 20 ml scale in Expi293 cells and this mAb variant expressed well. MSCB97 was purified from a large scale, Expi293 expression run. The purification yield of MSCB97 was 264.53 mg/L, and the quality was determined at 85% monomer species. Subsequent large scale expression runs and purifications were similar or better in yield and quality and indicated the consistency with which this mAb could be produced.

Evaluation of Peptide Conjugation to MSCB97 and Conjugation Reaction Scalability The LC-HC disulfide connectivity differs between the IgG1 and IgG4 isotypes, so the reduction and maleimide conjugation was tested and confirmed to be translatable from the IgG1 mAb MSCB33 to the IgG4_PAA mAb MSCB97 using TCEP reduction and conjugation of the OXM-maleimide test peptide described above. The linkage resulting from maleimide conjugation is known to be potentially reversible, so bromoacetamide conjugation chemistry, which produces a more stable linkage, was adopted and implemented successfully on a 10 mg scale based on starting MSCB97.

The MSCB97 conjugate of the OXM analogue GCG Aib2, Glu16,24, Arg20, Leu27, Lys30-ε-(PEG$_{12}$)-NH$_2$ (compound 2—"compound 2" and "conjugate 2" can be used interchangeably herein) (MSCB97 conjugated to H-Aib-QGTFTSDYSKYLDERRARDFVEWLLNTK-(COCH$_2$CH$_2$(OCH$_2$CH$_2$)$_{12}$NHCOCH$_2$Br)—NH$_2$ (SEQ ID NO: 24) to form compound 2 (FIG. 11; SEQ ID NO:27)) generated through bromoacetamide chemistry was assayed to determine in vitro GLP-1R and GCGR potencies. Potencies relative to reference peptides and reference unstructured peptide conjugates were reasonable and similar to that of the conjugate generated with the same peptide to MSCB33 (IgG1). This demonstrated that the single difference between MSCB97 (IgG4_PAA) and MSCB33 (IgG1), which is isotype, had no impact on the potency of conjugates containing the same peptide. Additionally, these data showed that desirable in vitro potencies could be retained in a peptide-mAb conjugate generated with bromoacetamide chemistry that produces a linkage that is stable in vivo. Other OXM analogues were also conjugated to MSCB97 and in vitro potencies of these conjugates assayed. These conjugates had similar GLP-1R and GCGR potencies to compound 2, highlighting the ability to conjugate a variety of peptides to MSCB97, while retaining peptide potency.

Evaluation of Peptide-MSCB97 Conjugate Binding to Human CCL2

While MSCB97 was selected and engineered for lack of specific antigen binding, the most likely antigen that this mAb might bind, if any, is human CCL2 based on the origin of the VH CDR3. Whether MSCB97 does demonstrate any specific CCL2 binding was evaluated using two peptide-MSCB97 conjugates, with an OXM peptide analogue, (compound 2), or a PYY peptide analogue, (compound 1—"compound 1" and "conjugate 1" can be used interchangeably herein).

Potential CCL2 binding was directly measured by surface plasmon resonance (SPR) in which the conjugates were surface-immobilized using an anti-Fc capture method. A commercially available anti-CCL2 mouse mAb served as a positive control and two non-specific human antibodies, CNTO 9412 and HH3B33, served as negative controls. All controls were similarly surface-immobilized and recombinant human CCL2 was flowed over immobilized conjugates and controls at concentrations up to 400 nM. Based on the pre-established assay criteria, CCL2 accumulation, indicating specific antigen binding, was seen with the positive control but not with the negative controls nor with either peptide-MSCB97 conjugate (compound 1 or 2). This confirmed that MSCB97, in the relevant therapeutic form of a peptide-mAb conjugate, lacks human CCL2 binding.

SPR Binding Method:

Binding measurements using Surface Plasmon Resonance (SPR) were performed using a ProteOn XPR36 system (BioRad). A biosensor surface was prepared by coupling a mixture of anti-Human IgG Fc (Jackson cat #109-005-098) and anti-Mouse IgG Fc (Jackson cat #315-005-046) to the modified alginate polymer layer surface of a GLC chip (BioRad, Cat #176-5011) using the manufacturer instructions for amine-coupling chemistry. Approximately 5700 RU (response units) of mAbs were immobilized. The binding experiments were performed at 25° C. in running buffer (DPBS; 0.01% P20; 100 μg/ml BSA). To perform binding kinetic experiment, samples (compound 2, compound 1, and control mAbs-positive and negative) were captured followed by injections of Recombinant human CCL2 (Thermo, catalog #RMCP120) at 5 concentrations (in a 4-fold serial dilution). The association phase was monitored for 3 minutes at 50 μL/min, then followed by 5 minutes of buffer flow (dissociation phase). The chip surface was regenerated with two 18 second pulses of 100 mM H$_3$PO$_4$ (Sigma, Cat #7961) at 100 μL/min.

The collected data were processed using ProteOn Manager software. First, the data was corrected for background using inter-spots. Then, double reference subtraction of the data was performed by using the buffer injection for analyte injections. Pre-established assay criteria for determining specific detectable binding of compound 2, compound 1, and the positive control to CCL2 required a dose proportional response with >10 RU signal at the highest concentration, and negative control response signals <10 RU. Based on the assay criteria, the results for each sample was reported as Yes or No to dose-response binding to human CCL2.

Example 2: Expression and Purification of the mAb

The fully human monoclonal antibody (mAb) can be recombinantly expressed in a mammalian expression host and purified from the cell culture supernatant using standard methods that are known in the field. For example, a cDNA sequence encoding the light (LC) and heavy chains (HC) of the mAb, each including an appropriate signal peptide to enable secretion, can be cloned into separate mammalian expression vectors or into a single expression vector using standard molecular biology methods. Expression vectors used can be any of those commercially available such as pEE12.4, pcDNA™ 3.1(+) or pIRESpuro3 or any custom expression vector with similar functionalities. In such vectors transcription of the heavy and light chains of the mAb are each driven by any of the known effective promoters such as the hCMV-MIE promoter. Transfection grade plasmid DNA is prepared for separate LC and HC expression constructs or a single construct expressing both LC and HC using standard methods such as a QIAGEN Plasmid Midi Kit.

Purified plasmid DNA is prepared for transfection with a lipid-based transfection reagent such as FREESTYLE™

Max transfection reagent, following manufacturer's instructions, and is then transfected into a standard mammalian expression host cell line, such as CHO-S or HEK 293-F. If the mAb LC and HC are encoded by separate expression constructs, the two constructs are simultaneously transfected. Prior to and after transfection, mammalian cells are cultured for maintenance or for mAb expression following standard cell culture methods whereby the cell density ranges to maintain, the culture media to use, and the other cell culture conditions followed are determined by the specific mammalian host cell line utilized. These parameters are typically documented by the vendor from which the cell line was obtained or in the scientific literature. For example, CHO-S cells are maintained in CHO FREESTYLE™ media in suspension, shaking at 125 RPM in a humidified incubator set at 37° C. and 8% $CO_2$, and split when the cell concentration is between 1.5 and $2.0 \times 10^6$ cells per ml.

Cell culture supernatants from the transiently transfected mammalian cells expressing the mAb are harvested several days after transfection, clarified by centrifugation and filtered. Duration of expression for CHO-S cells is typically four days but can be adjusted and can differ for different mammalian host cell lines. Large scale transfections (>10 liters) are concentrated 10-fold using a concentrator such as a Centramate. The mAb is purified from the clarified supernatant using a Protein A affinity column such as the HiTrap Mab Select Sure utilizing standard methods for binding mAb to Protein A resin, washing the resin and eluting the protein using low pH buffer. The protein fractions are neutralized immediately by elution into tubes containing pH 7 buffer and peak fractions are pooled, filtered and dialyzed against phosphate buffered saline (PBS), pH 7.2 overnight at 4° C. After dialysis the mAb is filtered again (0.2µ filter) and the protein concentration is determined by absorbance at 280 nm. Quality of the purified mAb protein is assessed by SDS-PAGE (polyacrylamide gel electrophoresis) and analytical size exclusion HPLC and endotoxin levels are measured using a limulus amebocyte lysate (LAL) assay. Purified mAb is stored at 4° C.

Expression and Purification of MSCB97 from Transiently Transfected CHO Cells

MSCB97 was expressed in EXPICHO-S™ cells (ThermoFisher Scientific, Waltham, Mass.; Cat #A29127) by transient transfection of the cells with purified plasmid DNA of a MSCB97 expression construct following manufacturer's recommendations. Briefly, EXPICHO-S™ cells were maintained in suspension in EXPICHO™ expression medium (ThermoFisher Scientific, Cat #A29100) in a shaking incubator set at 37° C., 8% $CO_2$ and 125 RPM. The cells were passaged so that on the day of transfection, dilution down to $6.0 \times 10^6$ cells per ml could be achieved, maintaining cell viability at 98% or better. Transient transfections were done using the EXPIFECTAMINE™ CHO transfection kit (ThermoFisher Scientific Cat #A29131). For each ml of diluted cells to be transfected, one microgram of plasmid DNA is used and diluted into OPTIPRO™ SFM complexation medium. EXPIFECTAMINE™ CHO reagent is used at a 1:3 ratio (v/v, DNA:reagent) and also diluted into OPTIPRO™. The diluted DNA and transfection reagent were combined for one minute, allowing DNA/lipid complex formation, and then added to the cells. After overnight incubation, EXPICHO™ feed and EXPIFECTAMINE™ CHO enhancer were added to the cells. Cells were cultured with shaking at 32° C. for five days prior to harvesting the culture supernatants.

Culture supernatants from the transiently transfected EXPICHO-S™ cells were harvested by clarifying through centrifugation (30 min, 6000 rpm) followed by filtration (0.2µ PES membrane, Corning). Large scale transfections (5 to 20 liters) were first concentrated 10-fold using a Pall Centramate Tangential Flow Filtration system. 10× Dulbecco's phosphate-buffered saline (DPBS), pH7.2 was added to the supernatant to 1× final concentration prior to loading onto an equilibrated (DPBS, pH 7.2) HiTrap Mab Select Sure Protein A column (GE Healthcare; Little Chalfont, United Kingdom) at a relative concentration of ~20 mg protein per ml of resin, using an AKTA FPLC chromatography system. After loading, the column was washed with 10 column volumes of DPBS, pH7.2. The protein was eluted with 10 column volumes of 0.1 M Na-Acetate, pH 3.5. Protein fractions were neutralized immediately by elution into tubes containing 2.0 M tris(hydroxymethyl)aminomethane (Tris), pH 7 at 20% the elution fraction volume. Peak fractions were pooled and the pH adjusted to ~5.5 with additional Tris, if necessary. The purified protein was filtered (0.20µ) and the concentration was determined by absorbance at 280 nm on a BioTek SYNERGYHT™ spectrophotometer. The quality of the purified protein was assessed by SDS-PAGE and analytical size exclusion HPLC (Dionex HPLC system). The endotoxin level was measured using a turbidometric LAL assay (PYROTELL®-T, Associates of Cape Cod).

Example 3: Conjugation of mAb and Cyclic PYY Peptides

Method A: Partial Reduction of mAb with TCEP

A 10 mg/mL solution of mAb in tris-acetate buffer (20 mL, 1 mM in EDTA) was treated with 3 equivalents of TCEP. The solution was adjusted to pH 6 and after 1 hr at room temperature (rt) high pressure liquid chromatography with mass spectrometer (LCMS) showed that the disulfide adducts at position C102 had been completely reduced. The reduced mAb was purified by protein A adsorption and elution (4 CV 100 mM acetic acid) to provide 180 mg of reduced mAb.

Conjugation of Reduced mAb and Cyclic PYY Peptides

Lyophilized peptide (5 eq vs mAb) was added to the reduced mAb described above. EDTA was added to a final concentration of 1 mM and the pH was adjusted to 7. The concentration was adjusted to 8 mg/mL and the reaction was allowed to proceed with gentle agitation for 16 h at room temperature. TCEP (0.5 eq vs mAb) was added and the reaction was allowed to proceed further for 4 hr at rt with gentle agitation, after which time the high molecular weight (MW) species were reduced to less than 3%.

The reaction mixture was adjusted to pH 5.5 and purified by ion exchange chromatography on CaptoSP resin using a gradient 100% A (100 mM TRIS-acetate, pH 5.5) to 100% B (100 mM TRIS-acetate, pH 5.5; 0.5 M NaCl) over 20 CV. Fractions containing the desired conjugate were pooled and 140 mg of conjugate were recovered, coeluting with a small amount of unreacted peptide. Final purification was by protein A adsorption and elution (4 CV 100 mM acetic acid). The pH of the product was adjusted to 6 to give 120 mg of conjugate (60% yield) at >90% purity with <3% high MW species.

Method B

Hydrophobic Interaction Chromatography (HIC) Purification of mAb

A 20 mg/mL solution of mAb in tris-acetate buffer was loaded on a hydrophobic interaction column (TOSOH TSK-gel phenyl 7.5×21 cm) and eluted with a linear gradient (0-70% B/A, solvent A: 5% iPrOH, 1M $(NH_4)_2SO_4$, 100 mM phosphate buffer, pH 6.0; solvent B: 20% iPrOH, 100 mM phosphate buffer). The mAb monomer peaks were pooled, concentrated (5-10 mg/mL) and dialyzed against 3-(N-morpholino) propanesulfonic acid (MOPS) buffer (100 mM, pH 5.5).

Partial Reduction with TCEP and Conjugation of Reduced mAb with Peptide Analog

To the purified mAb (27 mL, 9.28 mg/mL) was added 4 eq. TCEP followed by EDTA (1 mM). After 2 hr at room temperature LCMS showed that the disulfide adducts at position C102 had been completely reduced. The reduced mAb was treated with Zebra desalting spin column (7×10 mL, 7K MWCO, pre-equilibrium with MOPS 100 mM pH 5.5) to remove the liberated cysteines/GSH. To the combined fractions of the reduced mAb (28 mL) was added a solution of cyclic PYY peptide in Milli Q grade water (6.5 eq vs mAb, 15-20 mg/mL) followed by EDTA (1 mM). The pH of the reaction was adjusted to 7.2 to 7.4 by dropwise addition of 1N NaOH. The reaction was allowed to proceed 18 h at room temperature with gentle agitation. The reaction was continued for another 12 h after addition of a further 0.5 equiv TCEP to reduce mAb-mAb dimer formed during the course of the reaction and allow conversion to the desired mAb homodimer. The pH of the reaction was lowered to pH 5.5 by addition of 2 M acetic acid and the crude conjugate was purified by hydrophobic interaction chromatography and eluted with a linear gradient (0-100% B/A, solvent A: 5% iPrOH, 1M (NH4)2SO4, 100 mM phosphate buffer, pH 6.0; solvent B: 20% iPrOH, 100 mM phosphate buffer). Final purification was by protein A adsorption (PBS) and elution (NaOAc, pH 3.5). The pH of the product was adjusted to 6 and dialyzed against PBS to give the final sample (56%).

Alternatively, the mAb was reduced with GSH and/or Cys. After removal of the reducing agent by Tangential Flow Filtration (TFF), an excess of the peptide was added to the reduced mAb optionally in the presence of 0.2-0.5 equivalents of TCEP.

Example 4: In Vitro Studies

Compound 1 (SEQ ID NO:2), a monoclonal antibody couple to a cyclic PYY peptide (FIG. 3), was evaluated for its ability to activate NPY receptors in vitro in clonal cells (HEK or CHO) expressing human, rat, mouse and rhesus monkey Y2 receptors, and human Y1, Y4 and Y5 receptors. $PYY_{3-36}$, NPY and PP were included in these assays as study controls.

Cell Lines

Stable transfected clonal cell lines expressing NPY receptors were developed for use in cAMP assays. In brief, HEK293 cell lines were transfected using the Lipofectamine 2000 kit (Invitrogen) according to its protocol with expression plasmids carrying the coding sequences for the human Y2 receptor (Accession No.: NM_000910.2), the human Y5 receptor (Accession No.: NM_006174.2), the mouse Y2 receptor (Accession No.: NM_008731) and the rhesus monkey Y2 receptor (Accession No.: NM_001032832). Forty eight hours after transfection, cells were re-plated with selection media (DMEM high glucose with 10% fetal bovine serum (FBS), 50 I.U. penicillin, 50 µg/ml streptomycin, 2 mM L-glutamine, 1 mM sodium pyruvate and 600 µg/ml G418). Cells were kept in selection media for 2 weeks before single clones were picked using limited dilution method. The transfected cells were subsequently maintained by culturing in DMEM-high glucose media (Cellgro) supplemented with 10% fetal bovine serum, 1% L-glutamine, 1% sodium pyruvate, 1% penicillin/streptomycin and 600 µg/ml G418.

In addition, CHO-K1 cell lines were obtained from DiscoverX Corporation, expressing the human Y1 receptor (Catalog No.: 93-0397C2) and the human Y4 receptor (Catalog No.: 95-0087C2). The DiscoverX cells cultured in F12 media (Gibco) supplemented with 10% FBS and under the G418 selection (800 µg/mL). The rat Y2 receptor was expressed in a Glo-Sensor CHO-K1 line obtained from Promega Corporation. These cells were transfected with the pGLOSENSOR™-23F cAMP plasmid for a luminescent based cAMP assay but had been tested and validated for use with the Perkin-Elmer LANCE cAMP assay. The rat Y2 cells were grown in F12 media (Gibco) supplemented with 10% FBS and 800 µg/ml G418.

All the cell lines were banked in vials ($4\times10^6$ cells/vial) and stored in liquid nitrogen until use. The day before the assay, the vials were thawed and added to 15 mls of appropriate media. Cells were centrifuged at 450×g for 5 min, supernatants were aspirated and cells were re-suspended in media without G418 at a density of $0.2\times10^6$ cells/ml. Cells were dispensed (25 µl/well) into Biocoat collagen-coated white 384 well plates to a final density of 5000 cells/well. The cell plates were incubated overnight in a 37° C. humidified tissue culture incubator under 5% $CO_2$/90% $O_2$ atmosphere.

Experimental Protocol

The cAMP assay was the same for the various receptor assays. The LANCE cAMP kit (Perkin Elmer Corporation; Waltham, Mass.) was used in all experiments to quantitate intracellular cAMP levels. On the day of the assay, the cell media was decanted from the cells and 6 µl of peptides (2× concentration) was added to the wells. Peptides were made up as an 11 point dose response (starting at 100 nM or 10 µM with serial 1:3 dilutions) in stimulation buffer. Stimulation buffer consists of 5 mM HEPES (4-(2-hydroxyethyl)-1-piperazineethanesulfonic acid), 500 µM IBMX and 0.1% bovine serum albumin (BSA) in HBSS (Hank's balanced salt solution). Next 6 µl of stimulation buffer containing forskolin (2×, 5 µM final concentration) and LANCE cAMP antibody (1:100) was added to the cells. After incubation for 25 minutes at rt, 12 µl of assay detection mix was added to each well. The detection mix was prepared by diluting biotin-cAMP (1:750) and Europium-W8044 (1:2250) in detection buffer as provided with the LANCE cAMP kit. The plate was incubated for 2 hours at rt and then read as a TR-FRET assay on the Envision plate reader (excitation 320 nm, emission 615 nm and 665 nm). Channel 1 fluorescence (relative fluorescent units at 615 nm) and channel 2 fluorescence (relative fluorescent units at 665 nm) along with their ratio were exported into an Excel file.

Data Analysis

Data from the Envision plate reader were expressed as relative fluorescence units (RFU) calculated as (615 nm/665 nm)×10,000. All samples were measured in triplicate. Data were analyzed using the Crucible in-house data analysis software, designed by Eudean Shaw. The unknown cAMP concentrations within each well were interpolated from the reference standards of known cAMP concentrations included within each plate. Parameters such as $EC_{50}$, Log ($EC_{50}$), HillSlope (nH), top, and bottom, were derived by plotting cAMP concentration values over log compound concentrations fitted with 4-P model using a non-linear weighted least squares application within R environment (Open Source http://cran.us.r-project.org/) implemented by the Non-Clinical Statistics & Computing department at Janssen R&D.

TABLE 1 in vitro Data

| Compound | Human isoform potency (EC$_{50}$ nM) | | | | Cross-species potency (EC$_{50}$ nM) | | |
| --- | --- | --- | --- | --- | --- | --- | --- |
| | hY2 | hY1 | hY4 | hY5 | Mouse Y2 | Rat Y2 | Rhesus Monkey Y2 |
| Compound 1 | 0.006 | >2910 | >2910 | 345.7 | 0.004 | 0.04 | 0.004 |
| PYY3-36 | 0.08 | 66.4 | 136.7 | 12.3 | 0.03 | 0.50 | 0.06 |

Example 5: Pharmacokinetics (PK)

DIO Mouse PK

Male DIO C57BL/6N mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet).

Mice were dosed subcutaneously (s.c.) with 1 mg/kg compound 1, 3 animals were sacrificed at each time point and blood was collected at t=4, 8, 24, 48, 72, 120, and 168 hours. Blood from 3 naïve animals was also collected. Approximately 300 μL of blood from each animal was collected via jugular vein after decapitation while under gas anesthesia induced with 70% $CO_2$ and 30% $O_2$ mixture. Blood samples (approximately 300 μL) was collected in K3E (EDTA) coated Sarstedt MICROVETTE® tubes containing 12 μl (4% ratio) of complete protease inhibitor solution and 3 (1% ratio) of DPP-IV inhibitor. Blood samples were placed on wet ice prior to being centrifuged at 10,000 rpm for ~4 minutes under refrigerated conditions (~5° C.) for cell removal within 30 minutes following collection at each time point and all available plasma was transferred to a 96-well plate. The well plate was stored on dry ice until it was placed in a –80° C. freezer. Data are shown in Table 2 and FIG. 4.

Rat PK

Compound 1 was administered subcutaneously and intravenously to male Sprague-Dawley rats (Charles River Laboratories, Wilmington, Mass.) at a dose level of 1.0 mg/kg in PBS, (pH 7.0-7.6). Approximately 500 μL of blood was collected from three animals per time point via a saphenous vein (t=1, 4, 24, 48, 72, 96, 168, and 240 hours post-dose). A 336 hour post-dose blood sample was collected via jugular vein after decapitation while under gas anesthesia induced with 70% $CO_2$ and 30% $O_2$ mixture. Blood samples were collected in K3E (EDTA) coated Sarstedt MICROVETTE® tubes containing 20 μl (4% ratio) of complete protease inhibitor solution and 5 μL (1% ratio) of DPPIV inhibitor. Blood samples were placed on wet ice prior to being centrifuged at 10,000 rpm for ~4 minutes under refrigerated conditions (~5° C.) for cell removal within 60 minutes following collection at each time point and all available plasma was transferred to a 96-well plate. The levels of Compound 1 were measured using the LCMS method described below. Data are shown in Table 3.

Cynomolgus Monkey (Cyno) PK

All animals were fasted for at least eight hours prior to dosing and through the first four hours of blood sample collection. Three animals received a single IV dose of 1 mg/kg Compound 1 and three animals received a single SC dose of 1 mg/kg Compound 1. Blood was collected pre-dose and at 1, 6, 10, 24, 36, 48, 72, 120, 168, 240, 336, 432, and 504 hours post-dose. An additional sample was collected at 0.5 hours post-dose for the IV group. Approximately 1 ml of blood from each animal was collected in K3E (EDTA) coated Sarstedt MICROVETTE® tubes containing 4% ratio of complete protease inhibitor solution and 1% ratio of DPPIV inhibitor. Blood samples were placed on wet ice prior to being centrifuged within 30 minutes following collection at each time point and the resulting plasma was split in thirds and transferred into triplicate 96-well plate. The well plate was stored on dry ice until it was placed in a –80° C. freezer. Data are shown in Table 4 and FIG. 5.

Intact Mass Spec Assay for Determination of Plasma Levels

Figure 5:
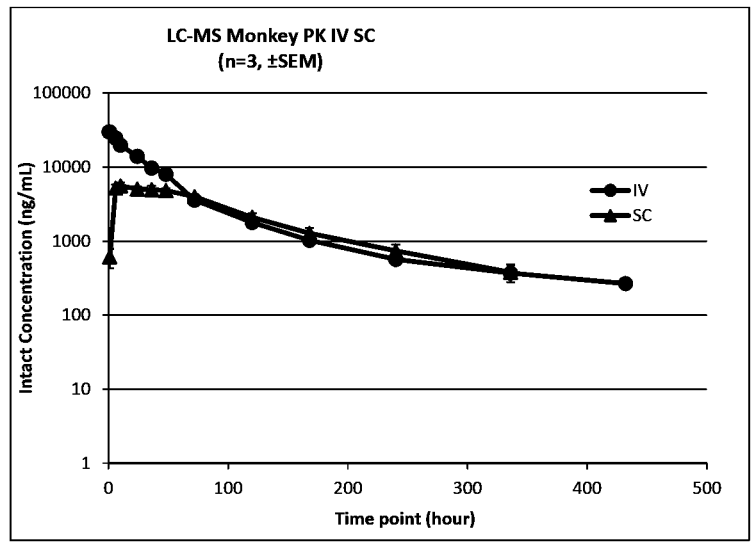
FIG. 5: Pharmacokinetics of the compound 1 in cynomolgus monkeys.

Plasma samples were processed by immuno-affinity capture using an anti-human Fc antibody, followed by reversed phase LC-high resolution full scan MS analysis on a triple TOF (time-of-flight) mass spectrometer. The raw MS spectra were deconvoluted to elucidate the molecular weights of the components in the injected samples. The peak of the molecule ion of the intact conjugate was used for quantitation. Standard curve and quality control samples were prepared by spiking the reference standard in plasma and processed using the same procedure at the same time as the incurred samples. PK data for DIO mouse, rat, and cyno are shown in Tables 2-4, respectively. PK data for DIO mouse and Cyno are also shown in FIGS. 4 and 5, respectively.

TABLE 2

PK in DIO Mouse

| Assay | Dose (mg/kg) | $T_{1/2}$ hr | $T_{max}$ hr | $C_{max}$ ng/mL | AUC$_{last}$ hr * ng/mL |
| --- | --- | --- | --- | --- | --- |
| Intact | 1.0 | 81.05 | 48 | 8750 | 995460 |

TABLE 3

PK in rat

| Route | Dose (mg/kg) | $T_{1/2}$ hr | $T_{max}$ hr | $C_{max}$ ng/mL | AUC$_{last}$ hr*ng/mL |
| --- | --- | --- | --- | --- | --- |
| IV | 1.0 | 93.0 | 1 | 19.5 | 809.2 |
| SC | 1.0 | 88.7 | 48 | 4.2 | 602.0 |

TABLE 4

PK in Cyno

| Route | Dose (mg/kg) | $T_{1/2}$ hr | $T_{max}$ hr | $C_{max}$ ng/mL | AUC$_{last}$ hr*ng/mL |
| --- | --- | --- | --- | --- | --- |
| IV | 1.0 | 178.39 | 0.67 | 30290 | 1207.39 |
| SC | 1.0 | 104.32 | 10 | 5590 | 712.19 |

Example 6: Efficacy Studies In Vivo

Weight Loss in Diet-Induced Obese (DIO) Mice: Acute Dosing

Compound 1 was evaluated for its ability to reduce foot intake and body weight in male DIO C57Bl/6 mice after a single dose. Male DIO C57BL/6N mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet). Animals were acclimated to the facility for at least one week prior to the start of the experiment.

Figure 6:
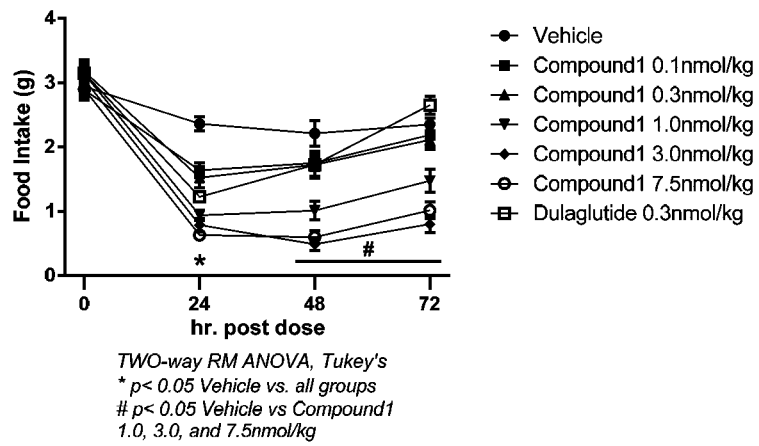
FIG. 6: Food intake in DIO mice treated with the compound 1: acute dosing.
Figure 7:
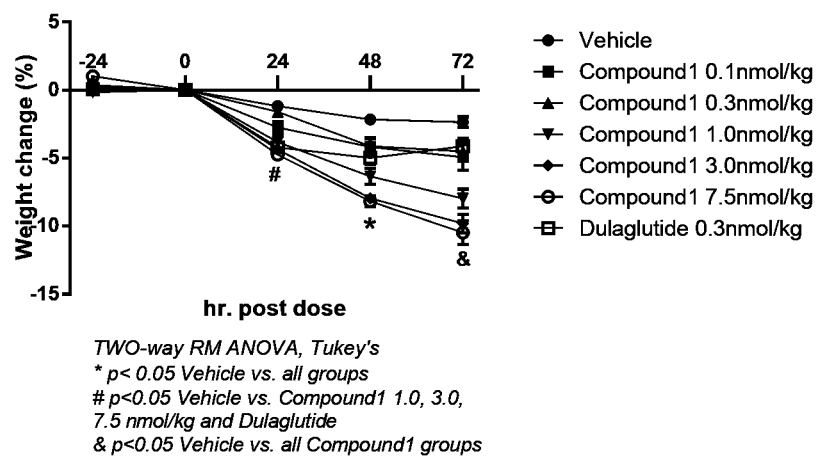
FIG. 7: Weight loss in DIO mice treated with the compound 1: acute dosing.

The day prior to dosing, mice were grouped into cohorts of eight animals based on individual body weights. At 3:00-4:00 pm the following day, animals were weighed and treated with vehicle (dPBS, pH 7.2), Compound 1 at a dose of 0.1, 0.3, 1.0, 3.0, or 7.5 nmol/kg, or Dulaglutide at 0.3 nmol/kg via subcutaneous (s.c.) administration. Body weights and food intake were measured 24 h, 48 h and 72 h after dosing and the percentages of weight loss and reduction in food intake were calculated. Statistical analyses were performed using two-way repeated measures ANOVA with Tukey's post-test in Prism. All data are presented as the mean±SEM (FIG. 6 and FIG. 7).

Weight Loss in Diet-Induced Obese Mice: Chronic Dosing

Compound 1 was evaluated for its ability to reduce foot intake and body weight and improve glucose homeostasis on repeat dosing in male DIO C57Bl/6 mice over a period of 8 days. Male DIO C57BL/6N mice (20 weeks of age, 14 weeks on high fat diet) were obtained from Taconic Laboratory. Mice were housed one mouse per cage with AlphaDri bedding in a temperature-controlled room with 12-h light/dark cycle. Mice were allowed ad libitum access to water and maintained on high fat diet (D12492, Research Diet). Animals were acclimated to the facility for at least one week prior to the start of the experiment.

Figure 8:
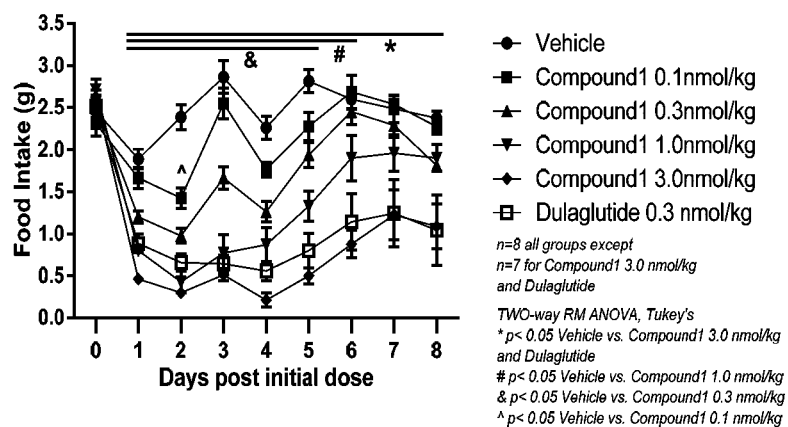
FIG. 8: Food intake in DIO mice treated with the compound 1: chronic dosing.
Figure 9:
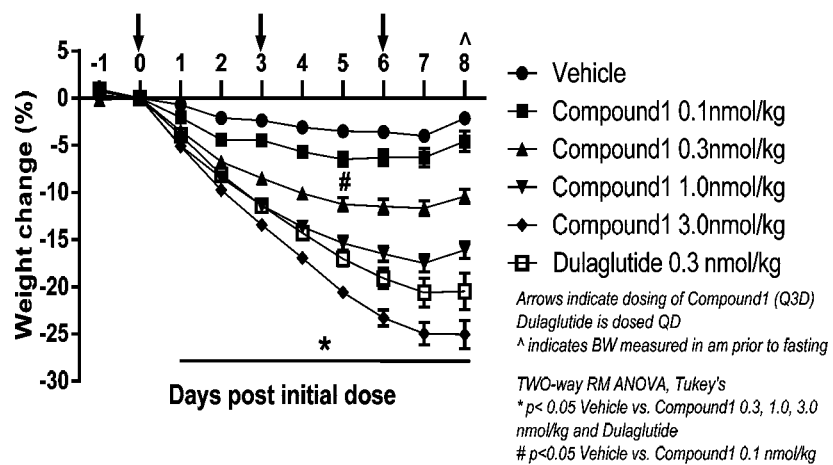
FIG. 9: Weight loss in DIO mice treated with the compound 1: chronic dosing.

The day prior to dosing, mice were grouped based on individual body weights. At 3:00-4:00 pm for each of the next 8 days, animals and food intake were weighed. Animals were treated with vehicle (dPBS, pH 7.2) or dulaglutide at 0.3 nmol/kg via subcutaneous administration every day or Compound 1 at doses of 0.1, 0.3, 1.0, 3.0 nmol/kg via subcutaneous administration every three days. After 8 days, mice are fasted for 5 hours and then given a 2 g/kg bolus of glucose orally at t=0. At t=0, 30, 60, 90, and 120 minutes post glucose challenge blood glucose is measured and at t=0, 30, and 90 minutes blood in drawn to measure plasma insulin. Statistical analyses were performed using one-way ANOVA or two-way repeated measures ANOVA with Tukey's post-test in Prism. All data are presented as the mean±SEM (FIGS. 8 and 9, and Tables 5-8).

TABLE 5

Effect of compound 1 on body weight (g) over 8 days treatment

| Treatment Day | Vehicle n/a | Compound 1 (nmol/kg) | | | | Dulaglutide (nmol/kg) |
| --- | --- | --- | --- | --- | --- | --- |
| | | 0.1 | 0.3 | 1.0 | 3.0 | 0.3 |
| −1 | 46.3 ± 0.6 | 46.3 ± 0.6 | 46.7 ± 0.8 | 46.3 ± 0.6 | 46.3 ± 0.6 | 46.3 ± 0.6 |
| 0 | 46.1 ± 0.7 | 46.0 ± 0.6 | 46.8 ± 0.7 | 46.3 ± 0.6 | 46.3 ± 0.6 | 45.9 ± 0.6 |
| 1 | 45.8 ± 0.7 | 45.0 ± 0.6 | 45.2 ± 0.7 | 43.9 ± 0.5 | 43.9 ± 0.6 | 44.1 ± 0.6 |
| 2 | 45.2 ± 0.7 | 43.9 ± 0.6 | 43.6 ± 0.7 | 42.4 ± 0.7* | 41.8 ± 0.7* | 42.2 ± 0.6* |
| 3 | 45.1 ± 0.7 | 43.9 ± 0.6 | 42.8 ± 0.6 | 41.0 ± 0.6* | 40.1 ± 0.6* | 40.6 ± 0.6* |
| 4 | 44.7 ± 0.7 | 43.4 ± 0.6 | 42.0 ± 0.6 | 39.9 ± 0.6* | 38.5 ± 0.6* | 39.3 ± 0.6* |
| 5 | 44.5 ± 0.7 | 43.0 ± 0.6 | 41.5 ± 0.5* | 39.1 ± 0.6* | 36.8 ± 0.7* | 38.1 ± 0.7* |
| 6 | 44.5 ± 0.7 | 43.1 ± 0.6 | 41.4 ± 0.5* | 38.6 ± 0.6* | 35.5 ± 0.8* | 37.1 ± 0.8* |
| 7 | 44.3 ± 0.7 | 43.1 ± 0.7 | 41.3 ± 0.5* | 38.2 ± 0.6* | 34.8 ± 0.9* | 36.4 ± 1.0* |
| 8 | 45.2 ± 0.6 | 46.3 ± 0.7 | 41.9 ± 0.5* | 38.8 ± 0.6 | 34.7 ± 1.0* | 36.5 ± 1.1* |

Values represent mean ± SEM for data from 8 animals per time per group *p<0.05, versus vehicle; two-way ANOVA RM, Tukey's multiple comparison test

TABLE 6

Effect of compound 1 on blood glucose (mg/dL) levels during an OGTT after 8 days of treatment

| Treatment | Dose (nmol/kg) | Time after glucose challenge (min) | | | | | Total AUC (mg/dl/ 120 min) | Delta AUC (mg/dl/ 120 min) |
| --- | --- | --- | --- | --- | --- | --- | --- | --- |
| | | 0 | 30 | 60 | 90 | 120 | | |
| Vehicle | NA | 148 ± 6 | 227 ± 15 | 272 ± 12 | 206 ± 9 | 209 ± 13 | 26492 ± 1232 | 8702 ± 1082 |
| Comp. 1 | 0.1 | 151 ± 4 | 213 ± 9 | 249 ± 10 | 186 ± 11 | 194 ± 15 | 24598 ± 849 | 6433 ± 677 |
| | 0.3 | 137 ± 6 | 191 ± 11 | 208 ± 10* | 146 ± 8* | 160 ± 8* | 20786 ± 728* | 4379 ± 364* |
| | 1.0 | 117 ± 5 | 146 ± 9* | 203 ± 10* | 135 ± 8* | 136 ± 5* | 18285 ± 769* | 4319 ± 522* |
| | 3.0 | 73 ± 11* | 129 ± 5* | 149 ± 10* | 93 ± 9* | 101 ± 9* | 13703 ± 0913* | 5004 ± 585 |
| Dulaglutide | 0.3 | 76 ± 9* | 151 ± 14* | 174 ± 17* | 104 ± 10* | 119 ± 9* | 15758 ± 1054* | 6668 ± 1846 |

Values represent mean ± SEM for data from 8 animals per time per group *p<0.05, versus vehicle; two-way ANOVA RM, Tukey's multiple comparison test for glucose values; one-way ANOVA, Tukey's multiple comparison test for AUC

TABLE 7

Effect of compound 1 on insulin (ng/mL) levels during an OGTT after 8 days of treatment

| Treatment | Dose (nmol/kg) | Time after glucose challenge (min) 0 | 30 | 90 | Total AUC (mg/dl/120 min) |
|---|---|---|---|---|---|
| Vehicle | NA | 5.6 ± 1.4 | 11.3 ± 3.0 | 4.0 ± 0.6 | 711.4 ± 164.1 |
| Comp. 1 | 0.1 | 3.0 ± 0.4 | 6.6 ± 0.8* | 2.4 ± 0.2 | 415.6 ± 44.2 |
|  | 0.3 | 2.3 ± 0.2 | 4.0 ± 0.6* | 1.7 ± 0.2 | 264.3 ± 33.0* |
|  | 1.0 | 1.3 ± 0.2* | 2.2 ± 0.1* | 1.1 ± 0.2 | 151.6 ± 12.5* |
|  | 3.0 | 0.4 ± 0.1* | 1.2 ± 0.1* | 0.4 ± 0.1* | 73.9+ ± 9.0* |
| Dulaglutide | 0.3 | 0.6 ± 0.1* | 1.7 ± 0.2* | 0.7 ± 0.2 | 108.8 ± 12.3* |

Values represent mean ± SEM for data from 8 animals per time per group
*$p < 0.05$, versus vehicle; two-way ANOVA RM, Tukey's multiple comparison test for glucose values; one-way ANOVA, Tukey's multiple comparison test for AUC

TABLE 8

Effect of compound 1 on fed blood glucose (mg/dL) levels after 8 days of treatment

| Treatment | Dose (nmol/kg) | Blood Glucose (mg/dL) |
|---|---|---|
| Vehicle | NA | 180 ± 5 |
| Compound 1 | 0.1 | 164 ± 6 |
|  | 0.3 | 160 ± 5 |
|  | 1.0 | 149 ± 6 |
|  | 3.0 | 105 ± 12* |
| Dulaglutide | 0.3 | 114 ± 13* |

Values represent mean ± SEM for data from 8 animals per time per group
*$p < 0.05$, versus vehicle; one-way ANOVA, Tukey's multiple comparison test

Example 7: Synthetic Strategy for Preparation of mAb-Oxyntomodulin (mAb-OXM) Compound Human oxyntomodulin (OXM) is a 37 amino-acid endogenous peptide (SEQ ID NO: 23) that has been shown to have beneficial pharmacology in patients with type 2 diabetes mellitus. Pharmacology is the result of agonism at both GLP1R and GCGR. Investigations of OXM analogs revealed a peptide variant that demonstrated good glucose control and weight-loss in a rodent model. The half-life of OXM in vivo is on the order of minutes in humans. Additional design for OXM was therefore undertaken to confer a half-life commensurate with once-weekly dosing. An increase in half-life was accomplished by increasing the stability of the OXM peptide towards proteolysis, and by increasing the circulating half-life of the peptide by covalent attachment of a monoclonal antibody (mAb). Proteolysis of the peptide payload by DPP4 was mitigated by substituting the serine at position 2 with aminoisobutyric acid (Aib). The helical topology of the peptide was stabilized by introducing a bifurcated salt bridge from Q20R to S16E and Q24E, and a potential oxidation liability was mitigated by the M27L variation. The parent mAb, MSCB97 (described above), was chosen to have low intrinsic antigen binding, and an isoleucine to cysteine point mutation in the HCDR3 (SEQ ID NO:18) region of the heavy chain (I102C) served as the point of attachment for the synthetic peptide payload. Effector function was silenced by using the IgG4 PAA isotype. A short oligoethylene glycol spacer was incorporated between the mAb and the peptide to ensure unhindered access of the peptide to GLP1R and GCGR. The spacer also confers favorable aqueous solubility that facilitates the conjugation chemistry. Attachment of the peptide-spacer to the mAb was accomplished by introducing a reactive bromoacetamide group at the distal end of the glycol spacer. The proximal end of the spacer was attached to the OXM variant via the side-chain of K30. The amino acid sequence of glucagon and the OXM peptide variant is provided by SEQ ID NOs:22 and 24, respectively. Conjugation was accomplished by reaction with the thiol functionality of the cysteine point mutation in the mAb heavy chain. The amino acid sequences of the mAb heavy and light chains are provided by SEQ ID NOs: 13 and 15, respectively.

Chemical Synthesis of mAb-OXM Compound

Figure 10:
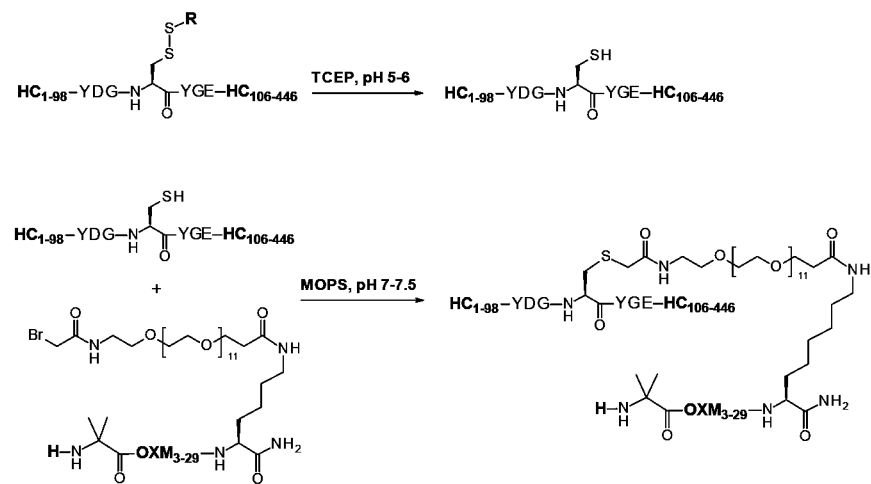
FIG. 10: Shows a reaction scheme to produce a monoclonal antibody oxyntomodulin (mAb-OXM) compound according to an embodiment of the invention. The top reaction is a reduction of the disulfide at Cys102 of the mAb (e.g., MSCB97). The bottom reaction is a conjugation of the reduced mAb with the OXM peptide variant. R is cysteine or glutathione. Cys102 on the heavy chain of MSCB97 is shown with flanking amino acids as their single letter codes. OXM refers to the amino acid portion of the peptide variant. Aib2, Lys30 and the bromoacetylated discrete polyethyleneglycol (dPEG)12 spacer are shown. His1 of the mAb is shown as the single letter code.

The overall synthetic scheme for the production of the mAb-OXM compound is shown in FIG. 10.

Preparation of Oxyntomodulin (OXM) Peptide Variant:

The resin-bound protected peptide was synthesized using standard 9-fluorenylmethyloxycarbonyl (Fmoc) amino acids (with the exception of the N-terminal His, Nα-Boc-His(Boc)-OH and Lys30, Nα-Fmoc-Lys(ivDDE)-OH) on PAL-PEG-polystyrene resin. Standard amino acid activation and Fmoc deprotection strategies were used throughout. Upon completion of the sequence, the side-chain of the C-terminal lysine was selectively deprotected by treatment with dilute anhydrous hydrazine in N,N-dimethylformamide (DMF). Fmoc-dPEG$_{12}$-CO$_2$H was coupled to the liberated amine using diisopropylcarbodiimide (DIC)/ethyl(hydroxyimino)-cyanoacetate activation. The Fmoc group was removed and the resulting amine was bromoacetylated using a solution of bromoacetic anhydride in DMF.

The peptide was removed from the resin with simultaneous deprotection of all the protecting groups by treatment with trifluoroacetic acid (TFA) containing phenol, water and triisopropylsilane as scavengers. The crude peptide was isolated by cold precipitation with ether and purified by reverse phase high performance liquid chromatography (RP-HPLC) using acetonitrile/water with 0.1% v/v TFA as eluent. The pure peptide was collected as a fluffy white solid after lyophilization and stored at −80° C.

Reduction of Monoclonal Antibody MSCB97:

The monoclonal antibody is isolated with the engineered Cys102 residue disulfide bonded to adventitious cysteine or glutathione residues scavenged either from the cytosol or from the growth medium. A preliminary reduction of these disulfides followed by removal of the unwanted cysteine is therefore required prior to conjugation of the OXM peptide variant. Reduction was accomplished with the mAb immobilized on protein A resin beads. Reductant (tricarboxyethyl phosphine, TCEP) was circulated through the column at pH 5 until reduction was complete (1 hr). The advantage of TCEP as reductant under these conditions is that while reduction is effective, reformation of the disulfide bond at the lower pH is negligible. After washing away the by-products, the reduced adsorbed protein was eluted from the column using an acidic buffer (sodium acetate at pH 3.5). The reduced mAb was dialyzed twice against 50 mM 3-(N-morpholino) propanesulfonic acid (MOPS) at pH 5.5

Smaller exploratory batches were prepared by reduction with 2.5 equivalents of TCEP vs. mAb in solution at pH 5. The reduction was allowed to proceed 2 hours at room temperature. Small molecule by-products were removed by gel filtration (PD10 column) and the reduced MSCB97 was eluted with 10 mM MOPS, pH 5.5.

Preparation of mAb-OXM Compound:

A solution of reduced MSCB97 was added to a 7.6-fold excess of lyophilized OXM peptide variant. 1 mM EDTA solution was added to protect the reactive thiols against metal-catalyzed oxidation, and the pH of the reaction solution was raised to 7.3 by addition of MOPS buffer (1 M, pH 8.1). The reaction was allowed to proceed 18 h at room temperature with gentle agitation. The reaction was quenched by adjustment to pH 5.5 by addition of 2 M acetic acid and the crude conjugate was purified by adsorption on protein A with washing to remove excess peptide, unfolded product and by-products. Elution of the product (sodium acetate, pH 3.6) was followed by dialysis into acetate buffer pH 5.

Three independent syntheses were performed starting with 250 mg, 500 mg and 500 mg of MSCB97, and the products were combined into a single batch.

Analysis of mAb-OXM Compound

The properties of the prepared mAb-OXM compound were analyzed using (i) analytical hydrophobic interaction chromatography (HIC), (ii) intact mass measurement by liquid chromatography electrospray ionization mass spectrometry (LC-ESIMS), (iii) analytical size-exclusion chromatography (SEC), and (iv) SDS-polyacrylamide gel electrophoresis.

Stability in Human and Monkey Plasma

Figure 12:
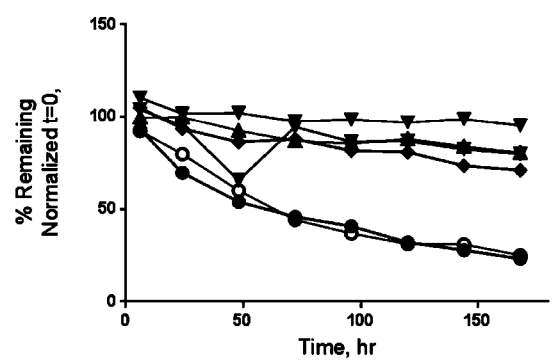
FIG. 12: Shows a graph demonstrating the functional stability of compound 2 in human plasma over 168 hours. Percent remaining normalized to time zero (t=0) of OXM peptide analog mAb conjugate compound 2▲, control 1, which had previously been demonstrated to be stable in ex vivo human plasma ♦, control 2, which had previously been demonstrated to be unstable in ex vivo human plasma ● and ○, and additional OXM peptide analog mAb conjugates compound 3 (mAb conjugated with H-Aib-QGTFTSDYS-KYLDERRARDFVEWLLNK-(COCH$_2$CH$_2$(OCH$_2$CH$_2$)$_{12}$NHCOCH$_2$Br)—NH$_2$ (SEQ ID NO: 25)) ▽ and compound 4 (mAb conjugated with H-Aib-QGTFTSDYSKYLDER-RARDFVEWLLNTK-(COCH$_2$CH$_2$(OCH$_2$CH$_2$)$_{12}$NHCOCH$_2$Br)—NH$_2$ (SEQ ID NO: 26)) ▼, over time in hours (hr) on the X-axis.
Figure 13:
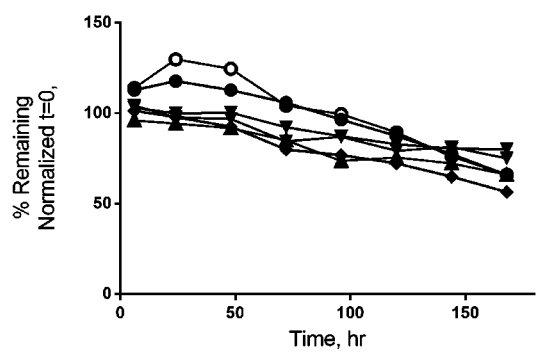
FIG. 13: Shows a graph demonstrating the functional stability of compound 2 in monkey plasma over 168 hours. Percent remaining normalized to time zero (t=0) of compound 2 ▲, control 1 previously demonstrated to be stable in ex vivo human plasma ♦, control 2 previously demonstrated to be unstable in ex vivo human plasma ● and ○, and additional OXM peptide analog mAb conjugates compound 3 ▽ and compound 4▼, over time in hours (hr) on the X-axis.

OXM is metabolized rapidly by plasma peptidases. To determine the resistance of the mAb-OXM compound ("compound 2") (FIG. 11) to enzymatic degradation in human and monkey plasma, the ex vivo stability of compound 2 was evaluated. Compound 2 was incubated at 20 nM with fresh (never frozen) heparinized plasma at 37° C. for up to 168 hours. Bioanalysis was conducted using a functional cell-based bioassay measuring cAMP production in human GLP-1 receptor transfected HEK cells. The amount of cAMP produced was directly proportional to the concentration of the active OXM analog, and levels of active OXM analogs in the stability samples were determined in this assay by interpolating from reference standards of known concentrations. This assay was used for ranking of stability relative to the previously determined more stable control, control 1, and the previously determined less stable control, control 2. The data was used to rank relative stability, and are shown in FIGS. 12 and 13.

Example 8: In Vitro Studies: In Vitro Potency of Compound 2 at the Human, Mouse, Rat, and Cynomolgus Monkey GLP1 and Glucagon Receptors The potency and species specificity of compounds of interest, including compound 2, were characterized in assays using HEK293 cells transfected to stably express either human, cynomolgus monkey, rat or mouse GLP1 or GCG receptors. For each receptor assay, the clonal cells were seeded into 384-well plates at the appropriate densities ranging from 2000-5000 cells/per well. Compounds were diluted in HBSS supplemented with 5 mM HEPES, 0.1% BSA and 0.5 mM IBMX and added to the cells. The cell plates were incubated at room temperature for 5 or 10 minutes depending on the cell clone and then lysed for cAMP measurement. cAMP concentrations were quantitated using LANCE cAMP kits with an EnVision plate reader. Standard curves were included in each assay plate for back calculation of cAMP concentrations. Dose-response curves were analyzed and compound $EC_{50}$ values calculated with Graphpad Prism or Crucible. The $EC_{50}$ data are summarized in Tables 9-10.

TABLE 9

Summary of EC50 values (nM) from human GLP1 and glucagon receptor cAMP assays.

| | Human | |
| --- | --- | --- |
| | GCGR | GLP1R |
| Glucagon | 0.05 ± 0.01 | 0.96 ± 0.21 |
| Ser-8 GLP1 | >100 | 0.07 ± 0.01 |
| OXM | 3.01 ± 0.35 | 2.40 ± 0.59 |
| Compound 2 | 3.31 ± 0.22 | 0.43 ± 0.02 |
| Dulaglutide | >100 | 0.17 ± 0.04 |

Values represent mean ± SEM from 3-7 experiments.

TABLE 10

Summary of $EC_{50}$ values (nM) from mouse, rat, and cynomolgus monkey GLP1 and glucagon receptor cAMP assays.

| | Mouse | | Rat | | Cynomolgus Monkey | |
| --- | --- | --- | --- | --- | --- | --- |
| | GCGR | GLP1R | GCGR | GLP1R | GCGR | GLP1R |
| Glucagon | 0.09 ± 0.01 | 2.13 ± 0.42 | 1.57 ± 0.33 | 4.73 ± 0.20 | 0.03 ± 0.002 | 1.96 ± 0.38 |
| Ser-8 GLP1 | >100 | 0.06 ± 0.005 | >100 | 0.14 ± 0.03 | >100 | 0.08 ± 0.002 |
| OXM | 6.31 ± 2.58 | 1.90 ± 0.31 | 12.74 ± 3.54 | 0.98 ± 0.16 | 0.49 ± 0.08 | 0.80 ± 0.07 |
| Compound 2 | 0.82 ± 0.38 | 0.11 ± 0.02 | 5.90 ± 1.46 | 0.97 ± 0.13 | 2.03 ± 0.14 | 0.40 ± 0.03 |
| Dulaglutide | >100 | 0.035 ± 0.002 | >100 | 0.13 ± 0.03 | >100 | 0.18 ± 0.01 |

Values represent mean ± SEM from 3-8 experiments.

Example 9: Potency at Other Related GPCRs

The potency of compound 2 was evaluated in assays using cells expressing several class B GPCRs. Compound 2 was tested in a panel of six in vitro cAMP assays using cells expressing CALCR, PTHR1, PTHR2, CRHR1, CRHR2 and VIPR1. The assays were performed according to the vendor's standard operating procedures with a positive control included for each receptor tested.

Additionally, compound 2 was tested in a stable cell line expressing the human GIP receptor. The cells were seeded into 384-well plates and treated 24 hours later with the compounds for 5 minutes at room temperature. cAMP concentrations were measured using a CisBio HTRF cAMP kit and the results analyzed using GraphPad Prism. The data are shown in Tables 11-12.

TABLE 11

Summary of compound 2 potency in cAMP assays.

| Compound | Target | RC$_{50}$ (µM) | Hill | Curve Bottom | Curve Top | Max response |
|---|---|---|---|---|---|---|
| Calcitonin | CALCR | 0.0007764259 | 1.5254 | −6.2187 | 105 | 101.04 |
| PTH(1-34) | PTHR1 | 0.001080165 | 1.8672 | −5.9767 | 101 | 93.574 |
| Sauvagine | CRHR1 | 0.0003082264 | 1.8133 | −3.2011 | 102.19 | 106.16 |
| Sauvagine | CRHR2 | 0.003395158 | 1.3095 | −1.175 | 102.76 | 107.04 |
| TIP-39 | PTHR2 | 0.0003934505 | 1.1032 | −3.7746 | 100.33 | 100.71 |
| VIP | VIPR1 | 0.0003567715 | 1.9827 | −0.96244 | 105 | 104.01 |
| Compound 2 | CALCR | >0.1 | | | | 0.070838 |
| Compound 2 | CRHR1 | >0.1 | | | | 1.5625 |
| Compound 2 | CRHR2 | >0.1 | | | | 0.928 |
| Compound 2 | PTHR1 | >0.1 | | | | 0.86197 |
| Compound 2 | PThR2 | >0.1 | | | | 2.2789 |
| Compound 2 | VIPR1 | >0.1 | | | | 0.60373 |

TABLE 12

Potency of compound 2 in human GIP receptor assay

| | assay 1 | | assay 2 | |
|---|---|---|---|---|
| | EC$_{50}$ (nM) | R square | EC$_{50}$ (nM) | R square |
| GIP | 2.31 | 1.00 | 1.28 | 0.99 |
| Compound 2 | ≥100 | ≥100 | ≥100 | ≥100 |
| Oxyntomodulin | ≥100 | ≥100 | ≥100 | ≥100 |

Example 10: In Vivo Studies: Single-Dose Efficacy in DIO Mice

Food intake, body weight, glucose tolerance and plasma FGF21 levels were assessed in DIO mice after a single dose of compound 2, or the GLP1R agonist, dulaglutide. One day prior to dosing, animals were weighed and grouped by BW. Mice were dosed as indicated by subcutaneous injection. The following morning, food was removed and the 6 hour fast was begun. BW and food weight (FW) were recorded. Fasting blood glucose was measured and blood was collected for insulin measurement at 12:00 pm. One hour later, mice were dosed with glucose (1 g/kg, 20% glucose, 5 mL/kg) intraperitoneally. An additional 20 µL of blood was collected via tail bleeding at 10 minutes for plasma insulin. Blood glucose levels were measured by glucometer at 10, 30, 60, and 90 minutes after glucose challenge. Mice were then euthanized with CO$_2$ and terminal blood samples were collected via cardiac puncture. The data are shown in Tables 13-19.

TABLE 13

Effect of compound 2 and dulaglutide on food intake (grams) in DIO mice over 18 hours after treatment

| Treatment | 24 hours pre-dose | 18 hours post-dose |
|---|---|---|
| Vehicle | 3.1 ± 0.1 | 2.9 ± 0.1 |
| Dulaglutide (0.3 nmol/kg) | 3.1 ± 0.1 | 1.5 ± 0.1*^ |
| Compound 2 (1.0 nmol/kg) | 3.2 ± 0.1 | 2.5 ± 0.1^# |
| Compound 2 (2.0 nmol/kg) | 3.4 ± 0.1 | 2.2 ± 0.1*^# |
| Compound 2 (4.0 nmol/kg) | 3.2 ± 0.1 | 1.7 ± 0.1*^ |
| Compound 2 (8.0 nmol/kg) | 3.4 ± 0.1 | 1.4 ± 0.2*^ |

*p < 0.01, versus Vehicle (18 hours post-dose); ^p < 0.001, versus respective 24 hours pre-dose; #p < 0.0001, versus dulaglutide (0.3 nmol/kg) 18 hours post-dose
Two-Way ANOVA, Sidak's multiple comparisons test
Values represent mean ± SEM for data from 8 animals per time point per group, except for Vehicle 24 hours pre-dose (n = 7)

TABLE 14

Effect of compound 2 and dulaglutide on percent body weight change in DIO mice 18 hours after treatment

| Treatment | Weight Change (%) |
|---|---|
| Vehicle | −0.7 ± 0.3 |
| Dulaglutide (0.3 nmol/kg) | −4.1 ± 0.3* |
| Compound 2 (1.0 nmol/kg) | −1.9 ± 0.3*^ |
| Compound 2 (2.0 nmol/kg) | −2.8 ± 0.4*^ |
| Compound 2 (4.0 nmol/kg) | −4.4 ± 0.3* |
| Compound 2 (8.0 nmol/kg) | −5.2 ± 0.3*^ |

*p < 0.01, versus Vehicle; ^p < 0.05, versus dulaglutide (0.3 nmol/kg)
Two-Way ANOVA RM, Tukey's multiple comparisons test. Data only shown for 18 hour time point
Percent weight change is calculated relative to body weights on day 0 (before dosing)
Values represent mean ± SEM for data from 8 animals per group

TABLE 15

Effect of compound 2 and dulaglutide on blood glucose (mg/dL) in DIO mice during an IPGTT 24 hours after treatment

| Treatment | Time (min) | | | | |
|---|---|---|---|---|---|
| | 0 | 10 | 30 | 60 | 90 |
| Vehicle | 215 ± 9 | 353 ± 20 | 436 ± 19 | 424 ± 25 | 391 ± 25 |
| Dulaglutide (0.3 nmol/kg) | 140 ± 7 | 264 ± 18 | 267 ± 22 | 228 ± 12 | 193 ± 9 |
| Compound 2 (1.0 nmol/kg) | 169 ± 6 | 349 ± 17 | 411 ± 30 | 411 ± 19 | 384 ± 18 |
| Compound 2 (2.0 nmol/kg) | 138 ± 11 | 288 ± 19 | 349 ± 27 | 303 ± 29 | 229 ± 20 |
| Compound 2 (4.0 nmol/kg) | 114 ± 8 | 235 ± 23 | 237 ± 34 | 239 ± 30 | 195 ± 25 |
| Compound 2 (8.0 nmol/kg) | 96 ± 7 | 206 ± 13 | 168 ± 22 | 166 ± 19 | 131 ± 12 |

Values represent mean ± SEM for data from 8 animals per time point per group

TABLE 16

Blood glucose net AUC during an IPGTT in DIO mice 24 hours after treatment

| Treatment | Blood Glucose Net AUC |
|---|---|
| Vehicle | 16539 ± 1400 |
| dulaglutide (0.3 nmol/kg) | 8471 ± 1204* |
| Compound 2 (1.0 nmol/kg) | 19214 ± 1596^ |
| Compound 2 (2.0 nmol/kg) | 13805 ± 1840 |

TABLE 16-continued

Blood glucose net AUC during an IPGTT in DIO mice 24 hours after treatment

| Treatment | Blood Glucose Net AUC |
|---|---|
| Compound 2 (4.0 nmol/kg) | 9827 ± 1046* |
| Compound 2 (8.0 nmol/kg) | 6035 ± 742* |

*$p < 0.05$, versus Vehicle; ^$p < 0.05$, versus dulaglutide (0.3 nmol/kg) and JNJ-64151789 (4.0 and 8.0 nmol/kg)
One-Way ANOVA, Tukey's multiple comparisons test
Values represent mean ± SEM for data from 8 animals per group

TABLE 17

Effect of compound 2 and dulaglutide on 6 hour fasting glucose (mg/dL) in DIO mice, 24 hours after treatment

| Treatment | Blood Glucose (mg/dL) |
|---|---|
| Vehicle | 215 ± 9 |
| Dulaglutide (0.3 nmol/kg) | 140 ± 7* |
| Compound 2 (1.0 nmol/kg) | 169 ± 6* |
| Compound 2 (2.0 nmol/kg) | 138 ± 11* |
| Compound 2 (4.0 nmol/kg) | 114 ± 8* |
| Compound 2 (8.0 nmol/kg) | 96 ± 7*^ |

*$p < 0.05$, versus Vehicle; ^$p < 0.05$, versus dulaglutide (0.3 nmol/kg)
One-Way ANOVA, Tukey's multiple comparisons test
Values represent mean ± SEM for data from 8 animals per group

TABLE 18

Effect of compound 2 and dulaglutide on plasma insulin levels (ng/ml) in DIO mice pre-glucose challenge (24 hours after treatment) and 10 minutes post-glucose challenge during an IPGTT

| | Plasma Insulin (ng/mL) | |
|---|---|---|
| Treatment | Pre-glucose | 10 minutes post-glucose |
| Vehicle | 2.7 ± 0.4 | 2.0 ± 0.3 |
| Dulaglutide (0.3 nmol/kg) | 1.6 ± 0.2 | 1.7 ± 0.2 |
| Compound 2 (1.0 nmol/kg) | 2.8 ± 0.4 | 1.8 ± 0.2 |
| Compound 2 (2.0 nmol/kg) | 2.3 ± 0.5 | 2.9 ± 0.4 |
| Compound 2 (4.0 nmol/kg) | 2.1 ± 0.2 | 2.5 ± 0.5 |
| Compound 2 (8.0 nmol/kg) | 1.5 ± 0.4 | 2.7 ± 0.3 |

Values represent mean ± SEM for data from 8 animals per group

TABLE 19

Effect of compound 2 and dulaglutide on plasma FGF21 (ng/mL) in DIO mice 26 hours after treatment

| Treatment | Plasma FGF21 (ng/mL) |
|---|---|
| Vehicle | 0.4 ± 0.1 |
| Dulaglutide (0.3 nmol/kg) | 0.8 ± 0.2 |
| Compound 2 (1.0 nmol/kg) | 0.7 ± 0.1 |
| Compound 2 (2.0 nmol/kg) | 1.5 ± 0.3 |
| Compound 2 (4.0 nmol/kg) | 2.1 ± 0.4^ |
| Compound 2 (8.0 nmol/kg) | 3.5 ± 0.3* |

*$p < 0.0001$, versus all groups; ^$p < 0.05$, versus all groups except compound 2 (2.0 nmol/kg)
One-Way ANOVA, Tukey's multiple comparisons test
Values represent mean ± SEM for data from 8 animals per group

Example 11: In Vivo Studies: Repeat Dosing in DIO Mice

The effects of a GLP1R/GCGR dual agonist, compound 2, and the GLP1R agonist, dulaglutide in DIO mice were monitored during repeated dosing over 9 days. To control for the dosing frequency, all animals were dosed daily. Dosing frequency was determined on the basis of DIO mouse PK data for compound 2 and dulaglutide. Animals in the dulaglutide group received this drug daily. The vehicle-treated animals received vehicle daily. Those animals given compound 2 at 1.0, 2.0 or 4.0 nmol/kg were dosed with compound every third day and received vehicle on those days when they were not injected with compound. The day prior to initiating of dosing, animals were weighed and grouped by body weight. All mice were dosed as indicated by subcutaneous injection between 1-3 PM. Food intake and body weight were monitored daily between 1-3 PM in these treatment groups.

Beginning 24-hr after the first dosing, three groups of mice were pair-fed (PF) to the 1.0, 2.0, or 4.0 nmol/kg compound 2-treated animals. The amount of food in the hopper of pair-fed mice was adjusted to match the average food consumed in the previous 24 hours by mice in the compound treatment group to which they were being matched. All PF groups were dosed daily with vehicle. On the ninth day (or Day 10 for the pair-fed groups), animals were fasted for 6 hours and body weight and fasting glucose were measured. Blood was collected for measurements of insulin, FGF21 and plasma lipids. The food intake, body weight, body composition, fasting glucose, fasting insulin, fasting FGF21, and fasting plasma lipid data are shown in tables 20-26.

TABLE 20

Effect of compound 2 and dulaglutide on daily food intake (grams) in DIO mice over 9 days of treatment

| | Time (days) | | | | | | | | | |
|---|---|---|---|---|---|---|---|---|---|---|
| Treatment | 0 | 1 | 2 | 3 | 4 | 5 | 6 | 7 | 8 | 9 |
| Vehicle | 2.7 ± 0.1 | 2.9 ± 0.0 | 3.1 ± 0.1 | 2.9 ± 0.1 | 2.9 ± 0.1 | 3.0 ± 0.1 | 2.9 ± 0.1 | 3.0 ± 0.1 | 3.0 ± 0.1 | 2.9 ± 0.1 |
| Dulaglutide (0.3 nmol/kg) | 3.1 ± 0.2 | 1.5 ± 0.2* | 1.3 ± 0.2* | 1.7 ± 0.3* | 1.9 ± 0.2* | 2.1 ± 0.2* | 2.2 ± 0.2* | 2.3 ± 0.2 | 2.9 ± 0.4 | 2.5 ± 0.2 |
| Compound 2 (1.0 nmol/kg) | 3.1 ± 0.1 | 2.3 ± 0.1*# | 2.5 ± 0.1*# | 2.6 ± 0.2 | 2.4 ± 0.1*# | 2.7 ± 0.2# | 2.6 ± 0.1# | 2.9 ± 0.2# | 2.8 ± 0.1# | 2.7 ± 0.1 |

TABLE 20-continued

Effect of compound 2 and dulaglutide on daily food intake (grams) in DIO mice over 9 days of treatment

| Treatment | Time (days) | | | | | | | | | |
|---|---|---|---|---|---|---|---|---|---|---|
| | 0 | 1 | 2 | 3 | 4 | 5 | 6 | 7 | 8 | 9 |
| Compound 2 (2.0 nmol/kg) | 3.1 ± 0.1 | 2.0 ± 0.1* | 2.0 ± 0.1*^ | 2.7 ± 0.1^ | 2.5 ± 0.2^ | 2.3 ± 0.1 | 2.5 ± 0.2 | 2.7 ± 0.1 | 2.8 ± 0.3 | 2.7 ± 0.1 |
| Compound 2 (4.0 nmol/kg) | 2.9 ± 0.2 | 1.5 ± 0.1* | 1.5 ± 0.2* | 2.1 ± 0.2* | 1.7 ± 0.1* | 1.6 ± 0.1* | 1.6 ± 0.1* | 1.8 ± 0.2* | 2.2 ± 0.3*^ | 2.1 ± 0.1* |

*p<0.05, versus Vehicle;
^p<0.05, versus dulaglutide (0.3 nmol/kg);
p<0.05, versus compound 2 (4.0 nmol/kg)
Two-Way ANOVA RM, Tukey's multiple comparisons test
All PF groups received average food intake amounts (data not shown) from respective treated groups.
Values represent mean ± SEM for data from 6-10 animals per time point per group

TABLE 21

Effect of compound 2 and dulaglutide on percent body weight change in DIO mice over 9 days of treatment

| Treatment | Time (days) | | | | | | | | | |
|---|---|---|---|---|---|---|---|---|---|---|
| | 0 | 1 | 2 | 3 | 4 | 5 | 6 | 7 | 8 | 9 |
| V | 0.0 | −0.1 ± 0.2 | −0.1 ± 0.2* | −0.2 ± 0.2* | −0.7 ± 0.3* | −0.5 ± 0.3* | 0.2 ± 0.5* | 0.1 ± 0.6* | 0.0 ± 0.5* | −1.7 ± 0.6* |
| 1 | 0.0 | −3.7 ± 0.3 | −6.2 ± 0.6 | −7.8 ± 0.8 | −9.2 ± 0.8 | −10.1 ± 0.8 | −10.2 ± 0.8 | −10.7 ± 1.0 | −11.1 ± 0.9 | −13.1 ± 1.1 |
| 2 | 0.0 | −1.9 ± 0.4 | −2.9 ± 0.5^ | −3.2 ± 0.4^ | −4.4 ± 0.7^& | −4.7 ± 0.8^& | −4.5 ± 0.8^& | −5.3 ± 1.0^& | −5.2 ± 1.1^& | −6.6 ± 1.1^& |
| 3 | 0.0 | −1.6 ± 0.3 | −2.7 ± 0.4^ | −3.5 ± 0.4^ | −3.8 ± 0.3^ | −3.8 ± 0.4^ | −3.9 ± 0.5^ | −3.5 ± 0.5^ | −3.4 ± 0.5^ | −4.5 ± 0.5^ |
| 4 | 0.0 | −2.8 ± 0.4 | −4.7 ± 0.5 | −4.9 ± 0.6^ | −7.1 ± 0.7 | −8.0 ± 0.8 | −8.0 ± 0.8 | −9.1 ± 0.8# | −10.0 ± 0.9# | −11.5 ± 0.9# |
| 5 | 0.0 | −3.0 ± 0.4 | −4.5 ± 0.4 | −5.1 ± 0.5^ | −5.3 ± 0.5^ | −5.8 ± 0.5^ | −6.1 ± 0.5^ | −5.8 ± 0.5^ | −6.2 ± 0.4^ | −6.9 ± 0.4^ |
| 6 | 0.0 | −3.7 ± 0.3 | −6.8 ± 0.3 | −8.8 ± 0.5$ | −11.6 ± 0.6#$ | −14.2 ± 0.7^#$ | −15.6 ± 0.9^#$ | −18.4 ± 1.2^#$ | −20.4 ± 1.5^#$ | −21.9 ± 1.6^#$ |
| 7 | 0.0 | −3.6 ± 0.1 | −5.6 ± 0.1 | −6.9 ± 0.1 | −7.9 ± 0.2 | −9.1 ± 0.2 | −10.5 ± 0.3 | −11.4 ± 0.3 | −12.3 ± 0.3 | −13.3 ± 0.3 |

T: treatment;
V: vehicle;
1: dulaglutide (0.3 nmol/kg);
2-3: compound 2 (1.0 nmol/kg);
4-5: compound 2 (2.0 nmol/kg);
6-7: compound 2 (4.0 nmol/kg)
*p<0.01, versus all other treatments;
^p<0.05, versus dulaglutide (0.3 nmol/kg);
p<0.05, versus respective PF group;
$p<0.05, versus JNJ-64151789 (1.0 and 2.0 nmol/kg);
&p<0.05, versus JNJ-64151789 (2.0 nmol/kg)
Two-Way ANOVA RM, Tukey's multiple comparisons test.
% Weight change is calculated relative to body weights on day 0 (before dosing)
Values represent mean ± SEM for data from 10 animals per time point per group

TABLE 22

Effect of compound 2 and dulaglutide on body composition (mass and percent body weight) in DIO mice after repeated dosing

| Treatment | Time (days) | | | |
|---|---|---|---|---|
| | Mass (g) | | % of Body Weight | |
| | Lean | Fat | Lean | Fat |
| Vehicle | 24.0 ± 0.2 | 10.6 ± 0.5 | 57.5 ± 0.8 | 25.4 ± 0.8 |
| Dulaglutide (0.3 nmol/kg) | 22.1 ± 0.3* | 7.6 ± 1.1 | 61.0 ± 1.7 | 22.8 ± 1.2 |
| Compound 2 (1.0 nmol/kg) | 23.1 ± 0.5 | 9.5 ± 1.3 | 57.4 ± 2.5 | 23.1 ± 2.5 |
| Compound 2 (1.0 nmol/kg) PF | 23.9 ± 0.3 | 10.6 ± 0.3 | 57.7 ± 0.7 | 25.5 ± 0.5 |
| Compound 2 (2.0 nmol/kg) | 22.2 ± 0.4* | 8.2 ± 0.7 | 59.7 ± 1.1 | 22.0 ± 1.6 |
| Compound 2 (2.0 nmol/kg) PF | 23.4 ± 0.1 | 9.8 ± 0.4 | 58.5 ± 0.8 | 24.4 ± 0.8 |

TABLE 22-continued

Effect of compound 2 and dulaglutide on body composition (mass and percent body weight) in DIO mice after repeated dosing

| | Time (days) | | | |
|---|---|---|---|---|
| | Mass (g) | | % of Body Weight | |
| Treatment | Lean | Fat | Lean | Fat |
| Compound 2 (4.0 nmol/kg) | 20.9 ± 0.3* | 7.4 ± 0.7 | 61.9 ± 2.4 | 21.6 ± 1.1 |
| Compound 2 (4.0 nmol/kg) PF | 21.4 ± 0.6 | 9.3 ± 0.5 | 56.8 ± 1.4 | 24.7 ± 1.0 |

*$p < 0.05$, versus Vehicle
One-Way ANOVA, Tukey's multiple comparisons test
Values represent mean ± SEM for data from 5 animals per group

TABLE 23

Effect of compound 2 and dulaglutide on 6 hour fasting glucose (mg/dL) in DIO mice, after repeated dosing

| Treatment | Blood Glucose (mg/dL) |
|---|---|
| Vehicle | 170 ± 5 |
| Dulaglutide (0.3 nmol/kg) | 123 ± 5* |
| Compound 2 (1.0 nmol/kg) | 164 ± 5^ |
| Compound 2 (1.0 nmol/kg) PF | 168 ± 7^ |
| Compound 2 (2.0 nmol/kg) | 140 ± 7* |
| Compound 2 (2.0 nmol/kg) PF | 155 ± 6^ |
| Compound 2 (4.0 nmol/kg) | 98 ± 4*# |
| Compound 2 (4.0 nmol/kg) PF | 133 ± 6* |

*$p < 0.05$, versus Vehicle; ^$p < 0.05$, versus dulaglutide (0.3 nmol/kg); #$p < 0.05$, versus JNJ-64151789 (4.0 nmol/kg) PF
One-Way ANOVA, Tukey's multiple comparisons test
Values represent mean ± SEM for data from 10 animals per group

TABLE 24

Effect of compound 2 and dulaglutide on 6 hour fasting plasma insulin (ng/mL) in DIO mice after repeated dosing

| Treatment | Plasma Insulin (ng/mL) |
|---|---|
| Vehicle | 3.0 ± 0.4 |
| Dulaglutide (0.3 nmol/kg) | 1.4 ± 0.2* |
| Compound 2 (1.0 nmol/kg) | 2.0 ± 0.3 |
| Compound 2 (1.0 nmol/kg) PF | 2.0 ± 0.1* |
| Compound 2 (2.0 nmol/kg) | 1.1 ± 0.1*^ |
| Compound 2 (2.0 nmol/kg) PF | 2.3 ± 0.3 |
| Compound 2 (4.0 nmol/kg) | 0.5 ± 0.1* |
| Compound 2 (4.0 nmol/kg) PF | 1.2 ± 0.1* |

*$p < 0.05$, versus Vehicle; ^$p < 0.05$, versus compound 2 (2.0 nmol/kg) PF
One-Way ANOVA, Tukey's multiple comparisons test
Values represent mean ± SEM for data from 10 animals per group

TABLE 25

Effect of compound 2 and dulaglutide on 6 hour fasting plasma FGF21 (ng/mL) in DIO mice after repeated dosing

| Treatment | FGF21 (ng/mL) |
|---|---|
| Vehicle | 0.7 ± 0.1 |
| Dulaglutide (0.3 nmol/kg) | 0.5 ± 0.1 |
| Compound 2 (1.0 nmol/kg) | 0.7 ± 0.2 |
| Compound 2 (1.0 nmol/kg) PF | 0.4 ± 0.1 |
| Compound 2 (2.0 nmol/kg) | 0.6 ± 0.1 |
| Compound 2 (2.0 nmol/kg) PF | 0.2 ± 0.1 |
| Compound 2 (4.0 nmol/kg) | 1.5 ± 0.3*^ |
| Compound 2 (4.0 nmol/kg) PF | 0.3 ± 0.1 |

*$p < 0.05$, versus all groups; ^$p < 0.05$, versus compound 2 (4.0 nmol/kg) PF
One-Way ANOVA, Tukey's multiple comparisons test
Values represent mean ± SEM for data from 10 animals per group, except compound 2 (1.0 nmol/kg) and compound 2 (4.0 nmol/kg) PF where N = 9

TABLE 26

Effect of compound 2 and dulaglutide on plasma lipids in DIO mice after repeated dosing

| | Time (days) | | | |
|---|---|---|---|---|
| Treatment | Free Fatty Acids (μmol/L) | Free Glycerol (mmol/L) | Tri-glycerides (mg/dL) | Total cholesterol (mg/dL) |
| Vehicle | 66.2 ± 3.9 | 0.6 ± 0.0 | 30.1 ± 2.8 | 142.1 ± 5.2 |
| Dulaglutide (0.3 nmol/kg) | 73.2 ± 12.0 | 0.5 ± 0.1 | 24.1 ± 2.3 | 146.1 ± 3.3 |
| Compound 2 (1.0 nmol/kg) | 71.8 ± 5.4 | 0.5 ± 0.0* | 32.5 ± 4.5 | 149.1 ± 2.3 |
| Compound 2 (1.0 nmol/kg) PF | 58.8 ± 6.1 | 0.6 ± 0.1 | 33.7 ± 4.1 | 161.4 ± 2.0 |
| Compound 2 (2.0 nmol/kg) | 73.8 ± 4.6 | 0.5 ± 0.0* | 30.4 ± 3.4 | 128.0 ± 6.6# |
| Compound 2 (2.0 nmol/kg) PF | 84.8 ± 25.3 | 0.6 ± 0.0* | 34.5 ± 3.3 | 149.9 ± 4.4 |
| Compound 2 (4.0 nmol/kg) | 71.2 ± 6.4 | 0.4 ± 0.0* | 16.1 ± 2.0$ | 85.7 ± 4.9^ |
| Compound 2 (4.0 nmol/kg) PF | 102.6 ± 14.5 | 0.7 ± 0.0 | 31.8 ± 1.1 | 137.8 ± 5.7 |

Figure 14:
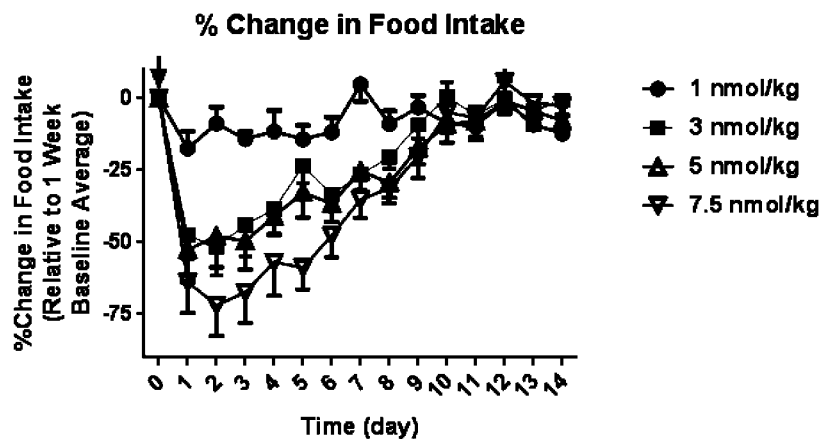
FIG. 14: Shows a graph demonstrating % change in food intake in cynomolgus monkeys treated with compound 2.
Figure 15:
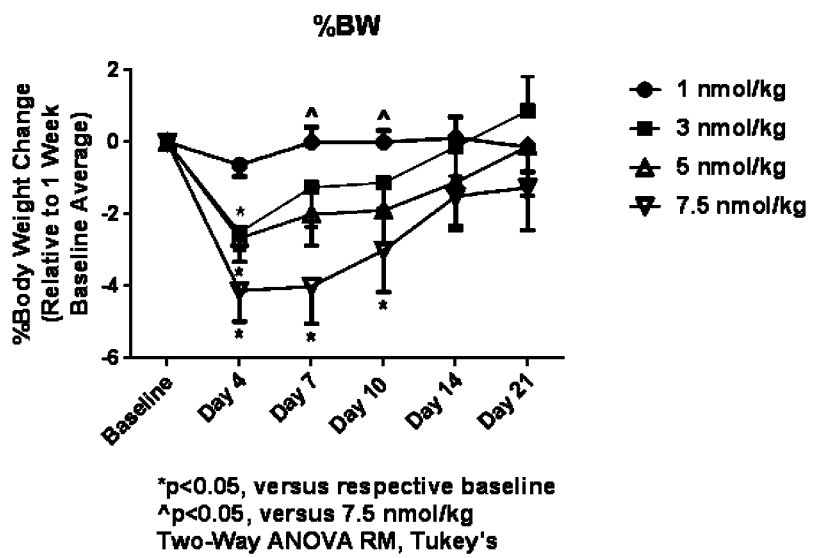
FIG. 15: Shows a graph demonstrating % change in body weight in cynomolgus monkeys treated with compound 2.

*$p < 0.05$, versus compound 2 (4.0 nmol/kg) PF; ^$p < 0.05$, versus all other groups;
$p < 0.05$, versus compound 2 (1.0 nmol/kg) and compound 2 (2.0 nmol/kg) PF; $$p < 0.05$, versus all groups except dulaglutide (0.3 nmol/kg)
One-Way ANOVA, Tukey's multiple comparisons test
Values represent mean ± SEM for data from 10 animals per group for free fatty acids, 8-10 animals per group for free glycerol, 9-10 animals per group for triglycerides and total cholesterol Example 12: In Vivo Studies: Single Dose Efficacy in Cynomolgus Monkeys Biologics naïve cynomolgus monkeys were monitored daily for food intake during the three weeks prior to treatment. At the initiation of treatment, animals were placed in four groups to achieve similar mean body weight (n=8-9, mean body weight 7.4-7.9 kg, for each group). Animals in each group received a single subcutaneous dose corresponding to 1, 3, 5, or 7.5 nmol/kg of compound 2. Food consumption was monitored daily for an additional 14 days. Body weights were measured on the day of dosing and 4, 7, 10, 14 and 21 days after dosing. The percentage change in food intake was determined daily by comparing the food intake on that day to the average daily food intake during the seven days prior to dosing. The results are provided in FIGS. 14 and 15.

Example 13: Pharmacokinetics (PK), Pharmacokinetic (PK)/Pharmacodynamics (PD) Analysis DIO Mouse PK The time-course of compound 2 was assessed in DIO mice (Table 27). Animals (n=3 per time point) were dosed s.c. at 10 nmol/k.

TABLE 27

Time course of plasma exposures (nM) of compound 2 measured by bioassay and immunoassay

| Time (hours) | Plasma exposures (nM) | |
| --- | --- | --- |
| | Bioassay | Immunoassay |
| 0 | N/A | N/A |
| 7 | 6.9 ± 2.0 | 16.7 ± 6.7 |
| 24 | 32.6 ± 3.5 | 71.0 ± 8.9 |
| 48 | 55.5 ± 2.4 | 111.9 ± 16.4 |
| 72 | 45.3 ± 4.0 | 95.7 ± 9.7 |
| 96 | 42.3 ± 14.5 | 86.8 ± 6.8 |
| 120 | 26.5 ± 6.9 | 58.1 ± 14.2 |

Values represent mean ± SEM for data from 3 animals per time point per group

Rat PK

The pharmacokinetic parameters of compound 2 were assessed in Sprague-Dawley rats. For determination of pharmacokinetic parameters (Table 28), bioassay-determined exposures were used from samples collected at 0, 24, 48, 72, 144, 216, 312, 408, and 504 hours after dosing.

TABLE 28

Pharmacokinetic parameters of compound 2 in Sprague-Dawley rats

| Parameter | Subcutaneous | Intravenous |
| --- | --- | --- |
| $C_{max}$ (nM) | 5.7 ± 2.1 | N/A |
| $T_{max}$ (hours) | 64.0 ± 13.9 | N/A |
| $AUC_{0-\infty}$, (nM*hours) | 456 ± 154 | 865 ± 185 |
| $t_{1/2}$ (hours) | 38.5 ± 12.8 | 26.2 ± 6.2 |

Data are mean +/− standard deviation, exposures bioassay

Cynomolgus Monkey PK

The pharmacokinetic parameters of compound 2 were assessed in cynomolgus monkey. Animals were dosed i.v. or s.c. at 6.45 nmol/kg. For determination of pharmacokinetic parameters (Table 29), bioassay-determined exposures were used from samples collected at 0, 1, 6, 24, 48, 72, 120, 240, 336, 432, and 528 hours after dosing.

TABLE 29

Pharmacokinetic parameters of compound 2 in cynomolgus monkeys

| Parameter | Subcutaneous | Intravenous |
| --- | --- | --- |
| $C_{max}$ (nM) | 89.1 ± 8.7 | N/A |
| $T_{max}$ (hours) | 56.0 ± 13.9 | N/A |
| $AUC_{0-\infty}$, (nM*hours) | 11,700 ± 1380 | 14,700 ± 5260 |
| $t_{1/2}$ (hours) | 51.9 ± 6.2 | 55.9 ± 41.7 |

Values represent mean ± standard deviation

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the present description.

All documents cited herein are incorporated by reference.

What is claimed:

1. A method of reducing food intake or treating a disease or disorder in a subject in need thereof, wherein said disease or disorder is selected from the group consisting of obesity, type II diabetes, metabolic syndrome, insulin resistance, impaired glucose tolerance, hyperglycemia, hyperinsulinemia, hypertriglyceridemia, dyslipidemia, atherosclerosis, diabetic nephropathy, hypertension, non-alcoholic fatty liver disease (NAFLD), and non-alcoholic steatohepatitis (NASH), the method comprising administering to the subject an effective amount of the pharmaceutical composition comprising a conjugate comprising:
   a. a monoclonal antibody, wherein the monoclonal antibody comprises a heavy chain variable domain (VH) having the polypeptide sequence of SEQ ID NO:12, and a light chain variable domain (VL) having the polypeptide sequence of SEQ ID NO:14; and
   b. at least one pharmacologically active moiety;
   and a pharmaceutically acceptable carrier.

2. The method of claim 1, wherein the monoclonal antibody further comprises a Fc portion.

3. The method of claim 2, wherein the monoclonal antibody comprises a heavy chain (HC having the polypeptide sequence of SEQ ID NO:13, and a light chain (LC) having the polypeptide sequence of SEQ ID NO:15.

4. The method of claim 1, wherein the pharmacologically active moiety is a therapeutic peptide.

5. The method of claim 4, wherein the therapeutic peptide is conjugated to the monoclonal antibody thereof at the cysteine residue of the polypeptide sequence of SEQ ID NO:18.

6. The method of claim 4, wherein the therapeutic peptide is conjugated to the monoclonal antibody via a linker.

7. The method of claim 6, wherein the linker comprises a peptide linker, a hydrocarbon linker, a polyethylene glycol (PEG) linker, a polypropylene glycol (PPG) linker, a polysaccharide linker, a polyester linker, or a hybrid linker consisting of PEG and an embedded heterocycle.

8. The method of claim 4, wherein the therapeutic peptide is selected from the group consisting of oxyntomodulin, glucagon-like peptide 1 (GLP1), exendin (exenatide), amylin (pramlintide), alpha-melanocyte stimulating hormone (MSH), cocaine- and amphetamine-regulated transcript (CART), neuropeptide Y receptor Y1 (NPY1) antagonists, neuropeptide Y receptor Y5 (NPY5) antagonists, neurotensin S, neuropeptide B, neuropeptide W, ghrelin, bombesin-like receptor 3 (BRS3), galanin, cholecystokinin (CCK), orexin, melanin-concentrating hormone (MCH), oxytocin, and stresscopin.

9. The method of claim 8, wherein the therapeutic peptide is oxyntomodulin comprising the polypeptide sequence of SEQ ID NO:24.

10. The method of claim 1, wherein the pharmaceutical composition is administered in combination with at least one additional agent.

11. The method of claim 10, wherein the additional agent is a glucagon-like-peptide-1 receptor modulator.

12. The method of claim 1, wherein the pharmaceutical composition is administered in combination with liraglutide or dulaglutide.

13. A method of reducing food intake or treating a disease or disorder in a subject in need thereof, wherein said disease or disorder is selected from the group consisting of obesity, type II diabetes, metabolic syndrome, insulin resistance, impaired glucose tolerance, hyperglycemia, hyperinsulinemia, hypertriglyceridemia, dyslipidemia, atherosclerosis, diabetic nephropathy, hypertension, non-alcoholic fatty liver disease (NAFLD), and non-alcoholic steatohepatitis (NASH), the method comprising administering to the subject an effective amount of the pharmaceutical composition comprising a conjugate comprising:
  a. a monoclonal antibody, wherein the monoclonal antibody comprises a heavy chain complementarity determining region 1 (HCDR1), a HCDR2, a HCDR3, a light chain complementarity determining region 1 (LCDR1), a LCDR2, and a LCDR3 having the polypeptide sequences of SEQ ID NO:16, 17, 18, 19, 20, and 21, respectively; and
  b. two different pharmaceutically active moieties;
  and a pharmaceutically acceptable carrier.

14. The method of claim 13, wherein the monoclonal antibody comprises a heavy chain variable domain (VH) having the polypeptide sequence of SEQ ID NO:12, and a light chain variable domain (VL) having the polypeptide sequence of SEQ ID NO:14.

15. The method of claim 14, wherein the monoclonal antibody further comprises a Fc portion.

16. The method of claim 15, wherein the monoclonal antibody comprises a heavy chain (HC) having the polypeptide sequence of SEQ ID NO:13, and a light chain (LC) having the polypeptide sequence of SEQ ID NO:15.

17. The method of claim 13, wherein the two different pharmacologically active moieties are therapeutic peptides.

18. The method of claim 17, wherein each of the therapeutic peptides is conjugated to the monoclonal antibody at the cysteine residue of the polypeptide sequence of SEQ ID NO:18.

19. The method of claim 17, wherein each of the therapeutic peptides is conjugated to the monoclonal antibody via a linker.

20. The method of claim 19, wherein the linker independently comprises a peptide linker, a hydrocarbon linker, a polyethylene glycol (PEG) linker, a polypropylene glycol (PPG) linker, a polysaccharide linker, a polyester linker, or a hybrid linker consisting of PEG and an embedded heterocycle.

21. The method of claim 17, wherein the therapeutic peptides are selected from the group consisting of oxyntomodulin, glucagon-like peptide 1 (GLP1), exendin (exenatide), amylin (pramlintide), alpha-melanocyte stimulating hormone (MSH), cocaine- and amphetamine-regulated transcript (CART), neuropeptide Y receptor Y1 (NPY1) antagonists, neuropeptide Y receptor Y5 (NPY5) antagonists, neurotensin S, neuropeptide B, neuropeptide W, ghrelin, bombesin-like receptor 3 (BRS3), galanin, cholecystokinin (CCK), orexin, melanin-concentrating hormone (MCH), oxytocin, and stresscopin.

22. The method of claim 13, wherein the pharmaceutical composition is administered in combination with at least one additional agent.

23. The method of claim 22, wherein the additional agent is a glucagon-like-peptide-1 receptor modulator.

24. The method of claim 13, wherein the pharmaceutical composition is administered in combination with liraglutide or dulaglutide.

* * * * *

SEQUENCE LISTING

```
<160> NUMBER OF SEQ ID NOS: 27

<210> SEQ ID NO 1
<211> LENGTH: 34
<212> TYPE: PRT
<213> ORGANISM: Homo sapiens

<400> SEQUENCE: 1

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 2
<211> LENGTH: 35
<212> TYPE: PRT
<213> ORGANISM: Artificial Sequence
<220> FEATURE:
<223> OTHER INFORMATION: Compound 1
<220> FEATURE:
<221> NAME/KEY: Ala
<222> LOCATION: (1)..(1)
<223> OTHER INFORMATION: Ala, wherein the alanine is a beta-alanine with
      a cyclic modification
<220> FEATURE:
<221> NAME/KEY: Lys
<222> LOCATION: (10)..(10)
```

```
<223> OTHER INFORMATION: Lys with a PEG12-mAb chemical modification
<220> FEATURE:
<221> NAME/KEY: Cys
<222> LOCATION: (30)..(30)
<223> OTHER INFORMATION: Cys, wherein cys is homocysteine with a cyclic
      modification
<220> FEATURE:
<221> NAME/KEY: Arg
<222> LOCATION: (34)..(34)
<223> OTHER INFORMATION: Arg with a psi-(R35, Y36) chemical modification
<220> FEATURE:
<221> NAME/KEY: Tyr
<222> LOCATION: (35)..(35)
<223> OTHER INFORMATION: Tyr with a psi-(R35, Y36) chemical modification

<400> SEQUENCE: 2

Ala Ile Lys Pro Glu Ala Pro Gly Glu Lys Ala Ser Pro Glu Glu Leu
1               5                   10                  15

Asn Arg Tyr Tyr Ala Ser Leu Arg His Tyr Leu Asn Leu Cys Thr Arg
            20                  25                  30

Gln Arg Tyr
        35

<210> SEQ ID NO 3
<211> LENGTH: 107
<212> TYPE: PRT
<213> ORGANISM: Homo sapiens

<400> SEQUENCE: 3

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 4
<211> LENGTH: 119
<212> TYPE: PRT
<213> ORGANISM: Homo sapiens

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95

Ala Lys Tyr Asp Gly Ile Tyr Gly Glu Leu Asp Phe Trp Gly Gln Gly
                100                 105                 110

Thr Leu Val Thr Val Ser Ser
        115

<210> SEQ ID NO 5
<211> LENGTH: 10
<212> TYPE: PRT
<213> ORGANISM: Homo sapiens

<400> SEQUENCE: 5

Tyr Asp Gly Ile Tyr Gly Glu Leu Asp Phe
1               5                   10

<210> SEQ ID NO 6
<211> LENGTH: 115
<212> TYPE: PRT
<213> ORGANISM: Artificial Sequence
<220> FEATURE:
<223> OTHER INFORMATION: Concatenation of IGHV3-23*01 and IGHJ1*01

<400> SEQUENCE: 6

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Glu Tyr Phe Gln His Trp Gly Gln Gly Thr Leu Val Thr
                100                 105                 110

Val Ser Ser
        115

<210> SEQ ID NO 7
<211> LENGTH: 98
<212> TYPE: PRT
<213> ORGANISM: Homo sapiens

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

Ala Lys

<210> SEQ ID NO 8
<211> LENGTH: 17
<212> TYPE: PRT
<213> ORGANISM: Homo sapiens

<400> SEQUENCE: 8

Ala Glu Tyr Phe Gln His Trp Gly Gln Gly Thr Leu Val Thr Val Ser
1               5                   10                  15

Ser

<210> SEQ ID NO 9
<211> LENGTH: 107
<212> TYPE: PRT
<213> ORGANISM: Artificial Sequence
<220> FEATURE:
<223> OTHER INFORMATION: Concatenation of IGKV3-11*01 and IGKJ1*01

<400> SEQUENCE: 9

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 10
<211> LENGTH: 95
<212> TYPE: PRT
<213> ORGANISM: Homo sapiens

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 11
<211> LENGTH: 12
<212> TYPE: PRT
<213> ORGANISM: Homo sapiens

<400> SEQUENCE: 11

Trp Thr Phe Gly Gln Gly Thr Lys Val Glu Ile Lys
1               5                   10

<210> SEQ ID NO 12
<211> LENGTH: 119
<212> TYPE: PRT
<213> ORGANISM: Artificial Sequence
<220> FEATURE:
<223> OTHER INFORMATION: MSCB97 VH

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Asp Gly Cys Tyr Gly Glu Leu Asp Phe Trp Gly Gln Gly
            100                 105                 110

Thr Leu Val Thr Val Ser Ser
        115

<210> SEQ ID NO 13
<211> LENGTH: 446
<212> TYPE: PRT
<213> ORGANISM: Artificial Sequence
<220> FEATURE:
<223> OTHER INFORMATION: MSCB97 HC

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Asp Gly Cys Tyr Gly Glu Leu Asp Phe Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu

```
                165                 170                 175
Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 14
<211> LENGTH: 107
<212> TYPE: PRT
<213> ORGANISM: Artificial Sequence
<220> FEATURE:
<223> OTHER INFORMATION: MSCB97 VL

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
```

```
                    85                  90                  95
Thr Phe Gly Gln Gly Thr Lys Val Glu Ile Lys
                100                 105

<210> SEQ ID NO 15
<211> LENGTH: 214
<212> TYPE: PRT
<213> ORGANISM: Artificial Sequence
<220> FEATURE:
<223> OTHER INFORMATION: MSCB97 LC

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 5
<212> TYPE: PRT
<213> ORGANISM: Artificial Sequence
<220> FEATURE:
<223> OTHER INFORMATION: MSCB97 HCDR1

<400> SEQUENCE: 16

Ser Tyr Ala Met Ser
1               5

<210> SEQ ID NO 17
<211> LENGTH: 17
<212> TYPE: PRT
<213> ORGANISM: Artificial Sequence
<220> FEATURE:
<223> OTHER INFORMATION: MSCB97 HCDR2

<400> SEQUENCE: 17
```

Ala Ile Ser Gly Ser Gly Gly Ser Thr Tyr Tyr Ala Asp Ser Val Lys
1               5                   10                  15

Gly

<210> SEQ ID NO 18
<211> LENGTH: 10
<212> TYPE: PRT
<213> ORGANISM: Artificial Sequence
<220> FEATURE:
<223> OTHER INFORMATION: MSCB97 HCDR3

<400> SEQUENCE: 18

Tyr Asp Gly Cys Tyr Gly Glu Leu Asp Phe
1               5                   10

<210> SEQ ID NO 19
<211> LENGTH: 11
<212> TYPE: PRT
<213> ORGANISM: Artificial Sequence
<220> FEATURE:
<223> OTHER INFORMATION: MSCB97 LCDR1

<400> SEQUENCE: 19

Arg Ala Ser Gln Ser Val Ser Ser Tyr Leu Ala
1               5                   10

<210> SEQ ID NO 20
<211> LENGTH: 7
<212> TYPE: PRT
<213> ORGANISM: Artificial Sequence
<220> FEATURE:
<223> OTHER INFORMATION: MSCB97 LCDR2

<400> SEQUENCE: 20

Asp Ala Ser Asn Arg Ala Thr
1               5

<210> SEQ ID NO 21
<211> LENGTH: 9
<212> TYPE: PRT
<213> ORGANISM: Artificial Sequence
<220> FEATURE:
<223> OTHER INFORMATION: MSCB97 LCDR3

<400> SEQUENCE: 21

Gln Gln Arg Ser Asn Trp Pro Leu Thr
1               5

<210> SEQ ID NO 22
<211> LENGTH: 29
<212> TYPE: PRT
<213> ORGANISM: Homo sapiens

<400> SEQUENCE: 22

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
                20                  25

<210> SEQ ID NO 23
<211> LENGTH: 37
<212> TYPE: PRT
<213> ORGANISM: Homo sapiens

<400> SEQUENCE: 23

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 24
<211> LENGTH: 30
<212> TYPE: PRT
<213> ORGANISM: Artificial Sequence
<220> FEATURE:
<223> OTHER INFORMATION: OXM variant 1
<220> FEATURE:
<221> NAME/KEY: Xaa
<222> LOCATION: (2)..(2)
<223> OTHER INFORMATION: Xaa is aminoisobutyric acid (alpha, alpha
      dimethylglycine)
<220> FEATURE:
<221> NAME/KEY: Lys
<222> LOCATION: (30)..(30)
<223> OTHER INFORMATION: Lys with a PEG12-mAb chemical modification

<400> SEQUENCE: 24

His Xaa Gln Gly Thr Phe Thr Ser Asp Tyr Ser Lys Tyr Leu Asp Glu
1               5                   10                  15

Arg Arg Ala Arg Asp Phe Val Glu Trp Leu Leu Asn Thr Lys
            20                  25                  30

<210> SEQ ID NO 25
<211> LENGTH: 29
<212> TYPE: PRT
<213> ORGANISM: Artificial Sequence
<220> FEATURE:
<223> OTHER INFORMATION: OXM variant 2
<220> FEATURE:
<221> NAME/KEY: Xaa
<222> LOCATION: (2)..(2)
<223> OTHER INFORMATION: Xaa is aminoisobutyric acid (alpha, alpha
      dimethylglycine)
<220> FEATURE:
<221> NAME/KEY: Lys
<222> LOCATION: (29)..(29)
<223> OTHER INFORMATION: Lys with a PEG12-mAb chemical modification

<400> SEQUENCE: 25

His Xaa Gln Gly Thr Phe Thr Ser Asp Tyr Ser Lys Tyr Leu Asp Glu
1               5                   10                  15

Arg Arg Ala Arg Asp Phe Val Glu Trp Leu Leu Asn Lys
            20                  25

<210> SEQ ID NO 26
<211> LENGTH: 30
<212> TYPE: PRT
<213> ORGANISM: Artificial Sequence
<220> FEATURE:
<223> OTHER INFORMATION: OXM variant 3
<220> FEATURE:
<221> NAME/KEY: Xaa
<222> LOCATION: (2)..(2)
<223> OTHER INFORMATION: Xaa is aminoisobutyric acid (alpha, alpha-
      dimethylglycine)
<220> FEATURE:
<221> NAME/KEY: Leu
<222> LOCATION: (27)..(27)
<223> OTHER INFORMATION: Leu, wherein leu is norleucine
<220> FEATURE:
<221> NAME/KEY: Lys
<222> LOCATION: (30)..(30)

```
<223> OTHER INFORMATION: Lys with a PEG12-mAb chemical modification

<400> SEQUENCE: 26

His Xaa Gln Gly Thr Phe Thr Ser Asp Tyr Ser Lys Tyr Leu Asp Glu
1               5                   10                  15

Arg Arg Ala Arg Asp Phe Val Glu Trp Leu Leu Asn Thr Lys
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: OXM variant 1/Compound 1
<220> FEATURE:
<221> NAME/KEY: Xaa
<222> LOCATION: (2)..(2)
<223> OTHER INFORMATION: Xaa is aminoisobutyric acid (alpha, alpha-
      dimethylglycine)
<220> FEATURE:
<221> NAME/KEY: Lys
<222> LOCATION: (30)..(30)
<223> OTHER INFORMATION: Lys with a PEG12-mAb chemical modification

<400> SEQUENCE: 27

His Xaa Gln Gly Thr Phe Thr Ser Asp Tyr Ser Lys Tyr Leu Asp Glu
1               5                   10                  15

Arg Arg Ala Arg Asp Phe Val Glu Trp Leu Leu Asn Thr Lys
            20                  25                  30
```